United States Patent
Pucci et al.

(10) Patent No.: US 11,472,856 B2
(45) Date of Patent: Oct. 18, 2022

(54) METHODS AND COMPOSITIONS FOR PROMOTING IMMUNE CELL FUNCTION

(71) Applicant: Torque Therapeutics, Inc., Cambridge, MA (US)

(72) Inventors: Ferdinando Pucci, Quincy, MA (US); Thomas Lars Andresen, Vanlose (DK); Douglas Scott Jones, Newton, MA (US); Ulrik Nielsen, Quincy, MA (US); James Andrew Rakestraw, Somerville, MA (US)

(73) Assignee: Torque Therapeutics, Inc., Cambridge, MA (US)

( * ) Notice: Subject to any disclaimer, the term of this patent is extended or adjusted under 35 U.S.C. 154(b) by 727 days.

(21) Appl. No.: 16/309,443

(22) PCT Filed: Jun. 13, 2017

(86) PCT No.: PCT/US2017/037249
§ 371 (c)(1),
(2) Date: Dec. 12, 2018

(87) PCT Pub. No.: WO2017/218533
PCT Pub. Date: Dec. 21, 2017

(65) Prior Publication Data
US 2020/0131239 A1   Apr. 30, 2020

Related U.S. Application Data

(60) Provisional application No. 62/349,473, filed on Jun. 13, 2016.

(51) Int. Cl.
| | | |
|---|---|---|
| *A61K 38/20* | (2006.01) | |
| *A61K 38/17* | (2006.01) | |
| *A61K 47/54* | (2017.01) | |
| *A61K 47/68* | (2017.01) | |
| *C07K 14/54* | (2006.01) | |
| *A61K 47/69* | (2017.01) | |
| *C07K 14/56* | (2006.01) | |
| *C07K 14/565* | (2006.01) | |
| *C07K 14/73* | (2006.01) | |
| *C07K 14/705* | (2006.01) | |

(52) U.S. Cl.
CPC .............. *C07K 14/54* (2013.01); *A61K 47/68* (2017.08); *A61K 47/6901* (2017.08); *C07K 14/56* (2013.01); *C07K 14/565* (2013.01); *C07K 14/70514* (2013.01); *C07K 14/70517* (2013.01); *C07K 14/70553* (2013.01); *C07K 14/70589* (2013.01); *C07K 2317/52* (2013.01); *C07K 2319/30* (2013.01)

(58) Field of Classification Search
CPC combination set(s) only.
See application file for complete search history.

(56) References Cited

U.S. PATENT DOCUMENTS

| | | |
|---|---|---|
| 5,409,698 A | 4/1995 | Anderson et al. |
| 5,453,491 A | 9/1995 | Takatsu et al. |
| 5,464,629 A | 11/1995 | Monshipouri et al. |
| 5,591,630 A | 1/1997 | Anderson et al. |
| 5,753,261 A | 5/1998 | Fernandez et al. |
| 5,773,006 A | 6/1998 | Anderson et al. |
| 5,994,126 A | 11/1999 | Steinman et al. |
| 6,001,973 A | 12/1999 | Strom et al. |
| 6,013,480 A | 1/2000 | Grabstein et al. |
| 6,077,519 A | 6/2000 | Storkus et al. |
| 6,117,982 A | 9/2000 | Chang |
| 6,120,751 A | 9/2000 | Unger |
| 6,143,292 A | 11/2000 | Slavin |
| 6,194,388 B1 | 2/2001 | Krieg et al. |
| 6,197,298 B1 | 3/2001 | Chang |
| 6,319,715 B1 | 11/2001 | Luo et al. |
| 6,475,483 B1 | 11/2002 | Steinman et al. |
| 6,479,286 B1 | 11/2002 | Nelson et al. |
| 6,544,549 B1 | 4/2003 | Boni et al. |
| 6,548,065 B1 | 4/2003 | Anderson et al. |
| 6,602,709 B1 | 8/2003 | Albert et al. |
| 6,613,582 B1 | 9/2003 | Kodadek et al. |
| 6,627,460 B1 | 9/2003 | Lihme et al. |
| 6,685,911 B1 | 2/2004 | Zitvogel et al. |
| 6,693,086 B1 | 2/2004 | Dow et al. |
| 6,787,132 B1 | 9/2004 | Gabizon et al. |
| 6,998,476 B2 | 2/2006 | Strom et al. |

(Continued)

FOREIGN PATENT DOCUMENTS

| | | |
|---|---|---|
| EP | 772624 B1 | 9/2000 |
| EP | 1111039 A1 | 6/2001 |

(Continued)

OTHER PUBLICATIONS

Garraud et al., "Are platelets cells? And if yes, are they immune cells?", Frontiers in immunology 6:1-8 (2015) (Year: 2015).*
Hartenstein, "Blood cells in blood cell development in the animal kingdom," Annu. Rev. Cell Dev. Biol. 22:677-712 (2006) (Year: 2006).*
Perera et al., "The role of Interleukin-15 in inflammation and immune responses to infection: implications for its therapeutic use", Microbes Infect. 14(3):247-261 (2012) (Year: 2012).*
U.S. Appl. No. 16/644,647, filed Mar. 5, 2020, Andresen.

(Continued)

*Primary Examiner* — Julie Ha
*Assistant Examiner* — Kristina M Hellman
(74) *Attorney, Agent, or Firm* — Goodwin Procter LLP

(57) ABSTRACT

The present disclosure features, at least in part, methods for conserving cell function, e.g., immune cell function, e.g., after one or more cycles of freezing and/or thawing the nucleated cell. In embodiments, the methods comprise contacting an immune cell with a protein nanoparticle comprising an IL-15 complex.

20 Claims, 18 Drawing Sheets

Specification includes a Sequence Listing.

(56) References Cited

U.S. PATENT DOCUMENTS

| | | |
|---|---|---|
| 7,108,863 B2 | 9/2006 | Zalipsky et al. |
| 7,122,202 B2 | 10/2006 | Allen et al. |
| 7,132,243 B2 | 11/2006 | Matsushita et al. |
| 7,223,544 B2 | 5/2007 | Luo et al. |
| 7,258,853 B2 | 8/2007 | Strom et al. |
| 7,402,431 B2 | 7/2008 | Har-Noy |
| 7,858,081 B2 | 12/2010 | Bernard et al. |
| 7,959,934 B2 | 6/2011 | Klinman et al. |
| 7,988,963 B1 | 8/2011 | Banchereau et al. |
| 8,067,237 B2 | 11/2011 | Mooney et al. |
| 8,124,084 B2 | 2/2012 | Lefrancois et al. |
| 8,153,425 B2 | 4/2012 | Pogue-Caley et al. |
| 8,163,879 B2 | 4/2012 | Wong et al. |
| 8,192,485 B2 | 6/2012 | Ravi |
| 8,232,101 B2 | 7/2012 | Cai et al. |
| 8,252,916 B2 | 8/2012 | Simard et al. |
| 8,287,857 B2 | 10/2012 | Dudley et al. |
| 8,323,696 B2 | 12/2012 | Hubbell et al. |
| 8,349,558 B2 | 1/2013 | Fatho et al. |
| 8,546,137 B2 | 10/2013 | Cannon et al. |
| 8,586,359 B2 | 11/2013 | Kruse |
| 8,623,837 B2 | 1/2014 | Fewell et al. |
| 8,629,098 B2 | 1/2014 | Fahmy et al. |
| 8,666,674 B2 | 3/2014 | Kruse |
| 8,728,806 B2 | 5/2014 | Decker et al. |
| 8,741,642 B2 | 6/2014 | Manjili et al. |
| 8,747,869 B2 | 6/2014 | Irvine et al. |
| 8,771,664 B2 | 7/2014 | Berraondo Lopez et al. |
| 8,871,191 B2 | 10/2014 | Pavlakis et al. |
| 8,951,542 B2 | 2/2015 | Irvine et al. |
| 9,089,593 B2 | 7/2015 | Hasumi |
| 9,090,640 B2 | 7/2015 | Bierbach et al. |
| 9,149,432 B2 | 10/2015 | Irvine et al. |
| 9,149,535 B2 | 10/2015 | Xu et al. |
| 9,211,321 B2 | 12/2015 | Karlsson-Parra et al. |
| 9,283,184 B2 | 3/2016 | Irvine et al. |
| 9,303,080 B2 | 4/2016 | Felber et al. |
| 9,303,247 B2 | 4/2016 | Abe et al. |
| 9,339,462 B2 | 5/2016 | Irvine et al. |
| 9,352,028 B2 | 5/2016 | Barner et al. |
| 9,393,199 B2 | 7/2016 | Irvine et al. |
| 9,415,070 B2 | 8/2016 | Irvine et al. |
| 9,445,994 B2 | 9/2016 | Irvine et al. |
| 9,476,028 B2 | 10/2016 | Karlsson-Parra et al. |
| 9,487,800 B2 | 11/2016 | Schonfeld et al. |
| 9,597,356 B2 | 3/2017 | Lee |
| 9,597,383 B2 | 3/2017 | Lee |
| 9,603,944 B2 | 3/2017 | Tang et al. |
| 9,616,020 B2 | 4/2017 | Irvine et al. |
| 9,629,877 B2 | 4/2017 | Cooper et al. |
| 9,724,393 B2 | 8/2017 | Conejo-Garcia et al. |
| 9,750,803 B2 | 9/2017 | Irvine et al. |
| 9,884,026 B2 | 2/2018 | Fahmy et al. |
| 9,907,753 B2 | 3/2018 | Irvine et al. |
| 10,226,510 B2 | 3/2019 | Tang et al. |
| 10,357,544 B2 | 7/2019 | Tang et al. |
| 10,588,942 B2 | 3/2020 | Tang et al. |
| 11,034,752 B2 | 6/2021 | Irvine et al. |
| 2001/0038859 A1 | 11/2001 | Maskiewicz et al. |
| 2001/0043929 A1 | 11/2001 | Zalipsky et al. |
| 2002/0001841 A1 | 1/2002 | Kaltoft et al. |
| 2002/0007173 A1 | 1/2002 | Kundig et al. |
| 2002/0085993 A1 | 7/2002 | Steinman et al. |
| 2002/0151004 A1 | 10/2002 | Craig |
| 2003/0054027 A1 | 3/2003 | Unger |
| 2003/0078339 A1 | 4/2003 | Kiser et al. |
| 2003/0082806 A1 | 5/2003 | Berenson et al. |
| 2003/0235619 A1 | 12/2003 | Allen et al. |
| 2004/0009149 A1 | 1/2004 | Altman et al. |
| 2004/0057935 A1 | 3/2004 | Yu et al. |
| 2004/0161413 A1 | 8/2004 | Laus et al. |
| 2004/0247624 A1 | 12/2004 | Unger et al. |
| 2005/0042298 A1 | 2/2005 | Pardridge et al. |
| 2005/0053667 A1 | 3/2005 | Irvine et al. |
| 2005/0130180 A1 | 6/2005 | Luo et al. |
| 2005/0214274 A1 | 9/2005 | Har-Noy |
| 2005/0214762 A1 | 9/2005 | Ross et al. |
| 2005/0266067 A1 | 12/2005 | Sengupta et al. |
| 2006/0046967 A1 | 3/2006 | Satyam |
| 2006/0057680 A1 | 3/2006 | Zheng et al. |
| 2006/0104945 A1 | 5/2006 | Choi |
| 2006/0216269 A1 | 9/2006 | Hasumi |
| 2006/0236411 A1 | 10/2006 | Dreher et al. |
| 2006/0246524 A1 | 11/2006 | Bauer et al. |
| 2006/0257361 A1 | 11/2006 | Watanabe et al. |
| 2006/0263857 A1 | 11/2006 | Lefrancois et al. |
| 2006/0270030 A1 | 11/2006 | Voigt et al. |
| 2006/0275371 A1 | 12/2006 | Dai et al. |
| 2006/0286066 A1 | 12/2006 | Basran |
| 2007/0059318 A1 | 3/2007 | Balu-Iyer et al. |
| 2007/0148246 A1 | 6/2007 | Luo et al. |
| 2007/0160578 A1* | 7/2007 | Waldmann ............ A61K 35/17 424/145.1 |
| 2007/0248584 A1 | 10/2007 | Kent |
| 2007/0298093 A1 | 12/2007 | Konur et al. |
| 2008/0014144 A1 | 1/2008 | Saltzman et al. |
| 2008/0131415 A1 | 6/2008 | Riddell et al. |
| 2008/0171059 A1 | 7/2008 | Howland et al. |
| 2008/0254537 A1 | 10/2008 | Boynton et al. |
| 2008/0267986 A1 | 10/2008 | Pfeifer et al. |
| 2008/0279836 A1 | 11/2008 | Har-Noy |
| 2009/0155204 A1 | 6/2009 | Beurskens et al. |
| 2010/0008930 A1 | 1/2010 | Stanulla et al. |
| 2010/0226973 A1 | 9/2010 | Fujii et al. |
| 2010/0255499 A1 | 10/2010 | Wender et al. |
| 2010/0266642 A1 | 10/2010 | Langer et al. |
| 2010/0310501 A1 | 12/2010 | Boyman et al. |
| 2010/0323018 A1 | 12/2010 | Irvine et al. |
| 2010/0324124 A1 | 12/2010 | Irvine et al. |
| 2011/0020388 A1 | 1/2011 | Zepp et al. |
| 2011/0081311 A1 | 4/2011 | Pavlakis et al. |
| 2011/0097346 A1 | 4/2011 | Rubiolo |
| 2011/0177156 A1 | 7/2011 | Szoka, Jr. et al. |
| 2011/0182870 A1 | 7/2011 | Leen et al. |
| 2011/0206740 A1 | 8/2011 | Karp et al. |
| 2011/0229529 A1 | 9/2011 | Irvine et al. |
| 2011/0229556 A1 | 9/2011 | Irvine et al. |
| 2011/0262963 A1 | 10/2011 | Geierstanger et al. |
| 2011/0293705 A1 | 12/2011 | Irvine et al. |
| 2012/0003295 A1 | 1/2012 | Jiang et al. |
| 2012/0121688 A1 | 5/2012 | Ishii et al. |
| 2012/0177724 A1 | 7/2012 | Irvine et al. |
| 2012/0276156 A1 | 11/2012 | Fraser et al. |
| 2012/0276157 A1 | 11/2012 | Fraser et al. |
| 2013/0045491 A1 | 2/2013 | Unutmaz |
| 2013/0203675 A1 | 8/2013 | DeSimone et al. |
| 2013/0302257 A1 | 11/2013 | Minko et al. |
| 2013/0302276 A1 | 11/2013 | Cantor et al. |
| 2013/0337471 A1 | 12/2013 | Nie et al. |
| 2014/0010793 A1 | 1/2014 | Lee |
| 2014/0010794 A1 | 1/2014 | Lee |
| 2014/0017170 A1 | 1/2014 | Irvine et al. |
| 2014/0134128 A1* | 5/2014 | Wong ................... C12P 21/00 424/85.2 |
| 2014/0212398 A1 | 7/2014 | Reisner et al. |
| 2014/0234351 A1 | 8/2014 | Bender et al. |
| 2014/0255363 A1 | 9/2014 | Metelitsa et al. |
| 2014/0377334 A1 | 12/2014 | Irvine et al. |
| 2015/0017723 A1 | 1/2015 | Rooney et al. |
| 2015/0044258 A1 | 2/2015 | Knaus et al. |
| 2015/0110740 A1 | 4/2015 | Tang et al. |
| 2015/0152188 A1 | 6/2015 | Morisseau et al. |
| 2015/0272884 A1 | 10/2015 | Irvine et al. |
| 2015/0328333 A1 | 11/2015 | Fraser et al. |
| 2015/0335679 A1 | 11/2015 | Chiriva-Internati |
| 2015/0335762 A1 | 11/2015 | Fraser et al. |
| 2015/0359853 A1 | 12/2015 | Felber et al. |
| 2016/0030304 A1 | 2/2016 | Nagamatsu et al. |
| 2016/0038415 A1 | 2/2016 | Irvine et al. |
| 2016/0051698 A1 | 2/2016 | Schneck et al. |
| 2016/0068584 A1 | 3/2016 | Bechard et al. |
| 2016/0130318 A1 | 5/2016 | Jacques et al. |
| 2016/0175397 A1 | 6/2016 | Umana et al. |
| 2016/0256386 A1 | 9/2016 | Irvine et al. |

(56) References Cited

U.S. PATENT DOCUMENTS

| | | |
|---|---|---|
| 2016/0303046 A1 | 10/2016 | Irvine et al. |
| 2016/0375149 A1 | 12/2016 | Irvine et al. |
| 2017/0020963 A1 | 1/2017 | Qu et al. |
| 2017/0042998 A1 | 2/2017 | Slanetz |
| 2017/0049882 A1 | 2/2017 | Irvine et al. |
| 2017/0065726 A1 | 3/2017 | Huang |
| 2017/0080104 A1 | 3/2017 | Irvine et al. |
| 2017/0088597 A1 | 3/2017 | Wong et al. |
| 2017/0151281 A1 | 6/2017 | Wagner et al. |
| 2017/0196938 A1 | 7/2017 | Tang et al. |
| 2017/0216218 A1 | 8/2017 | Farokhzad et al. |
| 2017/0246253 A1 | 8/2017 | McCauley |
| 2017/0266114 A1 | 9/2017 | Irvine et al. |
| 2017/0333571 A1 | 11/2017 | Bhargava et al. |
| 2017/0335281 A1 | 11/2017 | Loew et al. |
| 2017/0342119 A1 | 11/2017 | Liu et al. |
| 2017/0349875 A1 | 12/2017 | Coelho et al. |
| 2018/0044391 A1 | 2/2018 | Gundram et al. |
| 2018/0110733 A1 | 4/2018 | Irvine et al. |
| 2018/0185473 A1 | 7/2018 | Irvine et al. |
| 2019/0083576 A1 | 3/2019 | Tang et al. |
| 2020/0360482 A1 | 11/2020 | Tang et al. |
| 2021/0060065 A1 | 3/2021 | Andresen |
| 2021/0259968 A1 | 8/2021 | Irvine et al. |
| 2021/0269500 A1 | 9/2021 | Irvine et al. |
| 2022/0008526 A1 | 1/2022 | Andresen et al. |

FOREIGN PATENT DOCUMENTS

| | | |
|---|---|---|
| EP | 831860 B1 | 10/2004 |
| EP | 1777294 A1 | 4/2007 |
| EP | 2025746 A1 | 2/2009 |
| EP | 2286831 A1 | 2/2011 |
| EP | 2388266 B1 | 11/2011 |
| EP | 2470644 B1 | 7/2012 |
| EP | 2537933 A1 | 12/2012 |
| EP | 2915569 A1 | 9/2015 |
| EP | 2956544 B1 | 12/2015 |
| EP | 3064507 A1 | 9/2016 |
| EP | 3235830 A1 | 10/2017 |
| JP | H3-244601 A | 10/1991 |
| JP | 2009149526 A | 7/2009 |
| JP | 2013173689 A | 9/2013 |
| WO | WO-1999042564 A2 | 8/1999 |
| WO | WO-2000000587 A1 | 1/2000 |
| WO | WO-2004032970 A2 | 4/2004 |
| WO | WO-2004035622 A2 | 4/2004 |
| WO | WO-2005044303 A1 | 5/2005 |
| WO | WO-2005079581 A1 | 9/2005 |
| WO | WO-2007001677 A2 | 1/2007 |
| WO | WO-2007034479 A2 | 3/2007 |
| WO | WO-2007046006 A2 | 4/2007 |
| WO | WO-2010059253 A2 | 5/2010 |
| WO | WO-2010104865 A2 | 9/2010 |
| WO | WO-2010147655 A2 | 12/2010 |
| WO | WO-2011017151 A2 | 2/2011 |
| WO | WO-2011063156 A2 | 5/2011 |
| WO | WO-2012040323 A2 | 3/2012 |
| WO | WO-2012112689 A1 | 8/2012 |
| WO | WO-2012142410 A2 | 10/2012 |
| WO | WO-2014204762 A1 | 12/2014 |
| WO | WO-2015018528 A1 | 2/2015 |
| WO | WO-2015018529 A1 | 2/2015 |
| WO | WO-2015024666 A1 | 2/2015 |
| WO | WO-2015048498 A2 | 4/2015 |
| WO | WO-2015120421 A1 | 8/2015 |
| WO | WO-2015131994 A1 | 9/2015 |
| WO | WO-2015153753 A2 | 10/2015 |
| WO | WO-2015176662 A1 | 11/2015 |
| WO | WO-2015189357 A1 | 12/2015 |
| WO | WO-2015188141 A9 | 1/2016 |
| WO | WO-2016018920 A1 | 2/2016 |
| WO | WO-2016105542 A2 | 6/2016 |
| WO | WO-2016142314 A1 | 9/2016 |
| WO | WO-2016145317 A1 | 9/2016 |
| WO | WO-2016146035 A1 | 9/2016 |
| WO | WO-2016154508 A1 | 9/2016 |
| WO | WO-2016154625 A1 | 9/2016 |
| WO | WO-2017027843 A1 | 2/2017 |
| WO | WO-2017046200 A1 | 3/2017 |
| WO | WO-2017087857 A1 | 5/2017 |
| WO | WO-2018075989 A1 | 4/2018 |
| WO | WO-2019050978 A1 | 3/2019 |
| WO | WO-2020102745 A1 | 5/2020 |
| WO | WO-2020205808 A1 | 10/2020 |

OTHER PUBLICATIONS

U.S. Appl. No. 17/293,995, filed May 14, 2021, Andresen et al.
U.S. Appl. No. 17/599,948, filed Sep. 29, 2021, Jones.
International Search Report in International Application No. PCT/US2017/037249 dated Sep. 19, 2017.
Written Opinion of the International Search Authority in International Application No. PCT/US2017/037249 dated Sep. 19, 2017.
McInnis et al., "A Fully Closed, High Efficiency Manufacturing Technology Platform for the Production of T Cell Therapies Targeting Multiple Tumor Antigens," Society for Immunotherapy for Cancer (SITC) 33rd Annual Meeting. Nov. 10, 2018.
Han et al., "IL-15:IL-15 receptor alpha superagonist complex: High-Level Co-expression in Recombinant Mammalian Cells, Purification and Characterization," Cytokine 56(3):804-810 (2011).
Hong et al., "Configuration-dependent Presentation of Multivalent IL-15:IL-15Rα Enhances the Antigen-Specific T Cell Response and Anti-tumor Immunity," J. Biol. Chem. 291(17):(2016) (18 pages).
Kim et al., "IL-15 Superagonist /IL-15RαSushi-Fc fusion complex (IL-15SA/IL-15αSu-Fc; ALT-803) markedly enhances specific subpopulations of NK and memory CD8+ T cells, and mediates potent anti-tumor activity against murine breast and colon carcinomas," Oncotarget 7(13):16130-16145 (2016).
Van Ostaijen-ten Dam et al., "Preparation of Cytokine-activated NK Cells for Use in Adoptive Cell Therapy in Cancer Patients: Protocol Optimization and Therapeutic Potential," J. Immunother. 39:90-100 (2016).
Tanna et al., "Critical Testing and Parameters for Consideration When Manufacturing and Evaluating Tumor-Associated Antigen-Specific T Cells," Cytotherapy 21(3):278-288 (2019).
Bernard et al., "Identification of an Interleukin-15α Receptor-Binding Site on Human Interleukin-15," J. Biol. Chem. 279(23):24313-24322 (2004).
Carson et al., "Interleukin (IL) 15 is a novel cytokine that activates human natural killer cells via components of the IL-2 receptor," J. Exp. Med. 180(4):1395-1403 (1994).
Cosman et al., "Interleukin 15 and its Receptor," Ciba. Found. Symp. 195:221-233 (1995).
Giri et al., "Utilization of the β and γ Chains of the IL-2 Receptor by the Novel Cytokine IL-15," EMBO J. 13(12):2822-2830 (1994).
Giri et al., "Identification and Cloning of a Novel IL-15 Binding Protein that is Structurally Related to the α Chain of the IL-2 Receptor," EMBO J. 14(15):3654-3663 (1995).
Grabstein et al., "Cloning of a T Cell Growth Factor that Interacts with the β Chain of the Interleukin-2 Receptor," Science 264(5161):965-968 (1994).
Mortier et al., "Soluble Interleukin-15 Receptor α (IL-15Rα)-sushi as a Selective and Potent Agonist of IL-15 Action through IL-15Rβ/γ; Hyperagonist IL-15.IL-15Rα Fusion Proteins," J. Biol. Chem. 281(3):1612-1619 (2006).
Rubinstein et al., "Converting IL-15 to a Superagonist by Binding to Soluble IL-15Rα," PNAS 103(24):9166-9171 (2006).
Stoklasek et al., "Combined IL-15/IL-15Rα Immunotherapy Maximizes IL-15 Activity in vitro," J. Immunol. 177:6072-6080 (2006).
Wei et al., "The Sushi Domain of Soluble IL-15 Receptor α Is Essential for Binding IL-15 and Inhibiting Inflammatory and Allogenic Responses In Vitro and In Vivo," J. Immunol. 167:277-282 (2001).
Guo et al., "Immunobiology of the IL-15/IL-15Rα Complex as an Antitumor and Antiviral Agent," Cytokine Growth Factor Revs. 38 (2017) (45 pages).
Hurton et al., "Tethered IL-15 Augments Antitumor Activity and Promotes a Stem-Cell Memory Subset in Tumor-specific T cells," PNAS 113(48):E7788-E7797 (2016).

(56) References Cited

OTHER PUBLICATIONS

Perdreau et al., "Different Dynamics of IL-15R Activation Following IL-15 cis- or trans-Presentation," Eur. Cytokine Netw. 21(4):297-307 (2010).
Stonier et al., "Trans-presentation: A Novel Mechanism Regulating IL-15 Delivery and Responses," Immunol. Lett. 127(2) (2010) (16 pages).
Akagi et al., "Development of vaccine adjuvants using polymeric nanoparticles and their potential applications for anti-HIV vaccine," Yakugaku Zasshi, vol. 127(2):307-317 (2007).
Akin et al., Bacteria-mediated delivery of nanoparticles and cargo into cells. Nat Nanotechnol., vol. 2(7):441-9 (2007).
Allen, T. et al., "Anti-CD19-Targeted Liposomal Doxorubicin Improves the Therapeutic Efficacy in Murine B-Cell Lymphoma and Ameliorates the Toxicity of Liposomes with Varying Drug Release Rates," Clin Cancer Res., vol. 11(9):3567-3573 (2005).
Allen, T. et al., "Drug Delivery Systems: Entering the Mainstream. Science," vol. 303(5665): 1818-1822 (2004).
Alving, C., "Liposomes as carriers of antigens and adjuvants," J Immunol Methods., vol. 140(1):1-13 (1991).
Alving,C. "Lipopolysaccharide, Lipid A, and Liposomes Containing Lipid A as Immunologic Adjuvants," Immunobiology, vol. 187(3-5):430-446 (1993).
Babensee, J. et al., "Differential levels of dendritic cell maturation on different biomaterials used in combination products," J Biomed Mater Res A., vol. 74(4):503-510. (2005).
Bal et al., "Efficient induction of immune responses through intradermal vaccination with N-trimethyl chitosan containing antigen formulations," J Control Release, vol. 142(3):374-83 (2010).
Barral, P. et al., "B cell receptor-mediated uptake of CD1d-restricted antigen augments antibody responses by recruiting invariant NKT cell help in vivo," Proc Natl Acad Sci USA, vol. 105(24):8345-8350 (2008).
Baudino, L. et al., "Crucial Role of Aspartic Acid at Position 265 in the CH2 domain for murine IgG2a and IgG2b Fc-Associated effector functions," J Immunol., vol. 181(9):6664-6669 (2008).
Beisiegel, U. et al., "The LDL-receptor-related protein, LRP, is an apolipoprotein E-binding protein," Nature, vol. 341(6328):162-164 (1989).
Bennewitz, N.et al., "The effect of the physical form of poly(lactic-co-glycolic acid) carriers on the humoral immune response to co-delivered antigen," Biomaterials, vol. (16):2991-2999 (2005).
Bershteyn et al., "Versatile lipid-based vaccine carriers elicit CTL and antibody responses to surface-conjugated or encapsulated antigen," Keystone Symposium. Poster Presentation, A44. 1 page.
Bershteyn, A. et al., "Polymer-supported lipid shells, onions, and flowers," Soft Matter, vol. 4(9):1787-1791 (2008).
Bershteyn, A.et al. "Lipid-Coated Nano-and Microparticles for Vaccine Design," Materials Research Society fall meeting, 7 pages (2009).
Bershteyn, A.et al., "Robust IgG responses to nanograms of antigen using a biomimetic lipid-coated particle vaccine," J Control Release, vol. 157(3):354-65 (2012).
Besser, M. et al., "Clinical responses in a phase II study using adoptive transfer of short-term cultured tumor infiltration lymphocytes in metastatic melanoma patients," Clin Cancer Res, vol. 16(9):2646-2655 (2010).
Bhowmick, S. et al., "Comparison of liposome based antigen delivery systems for protection against Leishmania donovani," J Controlled Release, vol. 141(2):199-207 (2010).
Bottini, "Luminescent Silica Nanobeads: Characterization and Evaluation as Efficient Cytoplasmatic Transporters for T-Lymphocytes," JACS, vol. 129(25) pp. 7814-7823 (2007).
Brocchini, S. et al. "Disulfide bridge based PEGylation of proteins," Advanced Drug Delivery Reviews, vol. 60: 3-12 (2008).
Cai, Z. et al., "Encapsulated enhanced green fluorescence protein in silica nanoparticle for cellular imaging," Nanoscale, vol. 3(5):1974-1976 (2011).
Cashion, M. et al., "Biomimetic Design and Performance of Polymerizable Lipids," Accounts Chem. Res., vol. 42(8):1016-1025 (2009).

Chacon, M. et al., "Optimized preparation of poly d,I (lactic-glycolic) microspheres and nanoparticles for oral administration," Int J Pharm., vol. 141(1-2):81-91 (1996).
Chambers, E. et al., "Long Circulating Nanoparticles via Adhesion on Red Blood Cells: Mechanism and Extended Circulation," Exp Biol Med (Maywood), vol. 232(7):958-966 (2007).
Chambers, E. et al., "Prolonged circulation of large polymeric nanoparticles by non-covalent adsorption on erythrocytes," J Control Release, vol. 100(1): 111-119 (2004).
Chen, L. et al., "Characterization of PLGA microspheres for the controlled delivery of IL-1a for tumor immunotherapy," J Controlled Rel., vol. 43:261-272 (1997).
Chirifu, M. et al., "Crystal Structure of the IL-15-IL-15 Ralpha complex, a cytokine-receptor unit presented in trans," Nature Immunology, Published online Jul. 22, 2007, pp. 1001-1007 (2007).
Cho, E. et al., "Understanding the Role of Surface Charges in Cellular Adsorption versus Internalization by Selectively Removing Gold Nanoparticles on the Cell Surface with a I-2/KI Etchant," Nano Lett., vol. 9(3):1080-1084 (2009) (17 pages).
Clemente-Casares, X. et al., "Peptide-MHC-based nanovaccines for the treatment of autoimmunity: a "one size fits all" approach?" J Mol Med., vol. 89(8):733-742 (2011).
Cole, C. et al., "Tumor-targeted, systemic delivery of therapeutic viral vectors using hitchhiking on antigen-specific T cells," Nat Med., vol. 11(10):1073-1081 (2005).
Collins, D. et al., "Processing of exogenous liposome-encapsulated antigens in vivo generates class I MHC-restricted T cell responses," J Immunol., vol. 148(11):3336-3341 (1992).
Coronoa-Ortega, T. et al., "Characterization of cationic liposomes having IL-2 expressed on their external surface, and their affinity to cervical cancer cells expressing the IL-2 receptor," Journal of Drug Testing, vol. 17(7):496-501 (2009).
Davis, M. et al., "Nanoparticle therapeutics: an emerging treatment modality for cancer," Nat Rev Drug Discov., 7(9):771-782 (2008).
De La Pena, H. et al., "Artificial exosomes as tools for basic and clinical immunology," J. Immunol. Methods, vol. 344(2):121-132(2009).
Demento, S. et al., "Inflammasome-activating nanoparticles as modular systems for optimizing vaccine efficacy," Vaccine, vol. 27(23):3013-3021 (2009) (17 pages).
Dinauer, N. et al., "Selective targeting of antibody-conjugated nanoparticles to leukemic cells and primary T-lymphocytes," Biomaterials, vol. 26(29):5898-5906 (2005).
Ding H. et al., "Bioconjugated PLGA-4-arm-PEG branched polymeric nanoparticles as novel tumor targeting carriers," Nanotechnology, vol. 22(16) (2011) (12 pages).
Diwan et al., Dose sparing of CpG oligodeoxynucleotide vaccine adjuvants by nanoparticle delivery. Curr Drug Deliv., 1(4):405-412 (2004).
Dou, H. et al., "Development of a macrophage-based nanoparticle platform for antiretroviral drug delivery," Blood, vol. 108(8):2827-2835 (2006).
Drummond, D. et al., "Optimizing Liposomes for Delivery of Chemotherapeutic Agents to solid tumors," Pharmacol Rev., vol. 51(4):691-743 (1991).
Dubikovskaya, E. et al., "Overcoming multidrug resistance of small-molecule therapeutics through conjugation with releasable octaarginine transporters," PNAS USA, vol. 105(34):12128-12133 (2008).
Dudley, M. et al., "Cancer Regression and Autoimmunity in Patients after Clonal Repopulation with Antitumor Lymphocytes," Science, vol. 298(5594):850-854 (2002) (10 pages).
Dudley, M. et al., "A phase I study of nonmyeloablative chemotherapy and adoptive transfer of autologous tumor antigen-specific T lymphocytes in patients with metastatic melanoma," J. Immunother., vol. 25(3):243-251 (2002) (17 pages).
Eck, W. et al., "Anti-CD4-targeted gold nanoparticles induce specific contrast enhancement of peripheral lymph nodes in X-ray computed tomography of live mice," Nano Lett., vol. 10(7):2318-2322 (2010).

(56) References Cited

OTHER PUBLICATIONS

Edwards, B. et al., "The Remarkable Flexibility of the Human Antibody Repertoire Isolation of Over One Thousand Different Antibodies to a Single Protein, BLyS," J Mol Biol., vol. 334(1):103-118 (2003).
Elamanchili, P. et al., "Characterization of poly(D,L-lactic-co-glycolic acid) based nanoparticulate system for enhanced delivery of antigens to dendritic cells," Vaccine, vol. 22(19):2406-2412(2004).
Endsley, A. et al., "Enhanced anti-HIV Efficacy of Indinavir after inclusion in CD4-targeted lipid nanoparticles," J Acquir Immune Defic Syndr., vol. 61(4):417-424 (2012).
Fahmy, T. et al., "A nanoscopic multivalent antigen-presenting carrier for sensitive detection and drug delivery to T cells," Nanomedicine, vol. 3(1):75-85 (2007).
Fahmy, T. et al., "Nanosystems for simultaneous imaging and drug delivery to T cells," AAPS J., vol. 9(2):E171-E180 (2007).
Fifis, T. et al., "Size-Dependent Immunogenicity: Therapeutic and protective properties of nano-vaccines against tumors," J Immunol., vol. 173(5):3148-3154 (2004).
Fischer, H. et al., "Nanotoxicity: the growing need for in vivo study," Current Opin Biotechnol., vol. 18(6):565-571 (2007).
Friede, M. et al., "Induction of immune response against a short synthetic peptide antigen coupled to small neutral liposomes containing monophosphoryl lipid A," Mol Immunol., vol. 30(6):539-547 (1993).
Gabizon, A. et al., "Prolonged circulation time and enhanced accumulation in malignant exudates of doxorubicin encapsulated in polyethylene-glycol coated liposomes," Cancer Res., vol. 54(4):987-992 (1994).
Gao, W. et al., "Treg versus Th17 lymphocyte lineages are cross-regulated by LIF versus IL-6," Cell Cycle, vol. 8(9):1444-1450 (2009) (17 pages).
Gao, X. et al., "Lectin-conjugated PEG-PLA nanoparticles: preparation and brain delivery after intranasal administration," Biomaterials, vol. 27(18):3482-3490 (2006).
Garinot, M. et al., "PEGylated PLGA-based nanoparticles targeting M cells for oral vaccination," J Control Release, vol. 120(3):195-204 (2007).
Green, J. et al., "Combinatorial Modification of Degradable Polymers Enables Transfection of Human Cells Comparable to Adenovirus," Advanced Materials, vol. 19(19):2836-2842 (2007).
Gregoriadis, G. et al., "Liposomes as immunological adjuvants and vaccine carriers," J Control Release, vol. 41 (1-2):49-56 (1996).
Gunn, J. et al., "A Multimodal Targeting Nanoparticle for Selectively Labeling T Cells," Small, vol. 4(6):712-715 (2008) (10 pages).
Hamdy, S. et al., "Enhanced antigen-specific primary CD4+ and CD8+ responses by codelivery of ovalbumin and toll-like receptor ligand monophosphoryl lipid A in poly(D,L-lactic-co-glycolic acid) nanoparticles," J Biomed Mater Res A., vol. 81(3):652-662 (2006).
Hedge, M. et al., "Tandem CAR T cells targeting HER2 and IL13Ra2 mitigate tumor antigen escape," J Clin Invest., vol. 126(8):3036-3052 (2016).
Heffernan, M. et al., "The stimulation of CD8+ T cells by dendritic cells pulsed with polyketal microparticles containing ion-paired protein antigen and poly(inosinic acid)-poly(cytidylic acid)," Biomaterials, vol. 30(5):910-918 (2009).
Heit et al., "Antigen co-encapsulated with adjuvants efficently drive protective T cell immunity," Eur J Immunol., 37(8):2063-74 (2007).
Hodi, F. et al., "Improved survival with ipilimumab in Patients with Metastatic Melanoma," N Engl. J. Med., vol. 363(8):711-723 (2010).
HORI , Y. et al., "Injectable dendritic cell-carrying alginate gels for immunization and immunotherapy," Biomaterials, vol. 29(27):3671-3682 (2008).
Hori, Y. et al., "Engulfing tumors with synthetic extracellular matrices for cancer immunotherapy," Biomaterials, vol. 30 (35):6757-6767 (2009) (20 pages).
Hotz, J. et al., "Vesicle-templated polymer hollow spheres," Langmuir, vol. 14(5):1031-1036 (1998).

Hsu, C. et al., "Cytokine-independent growth and clonal expansion of a primary human CD8+ T-cell clone following retroviral transduction with the IL-15 gene," Blood, vol. 109(12):5168-5177 (2007).
Hu, Y. et al., "Cytosolic delivery of membrane-impermeable molecules in dendritic cells using pH-responsive core-shell nanoparticles," Nano Lett., vol. 7(10):3056-3064 (2007).
Immordino, M. et al., "Stealth liposomes: review of the basic science, rationale, and clinical applications, existing and potential," Int J Nanomedicine, vol. 1(3):297-315 (2006).
Irvine et al., "Combining cell therapy with nanotechnology for enhanced cancer immunotherapy." 16th International Symposium on Recent Advances in Drug Delivery Systems. Salt Lake City, UT, Abstract (2013) (2 pages).
Irvine, D.J. "Engineering nanomaterials as vaccine adjuvants and agents for cancer immunotherapy," Seminar at Scripps Res Institute (2011) (9 pages).
Irvine, D.J. "Engineering nanoparticle delivery for vaccines and immunotherapy," Nanotechnology in Infectious Disease Meeting, Atlanta, GA (2010) (33 pages).
Jain, N.K., et al., "Targeted drug delivery to macrophages," Expert Opin Drug Deliv., vol. 10(3):353-367 (2013).
Jeong, J. et al., "Enhanced adjuvantic property of polymerized liposome as compared to a phospholipid liposome," J Biotechnol., vol. 94(3):255-263 (2002).
Jiang, W. et al., "Biodegradable poly(lactic-co-glycolic acid) microparticles for injectable delivery of vaccine antigens," Adv Drug Deliv Rev., vol. 57(3):391-410 (2005).
Johnson, RM., "The kinetics of Resealing of Washed Erythrocyte Ghosts," J. Membr. Biol., vol. 22 (3-4):231-253 (1975).
Jones, DT "Critically assessing the state-of-the-art in protein structure prediction," Pharmacogenomics Journal, vol. 1(2):126-134 (2001).
Jones, L. et al., "Releasable Luciferin-Transporter Conjugates: tools for the real-time analysis of cellular uptake and release," J Am Chern Soc., vol. 128(20):6526-6527 (2006).
June, C. "Principles of adoptive T cell cancer therapy," J Clin Invest., vol. 117(5):1204-1212 (2007).
Kaiser-Schulz, G. et al., "Polylactide-coglycolide microspheres co-encapsulating recombinant tandem prion protein with CpG-oligonucleotide break self-tolerance to prion protein in wild-type mice and induce CD4 and CD8 T cell responses," J Immunol., vol. 179(5):2797-2807 (2007).
Kalos, M. "Biomarkers in T cell therapy clinical trials," J Trans Med., vol. 9(138) (2011) (9 pages).
Kalos, M. et al., "T cells with chimeric antigen receptors have potent antitumor effects and can establish memory in patients with advanced leukemia," Sci Trans Med., vol. 3(95) (2011) (12 pages).
Kerkar, S. et al., "Tumor-specific CD8+ T cells expressing interleukin-12 eradicate established cancers in lymphodepleted hosts," Cancer Res., vol. 70(17):6725-6734 (2010).
Kirby, C. et al., "Dehydration-rehydration vesicles: a simple method for high yield drug entrapment in liposomes," Nat Biotechnol., vol. 2(11):979-984 (1984).
Kirpotin, D. et al., "Antibody targeting of long-circulating lipidic nanoparticles does not increase tumor localization but does increase internalization in animal models," Cancer Res., vol. 66(13):6732-6740 (2006).
Klebanoff, C. et al., "Sinks, suppressors and antigen presenters: how lymphodepletion enhances T cell-mediated tumor immunotherapy," Trends Immunol., vol. 26(2): 111-117 (2005) (14 pages).
Kobayashi, H. et al., "Phase I/II study of adoptive transfer of γδ T cells in combination with zoledronic acid and IL-2 to patients with advanced renal cell carcinoma," Cancer Immunol. Immunother, vol. 60(8):1075-1084 (2011).
Kochenderfer, J. et al., "Adoptive transfer of syngeneic T cells transduced with a chimeric antigen receptor that recognizes murine CD19 can eradicate lymphoma and normal B cells," Blood, vol. 116 (19):3875-3886 (2010).
Konigsberg, P.J. "The development of IL-2 conjugated liposomes for therapeutic purposes," Biochimica Biophysica Acta, vol. 1370(2):243-251 (1998).
Konrad, M. et al., "Pharmacokinetics of recombinant interleukin 2 in humans," Cancer Res., vol. 50(7):2009-2017 (1990).

(56) References Cited

OTHER PUBLICATIONS

Krishna, N. et al., "Genetic Determinants of Rous Sarcoma Virus Particle Size," Journal of Virology, vol. 72 (1):564-577 (1998).
Kudchodkar, S. et al., "Improving CAR T Cell Efficacy for Solid Tumors By Nanogel-Based Delivery of Immunomodulatory Proteins," Molecular Therapy: The Journal of The American Society of Gene Therapy, vol. 23(SI):S207-S207 (2015) (1 page).
Kwon et al., In vivo targeting of dendritic cells for activation of cellular immunity using vaccine carriers based on pH-responsive microparticles. Proc Natl Acad Sci USA., 102(51):18264-8 (2005).
Kwong, B. et al., "Localized immunotherapy via liposome-anchored Anti-CD137+IL-2 prevents lethal toxicity and elicits local and systemic antitumor immunity," Cancer Res., vol. 73(5):1547-1558 (2013).
Kwong, B. et al., "Induction of potent anti-tumor responses while eliminating systemic side effects via liposome-anchored combinatorial immunotherapy," Biomaterials, vol. 32(22):5134-5147 (2011).
Kwong, B., "Liposome-anchored local delivery of immunomodulatory agents for tumor therapy," Biological Engineering, Massachusetts Institute of Technology, 175 pages (2012).
Lachman, L. et al., "Cytokine-containing liposomes as vaccine adjuvants," Eur Cytokine Netw., vol. 7(4):693-698 (1996).
Lateef, S. et al., "An Improved Protocol for Coupling Synthetic Peptides to Carrier Proteins for Antibody Production using DMF to Solubilize Peptides," J Biomolecular Techniques, vol. 18:173-176 (2007).
Lavelle, E.C. et al., "The stability and immunogenicity of a protein antigen encapsulated in biodegradable microparticles based on blends of lactide polymers and polyethylene glycol.," Vaccine, vol. 17(6):512-529 (1999).
Lee, J. et al., "Multifunctional nanoarchitectures from DNA-based ABC monomers," Nat Nanotechnol. vol. 4(7):430-436 (2009) (8 pages).
Leland, P. et al., "Cancer Chemotherpay-Ribonucleases to the Rescue," Chem Biol. vol. 8(5):405-413 (2001) (16 pages).
Li, J. et al., "Purification of melanoma reactive T cell by using a monocyte-based solid phase T-cell selection system for adoptive therapy," J Immunother., vol. 31(1):81-88 (2008).
Li, Y. et al., "PEGylated PLGA nanoparticles as protein carriers: synthesis, preparation and biodistribution in rats," J Control Release, vol. 71(2):203-211 (2001).
Lloyd, C. et al., "Modelling the human immune response: performance of a 1011 human antibody repertoire against a broad panel of therapeutically relevant antigens," Protein Engineering, Design & Selection, vol. 22(3):159-168 (2009).
Lodish, H. et al., "Chemical Foundations," In: Molecular Cell Biology, Fifth Eds. Chapter 2 (2004) (19 pages).
Lowenthal, J. et al., "Similarities between interleukin-2 receptor number and affinity on activated B and T lymphocytes," Nature, vol. 315(20):669-672 (1985).
Lowenthal, J. et al., "High and low affinity IL 2 receptors: analysis by IL 2 dissociation rate and reactivity with monoclonal anti-receptor antibody PC61," J Immunol., vol. 135(6):3988-3994 (1985).
Lu, W. et al., "Cationic albumin-conjugated pegylated nanoparticles as novel drug carrier for brain delivery," J Control Release, vol. 107(3):428-448 (2005).
Lutsiak, M. et al., "Analysis of poly(D,L-lactic-co-glycolic acid) nanosphere uptake by human dendritic cells and macrophages in vitro," Pharm Res., vol. 19(10):1480-1487 (2002).
Maclaughlin, C.M., et al., "Polymer-coated surface enhanced Raman scattering (SERS) gold nanoparticles for multiplexed labeling of chronic lymphocytic leukemia cells," Frontiers in Biological Detection: From Nanosensors to Systems IV, SPIE, vol. 8212(1):1-11 (2012).
Maeda, H. et al., "Tumor vascular permeability and the EPR effect in macromolecular therapeutics: a review.," J Control Release, vol. 65(1-2):271-284 (2000).
Maloy, K. et al., "Induction of mucosal and systemic immune responses by immunization with ovalbumin entrapped in poly(lactide-co-glycolide) microparticles," Immunology, vol. 81(4):661-667 (1994).
Markley, J. et al., "IL-7 and IL-21 are superior to IL-2 and IL-15 in promoting human T cell-mediated rejection of systemic lymphoma in immunodeficient mice," Blood, vol. 115(17):3508-3519 (2010).
Martinez Gomez, J. et al., "A protective allergy vaccine based on CpG-and protamine-containing PLGA microparticles," Pharm Res., vol. 24(10):1927-1935 (2007).
Matsumoto, N. et al., "Synthesis of Nanogel-Protein Conjugates," Polym Chem., vol. 4(8):2464-2469 (2013) (15 pages).
Matsumura, Y. et al., "A new concept for macromolecular therapeutics in cancer chemotherapy: mechanism of tumoritropic accumulation of proteins and the antitumor agent smancs," Cancer Res., vol. 46(12 Pt 1):6387-6392 (1986).
Mckee, A. et al., "How do adjuvants work? Important considerations for new generation adjuvants," Immunity, vol. 27(5):687-690 (2007).
Mellman, I. et al., "Cancer immunotherapy comes of age," Nature, vol. 480(7378):480-489 (2011).
Meng, F. et al., "Reduction-sensitive polymers and bioconjugates for biomedical applications," Biomaterials, vol. 30:2180-2198 (2009) (15 pages).
Minami, Y. et al., "The IL-2 receptor complex: its structure, function, and target genes," Annu Rev. Immunol., vol. 11:245-268 (1993).
Moghimi, S. et al., "Long-circulating and target-specific nanoparticles: theory to practice," Pharmacol Rev., vol. 53(2):283-318 (2001).
Mohammed, A. et al., "Lyophilisation and sterilisation of liposomal vaccines to produce stable and sterile products," Methods, vol. 40(1):30-38 (2006).
Moon, J. et al., "Engineering nano-and microparticles to tune immunity," Adv Mater., vol. 24(28):3724-3746 (2012) (39 pages).
Moon, J. et al., "Enhancing humoral responses to a malaria antigen with nanoparticle vaccines that expand $T_{fh}$ cells and promote germinal center induction," Proc Natl Acad Sci USA., vol. 109(4):1080-1085 (2012).
Moon, J. et al., "Interbilayer-crosslinked multilamellar vesicles as synthetic vaccines for potent humoral and cellular immune responses," Nat Mater., vol. 10(3):243-251 (2011).
Moore, A. et al., "Tracking the recruitment of diabetogenic CD8+ T-cells to the pancreas in real time," Diabetes, vol. 53(6):1459-1466 (2004).
Morgan, R. et al., "Cancer regression in patients after transfer of genetically engineered lymphocytes," Science, vol. 314(5796):126-129 (2006) (10 pages).
Mortensen, M.W. et al., "Next generation adoptive immunotherapy—human T cells as carriers of therapeutic nanoparticles," J Nanosci Nanotechnol., vol. 7(12):4575-4580 (2007).
Mundargi, R. et al., "Nano/micro technologies for delivering macromolecular therapeutics using poly(D,L-lactide-co-glycolide) and its derivatives," J Control Release., vol. 125(3):193-209 (2008).
Murcia et al., "Design of quantum dot-conjugated lipids for long-term, high-speed tracking experiments on cell surfaces," J Am Chem Soc., vol. 130(45): 15054-62 (2008) (21 pages).
Murphy, R. et al., "Endosome pH measured in single cells by dual fluorescence flow cytometry: rapid acidification of insulin to pH 6," J Cell Biol., vol. 98(5):1757-1762 (1984).
Nguyen, D.et al., "Disulfide-crosslinked heparin-pluronic nanogels as a redox-sensitive nanocarrier for intracellular protein deliver," J. Bioactive and Compatible Polymers, vol. 26(3):287-300 (2011).
O'Hagan, D. et al., "Induction of potent immune responses by cationic microparticles with adsorbed human immunodeficiency virus DNA vaccines," J Virol., vol. 75(19):9037-9043 (2001).
O'Hagan, D. et al., "Microparticles as potentially orally active immunological adjuvants," Vaccine, vol. 7(5):421-424 (1989).
O'Hagan, D. et al., "Microparticles as vaccine adjuvants and delivery systems," Expert Rev Vaccines, vol. 2(2):269-283 (2003).
O'Hagan, D. et al., "Poly(lactide-co-glycolide) microparticles for the development of single-dose controlled-release vaccines," Adv Drug Deliv. Rev., vol. 32(3):225-246 (1987).
Overwijk, W. et al.,"Tumor regression and autoimmunity after reversal of a functionally tolerant state of self-reactive CD8+ T cells," J Exp Med., vol. 198(4):569-580 (2003).

(56) References Cited

OTHER PUBLICATIONS

Owens, D. et al., "Opsonization, biodistribution, and pharmacokinetics of polymeric nanoparticles.," Int J Pharm., vol. 307(1):93-102 (2006).
Park, J. et al., "Anti-HER2 immunoliposomes:enhanced efficacy attributable to targeted delivery," Clin Cancer Res., vol. 8(4):1172-1181 (2002).
Park, J. et al., "Modulation of CD4+ T lymphocyte lineage outcomes with targeted, nanoparticle-mediated cytokine delivery," Mol Pharm., vol. 8(1):143-152 (2011) (16 pages).
Paulos, C. et al., "Toll-like receptors in tumor immunotherapy," Clin Cancer Res., vol. 13(18 Pt 1):5280-5289 (2007).
Perche, F. et al., "Recent trends in multifunctional liposomal nanocarriers for enhanced tumor targeting," J Drug Deliv., vol. 2013, Article ID. 705265, 32 pages (2013).
Perica, K. et al., "Magnetic field-induced T cell receptor clustering by nanoparticles enhances T cell activation and stimulates antitumor activity," ACS Nano., vol. 8(3):2252-2260 (2013).
Petros, R. et al., "Strategies in the design of nanoparticles for therapeutic applications," Nature Reviews, vol. 9:615-627 (2010).
Phillips, N.et al., "Immunoliposome targeting to murine CD4+ leucocytes is dependent on immune status," J Immunol., vol. 152(6):3168-3174 (1993).
Plunkett, K. et al., "Chymotrypsin Responsive Hydrogel: Application of a Disulfide Exchange Protocol for the Preparation of Methacrylamide Containing Peptides," Biomacromolecules, vol. 6(2):632-637 (2005).
Popescu, M. et al., "A novel proteoliposomal vaccine elicits potent antitumor immunity in mice," Blood, vol. 109(12):5407-5410 (2007).
Press, O. et al., "Retention of B-Cell-Specific Monoclonal Antibodies by Human Lymphoma Cells," Blood, vol. 83(5):1390-1397 (1994).
Prieto, P. et al., "Enrichment of CD8+ cells from melanoma tumor-infiltrating lymphocyte cultures reveals tumor reactivity for use in adoptive cell therapy," J Immunother., vol. 33(5):547-556 (2010).
Prokop, A. et al., "Hydrogel-based colloidal polymeric system for protein and drug delivery: physical and chemical characterization, permeability control and applications," Advances in Polymer Science, vol. 160:119-173 (2002).
Puri, A. et al., "HER2-specific affibody-conjugated thermosensitive liposomes (Affisomes) for improved delivery of anticancer agents," J Liposome Res., vol. 18(4):293-307 (2008) (20 pages).
Qiao, J. et al., "Purging metastases in lymphoid organs using a combination of antigen-nonspecific adoptive T cell therapy, oncolytic virotherapy and immunotherapy," Nat Med, vol. 14(1):37-44 (2008).
Rangel-Corona, R. et al., "Cationic liposomes bearing IL-2 on their external surface induced mice leukocytes to kill human cervical cancer cells in vitro, and significantly reduced tumor burden in immunodepressed mice," J Drug Target., vol. 19(2):79-85 (2011).
Reddy, R. et al., "In vivo cytotoxic T lymphocyte induction with soluble proteins administered in liposomes," J Immunol., vol. 148(5):1585-1589 (1992).
Reddy, S. et al., "Exploiting lymphatic transport and complement activation in nanoparticle vaccines," Nature Biotechnology, vol. 25(10):1159-1164 (2007).
Reed, S. et al., "New horizons in adjuvants for vaccine development," Trends Immunol., vol. 30(1):23-32 (2009).
Restifo, N. et al., "Adoptive immunotherapy for cancer: harnessing the T cell response," Nat Rev. Immunol., vol. 12(4):269-281(2012).
Ring, A. et al., "Mechanistic and structural insight into the functional dichotomy between IL-2 and IL-15," Nature Immunology, vol. 13(12):1187-1197 (2012).
Rosenberg, S. et al., "Adoptive cell transfer: a clinical path to effective cancer immunotherapy," Nat Rev Cancer, vol. 8(4):299-308 (2008) (22 pages).
Rubin, B. et al., "Fractionation of T cell subsets on Ig anti-Ig columns: Isolation of helper T cells from nonresponder mice, demonstration of antigen-specific T suppressor cells, and selection of CD-3 negative variants of Jurkat T cells," Cellular Immunology, vol. 119(2):327-340. (1989).
Rubinstein, M. et al., "Ex vivo IL-12-priming during CD8+ T cell activation dramatically improves adoptive T cell transfer anti-tumor efficacy in a lymphodepleted host," J Am Coll Surg., vol. 214(4):700-707 (2012) (13 pages).
Schlosser et al., "TLR ligands and antigen need to be coencapsulated into the same biodegradable microsphere for the generation of potent cytotoxic T lymphocyte responses," Vaccine, vol. 26(13):1626-1637 (2008).
Scott, E. et al., "Protein adsorption and cell adhesion on nanoscale bioactive coatings formed from poly(ethylene glycol) and albumin microgels," Biomaterials, vol. 29(34):4481-4493 (2008).
Seeman, P. et al., "Transient Holes in the Erythrocyte Membrane During Hypotonic Hemolysis and Stable Holes in the Membrane After Lysis By Saponin and Lysolecithin," The Rockefeller University, J Cell Biol., vol. 32(1):55-70 (1967).
Shi et al., "Dendrimer-functionalized shell-crosslinked iron oxide nanoparticles for in-vivo magnetic resonance imaging of tumors.," Advanced Materials, vol. 20(9):1671-1678 (2008).
Shilyansky, J. et al., "T-cell receptor usage by melanoma-specific clonal and highly oligoclonal tumor-infiltrating lymphocyte lines," PNAS, vol. 91:2829-2833 (1994).
Shimizu, T. et al., "Nanogel DDS enables sustained release of IL-12 for tumor immunotherapy," BBRC, vol. 367(2):330-335 (2008).
Singh et al., "Anionic microparticles are a potent delivery system for recombinant antigens from Neisseria meningitidis serotype B," J Pharm Sci., vol. 93(2):273-282 (2003).
Singh et al., "Cationic microparticles: A potent delivery system for DNA vaccines," Proc Natl Acad Sci USA., vol. 97(2):811-816 (2007).
Singh et al., "Charged polylactide co-glycolide microparticles as antigen delivery systems," Expert Opin Biol Ther., vol. 4(4):483-491 (2004).
Singh et al., "Immunogenicity and protection in small-animal models with controlled-release tetanus toxoid microparticles as a single-dose vaccine," Infect Immun., vol. 65(5):1716-1721 (1997).
Singh et al., "Nanoparticles and microparticles as vaccine-delivery systems," Expert Rev Vaccines., vol. 6(5):797-808 (2007).
Singh et al., "Polylactide-co-glycolide microparticles with surface adsorbed antigens as vaccine delivery systems," Curr Drug Deliv., vol. 3(1):115-120 (2006).
Singh et al., "Recent advances in vaccine adjuvants," Pharm Res., vol. 19(6):715-728 (2002).
Singh, S. et al., "Embedding of Active Proteins and Living Cells in Redox-Sensitive Hydro-gels and Nanogels through Enzymatic Cross-Linking," Angew. Chem. tnt. Ed., vol. 52:3000-3003 (2013).
Society for Experimental Biology and Medicine, Nanoparticles hitchhike on red blood cells for drug delivery. RxPG News. Jun. 27, 2007. Last retrieved from http://www.rxpgnews.com/drugdelivery/Nanoparticles-hitchhike-on-red-blood-cells-a-potential-new-method-for-drug-delivery_40324.shtml (2012) (3 pages).
Steers, N. et al.,"Liposome-encapsulated HIV-1 Gag p24 containing lipid A induces effector CD4+ T-cells, memory CD8+ T-cells, and pro-inflammatory cytokines," Vaccine, vol. 27(49):6939-6949 (2009).
Steinfeld, U., et al, "T lymphocytes as potential therapeutic drug carrier for cancer treatment," Int. J. Pharm., vol. 311:229-236 (2006).
Stephan et al., "Enhancing Cell therapies from the Outside In: Cell Surface Engineering Using Synthetic Nanomaterials," Nano Today., vol. 6(3):309-325 (2011) (28 pages).
Stephan et al., "Synapse-directed delivery of immunomodulators using T-cell-conjugated nanoparticles," Biomaterials, vol. 33(23):5776-5787 (2012) (25 pages).
Stephan et al., "T cell-encoded CD80 and 4-1BBL induce auto-and transcostimulation, resulting in potent tumor rejection," Nat Med., vol. 13(12): 1440-1449 (2007).
Stephan, M. et al., "Therapeutic cell engineering with surface-conjugated synthetic nanoparticles," Nat Med., vol. 16(9):1035-1041 (2010) (17 pages).
Swiston et al., "Surface functionalization of living cells with multilayer patches," Nano Lett., vol. 8(12):4446-4453 (2008).
Takasaki et al., "Micelles as intermediates in the preparation of protein-liposome conjugates," Bioconjug Chem., vol. 17(2):438-450 (2006).

(56) References Cited

OTHER PUBLICATIONS

Tan, H. et al., "PEG-urokinase nanogels with enhanced stability and controllable bioactivity," Soft Matter, vol. 8:2644-2650 (2012).
Tang, L et al., "Abstract 2792: Engineering T lymphocytes with protein nanogels for cancer immunotherapy," Cancer Research, AACR Annual Meeting, 2 pages (2014).
Tang, L. et al., "Enhancing T cell therapy through TCR-signaling-responsive nanoparticle drug delivery," Nat Biotechnol. 36(8): 707-716 (2018) (29 pages).
Tangney, M. et al., "The use of Listeria monocytogenes as a DNA delivery vector for cancer gene therapy," Bioeng Bugs., vol. 1(4):284-287 (2010).
Topalian et al., "Expansion of human tumor infiltrating lymphocytes for use in immunotherapy trials", J Immunol Methods, 102(1):127-41 (1987).
Topalian, S. et al., "Safety, activity, and immune correlates of anti-PD-1 antibody in cancer," N Engl. J Med., vol. 366(26):2443-2454 (2012) (19 pages).
Torchilin, "Recent advances with liposomes as pharmaceutical carriers," Nat Rev Drug Disc., vol. 4(2):145-160 (2005).
Tosatto, S.C., et al., "Large-scale prediction of protein structure and function from sequence," Current Pharmaceutical Design, vol. 12:2067-2086 (2006).
Trevaskis, NL et al., "Targeted drug delivery to lymphocytes: a route to site-specific immunomodulation," Mol Pharm., vol. 7(6):2297-2309 (2010).
Tsai, S. et al., "Reversal of autoimmunity by boosting memory-like autoregulatory T cells," Immunity, vol. 32(4):568-580 (2010).
Um et al., "Enzyme-catalysed assembly of DNA hydrogel," Nat Mater., vol. 5(10):797-801 (2006).
Van Broekhoven et al., "The novel chelator lipid 3(nitrilotriacetic acid)-ditetradecylamine ($NTA_3$-DTDA) promotes stable binding of His-tagged proteins to liposomal membranes: potent anti-tumor responses induced by simultaneously targeting antigen, cytokine and costimulatory signals to T cells," Biochim Biophys Acta., vol. 1716(2):104-116 (2006).
Vancha, A. et al., "Use of polyethyleneimine polymer in cell culture as attachment factor and lipofection enhancer," BMC Biotechnology, vol. 4 (23) (2004) (12 pages).
Vangala et al., "Comparison of vesicle based antigen delivery systems for delivery of hepatitis B surface antigen," J Controlled Release, vol. 119(1):102-110 (2007).
Vasir et al., "Biodegradable nanoparticles for cytosolic delivery of therapeutics," Adv Drug Deliv Rev. vol. 59(8):718-728 (2007) (20 pages).
Verma et al., "Surface-structure-regulated cell-membrane penetration by monolayer-protected nanoparticles," Nat Mater., vol. 7(7):588-595 (2008) (15 pages).
Von Maltzahn et al., "In vivo tumor cell targeting with click nanoparticles," Bioconjug Chem., vol. 19(8):1570-1578 (2008) (15 pages).
Vonarbourg et al., "Parameters influencing the stealthiness of colloidal drug delivery systems," Biomaterials, vol. 27(24):4356-4373 (2006).
Vugmeyster Yulia et al., "Pharmacokinetic, biodistribution, and biophysical profiles of TNF nanobodies conjugated to linear or branched poly(ethylene glycol)," Bioconjugate Chemistry, vol. 23(7):1452-1462 (2012).

Wakita et al., "An indispensable role of type-1 IFNs for inducing CTL-mediated complete eradication of established tumor tissue by CpG-liposome co-encapsulated with model tumor antigen," Int Immunol., vol. 18(3):425-434 (2006).
Walter, R. et al., "Simultaneously targeting CD45 significantly increases cytotoxicity of the anti-CD33 immunoconjugate, gemtuzumab ozogamicin, against acute myeloid leukemia (AML) cells and improves survival of mice bearing human AML xenografts," Blood, vol. 111(9):4813-4816 (2008).
Wang, X. et al., "A transgene-encoded cell surface polypeptide for selection, in vivo tracking, and ablation of engineered cells," Blood, vol. 118(5):1255-1263 (2011).
Weinstein, J. et al., "Antibody-mediated targeting of liposomes, Binding to lymphocytes does not ensure incorporation of vesicle contents into the cells," Biochimica Biophys Acta., vol. 509(2):272-288 (1978).
Westwood, J.et al., "Three agonist antibodies in combination with high-dose IL-2 eradicate orthotopic kidney cancer in mice," Journal of Translational Medicine, vol. 8(42):1-8 (2010).
Westwood, J.et al., "Toll-Like Receptor Triggering and T-Cell Costimulation Induce Potent Antitumor Immunity in Mice," CCR, vol. 15(24):7624-7633 (2009).
Wilson-Welder et al., "Vaccine adjuvants: current challenges and future approaches," J Pharm Sci., vol. 98(4):1278-1316 (2008).
Xing, T. et al., "Disulfide Core Cross-Linked PEGylated Polypeptide Nanogel Prepared by a One-Step Ring Opening Copolymerization of N-Carboxyanhydrides for drug delivery," Macromolecular Journals, vol. 11:962-969 (2011).
Xu J. et al., "Rendering protein-based particles transiently insoluble for therapeutic applications," The Journal of the American Chemical Society, vol. 134 (21):8774-8777 (2012).
Yan, M. et al. "A novel intracellular protein delivery platform based on single-protein nanocapsules," Nat Nanotechnol., vol. 5(I):48-53 (2010).
Yee et al., "Adoptive T cell therapy using antigen-specific CD8+ T cell clones for the treatment of patients with metastatic melanoma: in vivo persistence, migration, and antitumor effect of transferred T cells," Proc Natl Acad Sci USA., vol. 99(25): 16168-16173 (2002).
Zauner et al., "In vitro uptake of polystyrene microspheres: effect of particle size, cell line and cell density," J Control Release, vol. 71(1):39-51 (2001).
Zhang et al., "Folate-decorated poly(lactide-co-glycolide)-vitamin E TPGS nanoparticles for targeted drug delivery," Biomaterials, vol. 28(10):1889-1899 (2007).
Zhao et al., "Directed cell migration via chemoattractants released from degradable microspheres,"Biomaterials, vol. 26(24):5048-5063 (2005).
Zheng et al., "In vivo targeting of adoptively transferred T-cells with antibody- and cytokineconjugated liposomes," J Control Release, vol. 172(2):426-435 (2013).
Zheng, "In vivo Arming of Adoptively Transferred T-cells with Drug-loaded Nanoparticles for Cancer Immunotherapy," BMES. Presentation MIT., 18 pages (2012).
Zhu et al., "Stabilization of proteins encapsulated in injectable poly (lactide-co-glycolide)," Nat Biotechnol. vol. 18(1):52-57 (1999).
Sahaf, B. et al., "Lymphocyte surface thiol levels," Proc Natl Acad Sci USA., vol. 100(7):4001-4005 (2003).

* cited by examiner

# METHODS AND COMPOSITIONS FOR PROMOTING IMMUNE CELL FUNCTION

RELATED APPLICATIONS

This application is a U.S. National Phase application under 35 U.S.C. 371 of International Application No. PCT/US2017/037249, filed Jun. 13, 2017, which claims priority to U.S. Ser. No. 62/349,473 filed Jun. 13, 2016, the contents of both of which are incorporated herein by reference in their entirety.

SEQUENCE LISTING

The ASCII text file submitted via EFS-Web, entitled "174285_011101_ST25.txt" created on Oct. 21, 2019, having a size of 24,669 bytes, is incorporated herein by reference in its entirety.

BACKGROUND OF THE INVENTION

Immune cell therapies, e.g., adoptive cell therapy (ACT), include the steps of collecting immune cells from a subject, expanding the cells, and reintroducing the cells into the same subject or a different subject. For example, ACT of donor-derived, ex-vivo expanded human cytotoxic T lymphocytes (CTLs) has emerged as a promising approach to treat cancer. Examples of ACT include cultured tumor infiltrating lymphocytes (TILs), isolated and expanded T cell clones, and genetically engineered lymphocytes (e.g., T cells) that express conventional T cell receptors or chimeric antigen receptors. The genetically engineered lymphocytes are designed to eliminate cancer cells expressing specific antigen(s) and are expanded and delivered to a patient. ACT can provide tumor specific lymphocytes (e.g., T cells) that lead to a reduction in tumor cells in a patient.

An important limitation of immune cell based therapies is the rapid decline in viability and function of immune cells ex vivo, particularly after freezing-thawing treatments. Limitations with existing protocols for isolation, storage, freezing, thawing, and/or expansion of immune cells still remain. Thus, the need exists for preserving, e.g., optimizing, the function of immune cells derived from a subject, e.g., prior to reintroduction into the same or a different subject.

SUMMARY OF THE INVENTION

The present disclosure features, at least in part, optimized methods and compositions to produce (e.g., ex vivo) nucleated cells, e.g., immune cells, having at least one conserved function (e.g., having one or more of viability, proliferation, cytotoxic activity or activation conserved). In some embodiments, disclosed herein are methods for conserving cell function, e.g., immune cell function, e.g., after one or more cycles of freezing and/or thawing, of the nucleated cell. In embodiments, disclosed herein is a method of preparing, and/or thawing, a frozen composition of nucleated cells by contacting the nucleated cells, e.g., the immune cell, with a particle, e.g., a nanoparticle, that comprises a conservation agent, e.g., nanoparticle that comprises a protein (e.g., a protein nanogel as described herein). In some embodiments, the contacting step occurs ex vivo. In certain embodiments, the immune cell is a population of immune cells obtained from a subject. In embodiments, said protein in the nanoparticle can be chosen from one or more (e.g., 2, 3, 4, 5 or more) therapeutic proteins, e.g., a cytokine molecule (e.g., an IL-2, IL-7, IL-12, IL-15, IL-18, IL-21, IL-23, IL-4, IL-1alpha, IL-1beta, IL-5, IFNgamma, TNFalpha (TNFa), IFNalpha, IFNbeta, GM-CSF, or GCSF, including variant forms thereof, e.g., mutant; complex comprising the cytokine molecule with a polypeptide, e.g., a cytokine receptor complexes; fusion or agonist forms thereof); growth factors; and other molecules, e.g., an antibody molecule or agonist ligand against a costimulatory molecule, e.g., wherein the costimulatory molecule is chosen from OX40, CD28, GITR, VISTA, CD40, CD3, or an agonist of CD137.

In embodiments, the conservation agent, e.g. a therapeutic protein, is covalently coupled, e.g., crosslinked, to the nanoparticle, e.g., via a degradable linker (e.g., disulfide linker). In some embodiments, the conservation agent remains biologically active, e.g., maintains its function as a conservation agent after at least one freeze-thaw cycle and release from the nanoparticle. The nanoparticle-treated nucleated cells can show a significantly increased function, e.g., one or more of viability, proliferation, cytotoxic activity or activation, after a freeze-thawing cycle, compared to untreated nucleated cells. Thus, the methods and compositions disclosed herein can provide a significant benefit for cellular therapy, e.g., immunotherapy.

Accordingly, in one aspect, the invention features a composition comprising a nucleated cell and a nanoparticle that comprises at least one conservation agent, e.g., a conservation agent described herein (also referred to herein as a "nucleated cell-nanoparticle complex"). In some aspects, the present disclosure provides a composition comprising a nucleated cell and at least one conservation agent, e.g., a conservation agent described herein. In one embodiment, at least part of the composition is frozen.

In other aspects, the present disclosure provides a method of making a frozen composition of nucleated cells. The method comprises: a) providing an unfrozen composition of nucleated cells described herein, e.g., a composition of nucleated cells comprising nucleated cells and a nanoparticle that comprises at least one conservation agent, e.g., a conservation agent described herein, and b) reducing the temperature of the composition sufficiently for the composition to freeze, thereby freezing the composition of nucleated cells.

In some aspects, the present disclosure provides a method of making a thawed composition of nucleated cells, comprising: a) providing a frozen composition of nucleated cells comprising nucleated cells and a nanoparticle that comprises at least one conservation agent, e.g., a conservation agent described herein; and b) warming the frozen composition of nucleated cells sufficiently to thaw the frozen composition of nucleated cells, thereby making a thawed composition of nucleated cells.

In other aspects, the disclosure provides a composition comprising: a) a conservation agent, e.g., an IL-15 complex described herein and b) poly-lysine having an average length of 10-150, 20-100, 20-80, 20-60, 20-40, or about 30 amino acids, and c) optionally further comprising a PEG molecule, e.g., a PEG molecule having a molecular weight of about 1-10, 2-8, 4-6, or about 5 kD. In some embodiments, the poly-lysine and PEG form a block copolymer. In some embodiments, the poly-lysine is coupled, e.g., covalently coupled or non-covalently coupled (e.g., by electrostatics) to the conservation agent. In some embodiments, the conservation agent forms a protein nanogel.

In some aspects, the disclosure provides a composition comprising a nucleated cell and a nanoparticle that comprises at least one conservation agent, wherein:

(a) at least part of the composition is frozen, (b) the conservation agent comprises a cytokine molecule or a costimulatory molecule, and (c) wherein:

(i) the cytokine molecule is chosen from IL15, IL2, IL6, IL7, IL12, IL17, IL18, IL21, IL-23, IL-4, IL1alpha, IL1beta, IL-5, IFNgamma, TNFa, IFNalpha, IFNbeta, GM-CSF, or GCSF; or (ii) the costimulatory molecule is chosen from an, OX40, CD28, GITR, VISTA, CD40, CD3, or an agonist of CD137.

In embodiments, upon thawing of the composition, the conservation agent improves one or more of viability, proliferation, cytotoxic activity or activation of the nucleated cell compared to a nucleated cell in the absence of the nanoparticle.

In some aspects, the disclosure provides a composition comprising a nucleated cell and a nanoparticle that comprises at least one conservation agent, wherein:

(a) at least part of the composition is frozen; and (b) the conservation agent comprises an IL-15 molecule complexed with a polypeptide comprising:

a first domain comprising the amino acid sequence of SEQ ID NO: 7 or SEQ ID NO: 8, or an amino acid sequence having at least 85%, 90%, 95%, 96%, 97%, 98%, or 99% identity thereto, and having IL-15 binding activity; and optionally, a second, heterologous domain comprising an antibody molecule or an Fc domain.

In embodiments, upon thawing of the composition, the conservation agent improves one or more of viability, proliferation, cytotoxic activity or activation of the nucleated cell compared to a nucleated cell in the absence of the nanoparticle.

In embodiments, the Fc domain is wild-type or mutated. In embodiments, the Fc domain comprises the amino acid sequence of SEQ ID NO: 11 or SEQ ID NO: 12.

In some aspects, the disclosure provides a nanoparticle comprising a polypeptide that comprises the IL-15 receptor or fragment thereof comprises a sushi domain (e.g., of SEQ ID NO: 7 or SEQ ID NO: 8) and a second, heterologous domain comprising an effector-attenuated Fc domain, e.g., a human IgG2 Fc domain, e.g., a human IgG2 Fc domain of SEQ ID NO: 11 or an amino acid sequence having at least 80%, 85%, 90%, 95%, 96%, 97%, 98%, or 99% identity thereto.

The following aspects and embodiments may be combined with any of the aspects and embodiments herein, including the methods and compositions above.

In embodiments, the conservation agent is a stimulatory molecule for sustaining nucleated cell viability, proliferation, cytotoxic activity or activation. In embodiments, the conservation agent is an immunostimulatory cytokine; e.g., a cytokine belonging to the common γ chain or four α-helix bundle families.

In embodiments, the composition, e.g., the nanoparticle and/or the conservation agent, comprises an IL-15 complex, said IL-15 complex comprising an IL-15 molecule complexed, e.g., covalently or noncovalently, with a polypeptide, e.g., an IL-15 receptor or an IL-15-binding fragment thereof.

In one embodiment, the polypeptide comprises an IL-15 receptor alpha or an IL-15-binding fragment, e.g., an IL-15-binding domain, thereof. In one embodiment, the polypeptide comprises the extracellular domain of the IL-15 receptor alpha. In one embodiment, the polypeptide comprises the amino acid sequence of SEQ ID NO: 2 (full length wild-type IL-15 receptor alpha), or an IL-15 binding fragment thereof or an amino acid sequence having at least 80%, 85%, 90%, 95%, 96%, 97%, 98%, or 99% identity thereto, and having IL-15 binding activity. In other embodiments, the polypeptide comprises the amino acid sequence of SEQ ID NO: 3 (extracellular domain (ECD) of wild-type IL-15 receptor alpha), or an amino acid sequence having at least 80%, 85%, 90%, 95%, 96%, 97%, 98%, or 99% identity thereto, and having IL-15 binding activity. In other embodiments, the polypeptide comprises the amino acid sequence of SEQ ID NO: 4 (ECD of IL-15 receptor alpha isoform CRA_d), or an amino acid sequence having at least 80%, 85%, 90%, 95%, 96%, 97%, 98%, or 99% identity thereto, and having IL-15 binding activity.

In another embodiment, the polypeptide comprises:

a first domain comprising the amino acid sequence of SEQ ID NO: 2, SEQ ID NO: 3, or SEQ ID NO:4, or an amino acid sequence having at least 80%, 85%, 90%, 95%, 96%, 97%, 98%, or 99% identity thereto, and having IL-15 binding activity; and optionally, a second, heterologous domain, e.g., an immunoglobulin Fc domain or an antibody molecule, e.g., an immunoglobulin Fab or scFv fragment, a Fab fragment, a $FAB_2$ fragment, or an affibody fragment or derivative, e.g., a sdAb (nanobody) fragment, a heavy chain antibody fragment, single-domain antibody, a bi-specific or a multispecific antibody. In one embodiment, the second heterologous domain is an Fc domain or a Fab.

In another embodiment, the polypeptide comprises:

a first domain comprising the amino acid sequence of SEQ ID NO: 7 or SEQ ID NO: 8, or an amino acid sequence having at least 80%, 85%, 90%, 95%, 96%, 97%, 98%, or 99% identity thereto, and having IL-15 binding activity; and optionally, a second, heterologous domain, e.g., an immunoglobulin Fc domain or an antibody molecule, e.g., an immunoglobulin Fab or scFv fragment, a Fab fragment, a $FAB_2$ fragment, or an affibody fragment or derivative, e.g., a sdAb (nanobody) fragment, a heavy chain antibody fragment, single-domain antibody, a bi-specific or a multispecific antibody. In one embodiment, the second heterologous domain is an Fc domain or a Fab.

In embodiments, the composition, e.g., the nanoparticle and/or the conservation agent, comprises an IL-15 complex, said IL-15 complex comprising an IL-15 molecule complexed, e.g., covalently or noncovalently, with a polypeptide comprising an IL-15 receptor or an IL-15-binding fragment thereof. In embodiments, the IL-15 molecule comprises an IL-15 mutant, e.g., a human IL-15 polypeptide having one or more amino acid substitutions. In some embodiments, the IL-15 molecule comprises a substitution at position 72, e.g., an N to D substitution. In one embodiment, the IL-15 molecule is an IL-15$^{N72D}$ polypeptide of SEQ ID NO: 6 or an amino acid sequence having at least 80%, 85%, 90%, 95%, 96%, 97%, 98%, or 99% identity thereto, which has IL-15Ra binding activity. In embodiments, the polypeptide comprising the IL-15 receptor or fragment thereof comprises a sushi-Fc polypeptide of SEQ ID NO: 5 or an amino acid sequence having at least 80%, 85%, 90%, 95%, 96%, 97%, 98%, or 99% identity thereto, which has IL-15 binding activity. In embodiments, the polypeptide comprising the IL-15 receptor or fragment thereof comprises a sushi domain (e.g., of SEQ ID NO: 7 or SEQ ID NO: 8) and a second, heterologous domain comprising an effector-attenuated Fc domain, e.g., a human IgG2 Fc domain, e.g., a human IgG2 domain of SEQ ID NO: 11 or an amino acid sequence having at least 80%, 85%, 90%, 95%, 96%, 97%, 98%, or 99% identity thereto.

In embodiments, the composition further comprises a buffer. In embodiments, the composition further comprises an aqueous media.

In embodiments, upon thawing of the frozen composition, the conservation agent, e.g., IL-15 complex, promotes, e.g., conserves or enhances, viability, proliferation, cytotoxic activity or activation of the nucleated cell. In embodiments, promoting viability comprises increasing viability by at least 1%, 2%, 5%, 10%, 20%, 30%, 40%, 50%, 60%, 70%, 80%, 90%, 100%, 2-fold, 3-fold, 4-fold, or 5-fold compared to otherwise similar nucleated cells without the nanoparticle, e.g., as measured by staining with Acridine Orange and Propidium Iodide, e.g., by the assay of Example 32. In embodiments, promoting proliferation comprises increasing proliferation by at least 1%, 2%, 5%, 10%, 20%, 30%, 40%, 50%, 60%, 70%, 80%, 90%, 100%, 2-fold, 3-fold, 4-fold, or 5-fold compared to otherwise similar nucleated cells without the nanoparticle, e.g., as measured by counting viable cells at first and second timepoints, e.g., by the assay of Example 33. In embodiments, promoting cytotoxic activity comprises increasing cytotoxic activity by at least 1%, 2%, 5%, 10%, 20%, 30%, 40%, 50%, 60%, 70%, 80%, 90%, 100%, 2-fold, 3-fold, 4-fold, or 5-fold compared to otherwise similar nucleated cells without the nanoparticle, e.g., in an assay for cytotoxic activity against a cancer cell line, e.g., Daudi cells, e.g., an assay of Example 28. In embodiments, promoting activation comprises increasing activation by at least 1%, 2%, 5%, 10%, 20%, 30%, 40%, 50%, 60%, 70%, 80%, 90%, 100%, 2-fold, 3-fold, 4-fold, or 5-fold compared to otherwise similar nucleated cells without the nanoparticle, e.g., in a flow cytometry assay using an antibody against CD45RA, e.g., an assay of Example 26.

In embodiments, the conservation agent, e.g., IL-15 complex, is released from the nanoparticle. In embodiments, upon thawing the viability, proliferation, cytotoxic activity or activation of the nucleated cell is promoted, e.g., conserved or enhanced, as compared to a reference, e.g., an otherwise similar composition comprising a nucleated cell, but lacking the nanoparticle. In embodiments, upon thawing of frozen composition, the conservation agent promotes, e.g., conserves or enhances, viability, proliferation, cytotoxic activity or activation of the nucleated cell. In embodiments, interferon gamma production is promoted. In embodiments, activation is measured by interferon gamma production. In some embodiments, one, two, three, four or more of the viability, proliferation, cytotoxic activity, activation or interferon gamma production of the nucleated cell is/are promoted.

In embodiments, the composition comprises a compound that stimulates and sustains cell viability and proliferation. In embodiments, the composition comprises a compound that protects the cells during freezing and thawing. In embodiments, the composition comprises a second conservation agent, e.g., a conservation agent described herein. In embodiments, the release of conservation agent from the nanoparticle occurs over 1 hour to 3 weeks, such as 1 hour to 24 hours, 1 day to 3 days, 4 days to 6 days, 1 week to 2 weeks, or 2 weeks to 3 weeks.

In embodiments, the nanoparticle is associated with the surface of the nucleated cell, thus forming a nucleated cell-nanoparticle complex.

In embodiments, the nucleated cell comprises an immune cell, e.g., an immune effector cell, (e.g., an immune cell chosen from a lymphocyte, T cell, B cell, or a Natural Killer cell), or a hematopoietic stem cell). In embodiments, the nucleated cell comprises a lymphocyte. In embodiments, the nucleated cell comprises a T cell. In embodiments, the nucleated cell comprises a B cell. In embodiments, the nucleated cell comprises a Natural Killer (NK) cell. In embodiments, the nucleated cell comprises a hematopoietic stem cell. In some embodiments, the nucleated cell is an immune cell (e.g., T cell or NK cell) that comprises, e.g., expresses, a Chimeric Antigen Receptor (CAR), e.g., a CAR that binds to a cancer antigen. In other embodiment, the nucleated cell expresses an exogenous high affinity Fc receptor.

In embodiments, the nucleated cell is an immune cell, e.g., an NK cell, acquired from a patient, e.g., a patient's blood. In other embodiments, the nucleated cell is an immune cell, e.g., an NK cell, acquired from a healthy donor. For example, it is an NK cell population depleted in allogeneic T cells. In embodiments, the nucleated cell is an immune cell, e.g., an NK cell, from an embryonic stem cell and/or an iPSC cell. In some embodiments, the nucleated cell is a cell line, e.g., a stable or an immortalized cell line (e.g., an NK cell immortalized cell line). In some embodiments, the nucleated cell is acquired from a patient, e.g., a patient with a hematological cancer, e.g., a leukemia or a lymphoma. In embodiments, the nucleated cell is an NK cell line, e.g., an NK cell line chosen from NK-92 (e.g., ATCC cat. No. CRL-2407), NK-YS, KHYG-1, NKL, NKG, SNK-6, IMC-1, e.g., as described in Klingemann, H. et al. (2016) *Frontiers in Immunology* Vol. 7(Art. 91): 1-7, incorporated by reference herein. In one embodiment, the nucleated cell is an NK92 cell line, e.g., a variant NK92 cell that expresses a high affinity Fc receptor, e.g., Fc gamma RIIIa-expressing cell (e.g., 158V). In other embodiments, the NK92 cell line comprises a CAR that binds to a cancer antigen, e.g., also as described in in Klingemann et al. supra.

In embodiments, the nanoparticle is associated with the cell surface by electrostatic attraction to the nucleated cell. In embodiments, the nanoparticle comprises at least one ligand, wherein the ligand has affinity for proteins, carbohydrates or lipids on the surface of the nucleated cell.

In embodiments, the nanoparticle is covalently conjugated, e.g., to the surface, of the nucleated cell. In embodiments, the nanoparticle is not covalently conjugated to the nucleated cell.

In embodiments, the nanoparticle comprises a liposome, a protein nanogel, a nucleotide nanogel, a polymer nanoparticle, or a solid nanoparticle. In embodiments, the nanoparticle comprises a liposome. In embodiments, the nanoparticle comprises a protein nanogel. In some embodiments, the nanoparticle is a protein nanogel formed by a plurality of conservation agents covalently linked to each other. In embodiments, the nanoparticle comprises at least one polymer, cationic polymer, or cationic block co-polymer on the nanoparticle surface.

In some embodiments, the cationic polymer comprises poly-lysine, e.g., polyK30 or polyK200. In some embodiments, the poly-lysine is poly-L-lysine. In embodiments, the poly-lysine has an average length of 20-30, 30-40, 40-50, 50-100, 100-150, 150-200, 200-250, 250-300, 300-400, or 400-500 amino acids. In embodiments, the poly-lysine has an average length of 10-50, 20-40, or about 30 amino acids. In embodiments, the poly-lysine has an average length of 100-300, 150-250, or about 200 amino acids. In some embodiments, the poly-lysine has an average length of 10-150, 20-100, 20-80, 20-60, 20-40, or about 30 amino acids.

In embodiments, the nanoparticle comprises polyethylene glycol (PEG). In embodiments, the PEG has a molecular weight of 1-2, 2-3, 3-4, 4-5, 5-6, 6-7, 7-8, 8-9, or 9-10 kD.

In embodiments the PEG has a molecular weight of about 1-10, 2-8, 4-6, or about 5 kD.

In some embodiments, the nanoparticle comprises a cationic block co-polymer comprising PEG (e.g., a PEG as described herein, e.g., a PEG having a molecular weight of about 1-10, 2-8, 4-6, or about 5 kD) and a poly-lysine, (e.g., a poly-lysine as described herein, e.g., a poly-lysine having an average length of 10-50, 20-40, or about 30 amino acids; or a poly-lysine having an average length of 100-300, 150-250, or about 200 amino acids). In embodiments the cationic block co-polymer comprises PEG5k-polyK30 or PEG5k-polyK200.

In some embodiments, the composition (e.g., nanoparticle) comprises:

an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;

a sushi-Fc polypeptide of SEQ ID NO: 5 or an amino acid sequence having at least 80%, 85%, 90%, 95%, 96%, 97%, 98%, or 99% identity thereto, which has IL-15 binding activity; a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15 polypeptide of SEQ ID NO: 1 or an amino acid sequence having at least 80%, 85%, 90%, 95%, 96%, 97%, 98%, or 99% identity thereto which has IL-15Ra binding activity;

a sushi-Fc polypeptide comprising a sushi domain of SEQ ID NO: 7 or SEQ ID NO: 8 or an amino acid sequence having at least 80%, 85%, 90%, 95%, 96%, 97%, 98%, or 99% identity thereto, which has IL-15 binding activity, and an Fc domain of SEQ ID NO: 11 or an amino acid sequence having at least 80%, 85%, 90%, 95%, 96%, 97%, 98%, or 99% identity thereto;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;

a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15 polypeptide of SEQ ID NO: 1 or an amino acid sequence having at least 80%, 85%, 90%, 95%, 96%, 97%, 98%, or 99% identity thereto which has IL-15Ra binding activity;

a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In embodiments, the composition comprises (e.g., in solution or associated with the nanoparticle, e.g., covalently conjugated to the nanoparticle, e.g., as part of a conservation agent) a compound that stabilizes the nanoparticle in solution or on the cell surface and/or increases the interaction between the nanoparticle and the surface of the nucleated cell. In embodiments, the compound is chosen from protamine, chitosan, a carbohydrate, a heparan-sulfate proteoglycan, a natural polymer, a polysaccharide, a dextramer, cellulose, fibronectin, collagen, fibrin, or a proteoglycan. In embodiments, the composition comprises (e.g., in solution or associated with the nanoparticle, e.g., covalently conjugated to the nanoparticle, e.g., as part of a conservation agent) a cytokine molecule, growth factor molecule, a costimulatory molecule. In embodiments, the composition comprises (e.g., in solution or associated with the nanoparticle, e.g., covalently conjugated to the nanoparticle, e.g., as part of a conservation agent) a cytokine molecule, e.g., IL-2, IL-7, IL-12, IL-15, IL-18, IL-21, IL-23, IL-4, IL1alpha, IL1beta, IL-5, IFNgamma, TNFalpha, IFNalpha, IFNbeta, GM-CSF, or GCSF, a variant thereof, or a cytokine complex, e.g., an IL-15 complex (e.g., an IL-15 superagonist as described herein). In embodiments, the composition comprises (e.g., in solution or associated with the nanoparticle, e.g., covalently conjugated to the nanoparticle, e.g., as part of a conservation agent) or a molecule, e.g., an antibody molecule or agonist ligand against a costimulatory molecule, e.g., wherein the costimulatory molecule is chosen from OX40, CD28, GITR, VISTA, CD40, CD3, or an agonist of CD137.

In embodiments, the nanoparticle comprises an entity that reduces, e.g. inhibits, diminishes or decreases internalization, by the nucleated cell, of the nanoparticle. In embodiments, the nanoparticle comprises an antibody molecule to CD45, CD11a (integrin alpha-L), CD18 (integrin beta-2), CD11b, CD11c, CD25, CD8, or CD4.

In some embodiments, the nanoparticle comprises an entity that binds a protein, e.g., a receptor, present on an NK cell. For instance, the nanoparticle may comprise an entity that binds a stimulatory receptor or inhibitory receptor on an NK cell.

In embodiments, the entity is an agonist of a stimulatory receptor on an NK cell, e.g., the entity may be an agonist ligand or an agonist antibody molecule. In embodiments, the stimulatory receptor is TRAIL, CD16, NKp30a,b, DNAM-1, CD137, OX40, CD27, DAP12, FcεRI-γ, CD3-ζ, NKG2D, DAP10, or CD225 (2B4). In embodiments, the stimulatory receptor comprises an ITAM motif, e.g., (D/E)XXYXX(L/I)X$_{6-8}$YXX(L/I). In embodiments, the stimulatory receptor is a Natural Cytotoxicity Receptor or an MHC-Binding Activating Receptor.

In embodiments, the entity is an inhibitor of an inhibitory receptor on an NK cell, e.g., the entity may be an inhibitor ligand or an inhibitor antibody molecule. In embodiments, the inhibitory receptor is a KIR, LILR, Ly49, or NKG2A. In embodiments, the inhibitory receptor comprises an ITIM motif, e.g., (I/L/V/S)XYXX(L/V). In embodiments, the inhibitory receptor is an MHC Class I-Inhibitory Receptor or a Non-MHC-Binding Inhibitory Receptors.

In embodiments, the NK cell receptor is a receptor described in Lanier "Up on the tightrope: natural killer cell activation and inhibition" Nat Immunol. 2008 May; 9(5): 495-502, Sentman et al. "NK Cell Receptors as Tools in Cancer Immunotherapy" Advances in Cancer Research 2006 249-292, or Pardoll "The blockade of immune checkpoints in cancer immunotherapy" Nat Rev Cancer. 2012 Mar. 22; 12(4):252-64.

In some embodiments, the nanoparticle is a high-density protein structure (greater than 80% protein by weight), wherein the proteins are cross-linked by a cross-linking molecule that upon degradation release the proteins in a functional, e.g., native, form.

In embodiments, the nanoparticle comprises a nanogel that is cross linked by a reversible linker that is sensitive to redox (e.g., the linker comprises a disulfide linkage) or pH (e.g., the linker comprises a hydrolysable group) or enzymes (e.g., the linker comprises a protease cleavage site).

In embodiments, a composition herein comprises a particle, e.g., a nanoparticle or a microparticle, or both of a nanoparticle and a microparticle. In embodiments, the particle, e.g., nanoparticle, has an average hydrodynamic diameter (e.g., measured by dynamic light scattering) between 30 nm and 1200 nm, between 40 nm and 1,100 nm, between 50 nm and 1,000 nanometer, between such as 50-500 nm, more typically, between 70 and 400 nm. In embodiments, the particle, e.g., nanoparticle, has an average intensity-based size (e.g., measured by dynamic light scattering) between 100 nm and 400 nm, 150 nm and 350 nm, or 200 nm and 300 nm. In embodiments, the particle, e.g., nanoparticle, has an average number-based size (e.g., measured by dynamic light scattering) between 60 nm and 100 nm, or 70 nm and 90 nm. In embodiments, the composition is frozen. In embodiments, the composition comprises a frozen portion and a liquid portion.

In embodiments, the temperature of the composition is reduced to less than 0 degrees centigrade.

In embodiments, the temperature of the composition is reduced to less than negative 10 degrees centigrade. In embodiments, the temperature of the composition is reduced to less than negative 10, negative 20, negative 30, negative 40, negative 50, negative 60, negative 70, negative 80, negative 100, negative 120, negative 140, negative 160, negative 180, or negative 200 degrees centigrade. In embodiments, the method comprises maintaining the frozen composition of nucleated cells as frozen for at least one hour. In embodiments, the method comprises maintaining the frozen composition of nucleated cells as frozen for at least 2, 4, 6, 12, or 24 hours, or for 1, 2, 3, 4, 5, or 6 days, or for 1, 2, 3, or 4 weeks, or for 1, 2, 3, or 6 months, or for 1, 2, 3, 4, or 5 years.

In embodiments, providing comprises combining the nucleated cells with a nanoparticle that comprises a conservation agent. In embodiments, providing comprises receiving the nanoparticle from another entity and combining the nanoparticles with the nucleated cells. In embodiments, providing comprises receiving the unfrozen composition of nucleated cells from another entity.

In embodiments, the method comprises providing or releasing the frozen composition of nucleated cells to another entity, e.g., a healthcare provider, e.g., a hospital, clinic, or doctor's office. In embodiments, the method comprises thawing the frozen composition of nucleated cells to provide a thawed composition of nucleated cells. In embodiments, the method comprises, prior to warming the frozen composition of nucleated cells, maintaining the frozen composition of nucleated cells as frozen for at least one hour. In embodiments, upon thawing of a frozen preparation of the composition, the conservation agent is released from the nanoparticle and promotes, e.g., conserves or enhances, viability, proliferation, cytotoxic activity or activation of the nucleated cell as compared to a nucleated cell in a buffered aqueous media solution frozen and thawed absent the nanoparticle. In embodiments, the method comprises administering thawed composition of nucleated cells to a subject.

In embodiments, providing comprises receiving the frozen composition from another entity, e.g., an entity which makes and/or freezes the composition of nucleated cells. In embodiments, providing comprises combining the nucleated cells with a buffered aqueous media solution and a nanoparticle that comprises at least one conservation agent. In embodiments, providing comprises receiving the nanoparticle from another entity and combining the nanoparticles with the nucleated cells.

In embodiments, the method comprises expanding the cells, e.g., after thawing. In embodiments, the cells are expanded by at least 2-fold (e.g., over 2 days). In embodiments, the cells are expanded by at least 2, 3, 4, 5, 10, 20, 50, or 100-fold.

In embodiments, the method further comprises activating the cells, e.g., after thawing. In embodiments, the percentage of activated cells, e.g., activated CD8+ cells (measured as fraction CD45RA+, e.g., in a flow cytometry assay using an antibody against CD45RA, e.g., an assay of Example 26) is at least 40%, 50%, 60%, 70%, 80%, or 90%.

In embodiments, cells (e.g., thawed cells) treated with the compositions herein have cytotoxic activity, e.g., determined using an assay described in Example 27. In embodiments, the cytotoxic activity comprises a fraction killing of at least 10%, 20%, 30%, 40%, or 50% in an assay of Example 27. In embodiments, the cytotoxic activity comprises a fraction killing of at least 10%, 20%, 30%, 40%, or 50% in an assay for cytotoxic activity against a cancer cell line, e.g., Daudi cells, e.g., an assay of Example 28. In embodiments, the cytotoxic activity comprises a fraction killing of at least 10%, 20%, 30%, 40%, or 50% in an assay of Example 29. In embodiments, the cytotoxic activity comprises a fraction killing of at least 10%, 20%, 30%, 40%, or 50% in an assay of Example 30.

In embodiments, cells (e.g., thawed cells) treated with the compositions herein have in vivo expansion activity, e.g., in an assay where cells are injected into a subject, blood is drawn at a later timepoint, and the expanded donor cells are counted by a flow cytometry assay, e.g., in an assay of Example 35. In embodiments, the thawed cells treated with the composition herein expands in vivo to yield at least 10%, 20%, 30%, 40%, 50%, 60%, 70%, 80%, 90%, or 100% more cells compared to otherwise similar cells not treated with the composition.

In embodiments, cells (e.g., thawed cells) treated with the compositions herein have tumor infiltration activity, e.g., when a tumor is excised and expanded donor cells are counted by flow cytometry, e.g., in an assay of Example 36. In embodiments, the cells treated with the composition herein result in at least 200, 400, 600, or 800 cells/mg tumor. In embodiments, the cells treated with the composition herein result in greater tumor infiltration levels, e.g., by at least 1-fold, 2-fold, 3-fold, 4-fold, or 5-fold, compared to otherwise similar cells not treated with the composition In embodiments, the subject is the donor subject that provided the nucleated cells. In embodiments, the donor subject has a cancer, diabetes, an autoimmune disease or a cardiovascular disease, or is in need of a transplant. In embodiments, the subject is a subject other than the donor subject. In embodiments, the subject other than the donor subject is a healthy subject.

In some aspects, the present disclosure provides a composition comprising a nucleated cell, a buffered aqueous media solution, and a nanoparticle that comprises at least one conservation agent that promotes, e.g., conserves or enhances, viability, proliferation, cytotoxic activity or activation of the nucleated cell, wherein upon thawing of a frozen preparation of the composition, the conservation agent is optionally released from the nanoparticle and promotes, e.g., conserves or enhances, viability, proliferation, cytotoxic activity or activation of the nucleated cell as compared to a nucleated cell in a buffered aqueous media solution frozen and thawed absent the nanoparticle, wherein the conservation agent comprises an IL-15 molecule complexed, e.g., covalently or noncovalently, with a polypeptide comprising, e.g., an IL-15 receptor or an IL-15-binding fragment thereof. In one embodiment, the polypeptide comprises an IL-15 receptor alpha or an IL-15-binding fragment thereof. In one embodiment, the polypeptide comprises the extracellular domain of the IL-15 receptor alpha.

In one embodiment, the polypeptide comprises the amino acid sequence of SEQ ID NO: 2 (full length wild-type IL-15 receptor alpha), or an IL-15 binding fragment thereof; or an amino acid sequence having at least 80%, 85%, 90%, 95%, 96%, 97%, 98%, or 99% identity thereto, and having IL-15 binding activity. In other embodiments, the polypeptide comprises the amino acid sequence of SEQ ID NO: 3 (ECD of wild-type IL-15 receptor alpha), or an amino acid sequence having at least 80%, 85%, 90%, 95%, 96%, 97%, 98%, or 99% identity thereto, and having IL-15 binding activity. In other embodiments, the polypeptide comprises the amino acid sequence of SEQ ID NO: 4 (ECD of IL-15 receptor alpha isoform CRA_d), or an amino acid sequence having at least 80%, 85%, 90%, 95%, 96%, 97%, 98%, or 99% identity thereto, and having IL-15 binding activity.

In another embodiment, the polypeptide comprises:
a first domain comprising the amino acid sequence of SEQ ID NO: 2, SEQ ID NO: 3, or SEQ ID NO: 4, or an amino acid sequence having at least 80%, 85%, 90%, 95%, 96%, 97%, 98%, or 99% identity thereto, and having IL-15 binding activity; and optionally, a second, heterologous domain, e.g., an immunoglobulin Fc domain or an antibody molecule, e.g., an immunoglobulin Fab or scFv fragment, a Fab fragment, a $FAB_2$ fragment, or an affibody fragment or derivative, e.g. a sdAb (nanobody) fragment, a heavy chain antibody fragment, single-domain antibody, a bi-specific or a multispecific antibody. In one embodiment, the second heterologous domain is an Fc domain or a Fab.

In embodiments, the composition, e.g., the nanoparticle and/or the conservation agent, comprises an IL-15 complex, said IL-15 complex comprising an IL-15 molecule complexed, e.g., covalently or noncovalently, with a polypeptide comprising an IL-15 receptor or an IL-15-binding fragment thereof. In embodiments, the IL-15 molecule comprises a human IL-15 N72D polypeptide of SEQ ID NO: 6 or an amino acid sequence having at least 80%, 85%, 90%, 95%, 96%, 97%, 98%, or 99% identity thereto, which has IL-15Ra binding activity. In embodiments, the polypeptide comprising the IL-15 receptor or fragment thereof comprises an IL15RaSu-Fc polypeptide of SEQ ID NO: 5 or an amino acid sequence having at least 80%, 85%, 90%, 95%, 96%, 97%, 98%, or 99% identity thereto, which has IL-15 binding activity. In embodiments, the polypeptide comprising the IL-15 receptor or fragment thereof comprises a sushi domain (e.g., of SEQ ID NO: 7 or SEQ ID NO: 8) and a second, heterologous domain comprising an effector-attenuated Fc domain, e.g., a human IgG2 Fc domain, e.g., a human IgG2 domain of SEQ ID NO: 11 or an amino acid sequence having at least 80%, 85%, 90%, 95%, 96%, 97%, 98%, or 99% identity thereto.

In some embodiments, the composition (e.g., nanoparticle) comprises:
an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;
a sushi-Fc polypeptide of SEQ ID NO: 5 or an amino acid sequence having at least 80%, 85%, 90%, 95%, 96%, 97%, 98%, or 99% identity thereto, which has IL-15 binding activity;
a cationic block co-polymer comprising PEG having a molecular weight of about 1-10, 2-8, 4-6, or about 5 kD and a poly-lysine having an average length of 10-50, 20-40, or about 30 amino acids; and
optionally, an antibody molecule to CD45.

In some embodiments, the composition (e.g., nanoparticle) comprises:
an IL-15 polypeptide of SEQ ID NO: 1 or an amino acid sequence having at least 80%, 85%, 90%, 95%, 96%, 97%, 98%, or 99% identity thereto which has IL-15Ra binding activity;
a sushi-Fc polypeptide comprising a sushi domain of SEQ ID NO: 7 or SEQ ID NO: 8 or an amino acid sequence having at least 80%, 85%, 90%, 95%, 96%, 97%, 98%, or 99% identity thereto, which has IL-15 binding activity, and an Fc domain of SEQ ID NO: 11 or an amino acid sequence having at least 80%, 85%, 90%, 95%, 96%, 97%, 98%, or 99% identity thereto;
a cationic block co-polymer comprising PEG having a molecular weight of about 1-10, 2-8, 4-6, or about 5 kD and a poly-lysine having an average length of 10-50, 20-40, or about 30 amino acids; and
optionally, an antibody molecule to CD45.

In some embodiments, the composition (e.g., nanoparticle) comprises:
an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;
a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;
a cationic block co-polymer comprising PEG having a molecular weight of about 1-10, 2-8, 4-6, or about 5 kD and a poly-lysine having an average length of 10-50, 20-40, or about 30 amino acids; and
optionally, an antibody molecule to CD45.

In some embodiments, the composition (e.g., nanoparticle) comprises:
an IL-15 polypeptide of SEQ ID NO: 1 or an amino acid sequence having at least 80%, 85%, 90%, 95%, 96%, 97%, 98%, or 99% identity thereto which has IL-15Ra binding activity;
a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In embodiments, the conservation agent is a stimulatory molecule for sustaining nucleated cell viability, proliferation, cytotoxic activity or activation.

In embodiments, interferon gamma production is promoted. In embodiments, activation is measured by interferon gamma production.

In embodiments, the media contains a compound that stimulate and sustains cell viability and proliferation. In embodiments, the media comprises a compound that protects the cells during freezing and thawing.

In embodiments, the release of the conservation agent from the nanoparticle occurs over 1 hour to 3 weeks, such as 1 hour to 24 hours, 1 day to 3 days, 4 days to 6 days, 1 week to 2 weeks, or 2 weeks to 3 weeks.

In embodiments, the nanoparticle is associated with the surface of the nucleated cell.

In embodiments, the nucleated cell is an immune cell, e.g., an immune effector cell (e.g., a lymphocyte, a T cell, a B cell, or a Natural Killer cell), or a hematopoietic stem cell. In some embodiments, the nucleated cell is an immune cell or a cell line as described herein.

In embodiments, the nanoparticle is associated with the cell surface by electrostatic attraction to the nucleated cell. In embodiments, the nanoparticle comprises at least one ligand, wherein the ligand has affinity for proteins, carbohydrates or lipids on the surface of the nucleated cell. In embodiments, the nanoparticle is covalently conjugated to the surface of the nucleated cell. In embodiments, the nanoparticle is not covalently conjugated to the surface of the nucleated cell. In embodiments, the nanoparticle comprises a liposome, a protein nanogel, a nucleotide nanogel, a polymer nanoparticle, or a solid nanoparticle. In embodiments, the nanoparticle comprises a liposome. In embodiments, the nanoparticle comprises a protein nanogel. In embodiments, the nanoparticle comprises at least one polymer, cationic polymer, or cationic block co-polymer on the nanoparticle surface.

In embodiments, the nanoparticle comprises polyethylene glycol (PEG). In embodiments, the composition comprises a compound that stabilizes the nanoparticle in solution or on the cell surface and/or increases the interaction between the nanoparticle and the surface of the nucleated cell. In some embodiments, the compound is chosen from protamine, chitosan, a carbohydrate, a heparan-sulfate proteoglycan, a natural polymer, a polysaccharide, a dextramer, cellulose, fibronectin, collagen, fibrin, or a proteoglycan.

In embodiments, the conservation agent comprises a cytokine molecule, growth factor molecule, a costimulatory molecule. In embodiments, the composition comprises a first and/or second conservation agent which comprises a cytokine molecule. In some embodiments, the cytokine molecule is chosen from IL-2, IL-7, IL-12, IL-15, IL-18, IL-21, IL-23, IL-4, IL1alpha, IL-1beta, IL-5, IFN gamma, TNFa, IFNalpha, IFNbeta, GM-CSF, or GCSF, a variant thereof, or a cytokine complex, or any combination of the aforesaid. In some embodiments, the cytokine molecule comprises an IL-15 complex, e.g., an IL-15 superagonist as described herein. In embodiments, the composition comprises an antibody molecule or agonist ligand against a costimulatory molecule, e.g., wherein the costimulatory molecule is chosen from OX40, CD28, GITR, VISTA, CD40, CD3, or an agonist of CD137.

In embodiments, the nanoparticle comprises an entity that reduces, e.g., inhibits, diminishes or decreases internalization, by the nucleated cell, of the nanoparticle. In embodiments, the nanoparticle comprises an antibody molecule to CD45, CD11a (integrin alpha-L), CD18 (integrin beta-2), CD11b, CD11c, CD25, CD8, or CD4.

In embodiments, the nanoparticle comprises a nanogel that is cross linked by a reversible linker that is sensitive to redox (e.g., disulfide) or pH (e.g., hydrolysable groups) or enzymes (e.g., proteases).

In embodiments, the composition is frozen. In embodiments, the composition comprises a frozen portion and a liquid portion.

In another aspect, the invention features a method for promoting, e.g., enhancing, the viability, proliferation, cytotoxic activity or activation of a nucleated cell. In embodiments, the nucleated cell is, or has been, isolated from a patient. The method comprises modifying the nucleated cell by combining it with a buffered aqueous solution, a nanoparticle that comprises at least one agent that conserves or enhances the viability, proliferation, cytotoxic activity or activation of the nucleated cell, e.g., a conservation agent as described herein.

In another aspect, the invention features a method for promoting, e.g., enhancing, the viability, proliferation, cytotoxic activity or activation of a nucleated cell. In embodiments, the nucleated cell is, or has been, isolated from a patient and modified by combination with a buffered aqueous solution, a nanoparticle that comprises at least one agent that conserves or enhances the viability, proliferation, cytotoxic activity or activation of the nucleated cell, e.g., a conservation agent as described herein. The method comprises subjecting the nucleated cell to at least one freeze thaw cycle.

In certain aspects, the invention features a method of making a frozen composition of nucleated cells comprising:

a) providing an unfrozen composition comprising nucleated cells, a buffered aqueous media solution and a nanoparticle that comprises at least one conservation agent, that, e.g., an agent that upon thawing of a frozen preparation of the nucleated cells, promotes, e.g., conserves or enhances, the viability, proliferation, cytotoxic activity or activation of the nucleated cells (e.g., providing an unfrozen nucleated cell-nanoparticle complex);

b) optionally, reducing the temperature of the composition sufficiently for the composition to freeze, thereby freezing a composition of nucleated cells.

In embodiments, the temperature of the composition is reduced to less than 0 degrees centigrade. In embodiments, the temperature of the composition is reduced to less than negative 10 degrees centigrade. In embodiments, the method comprises maintaining the frozen composition of nucleated cells as frozen for at least one hour.

In embodiments, providing comprises: combining the nucleated cells with a buffered aqueous media solution and a nanoparticle that comprises at least one conservation agent, thus forming a nucleated cell-nanoparticle complex. In embodiments, providing comprises receiving the nanoparticle from another entity and combining the nanoparticles with the nucleated cells and the buffered aqueous media solution. In embodiments, providing comprises receiving the unfrozen composition of nucleated cells from another entity.

In embodiments, the method comprises providing or releasing the frozen composition of nucleated cells to another entity, e.g., a healthcare provider, e.g., a hospital, clinic, or doctor's office. In embodiments, the method comprises thawing the frozen composition of nucleated cells to provide a thawed composition of nucleated cells.

In embodiments, upon thawing of a frozen preparation of the composition, the conservation agent is released from the nanoparticle and promotes, e.g., conserves or enhances, viability, proliferation, cytotoxic activity or activation of the nucleated cell as compared to a nucleated cell in a buffered aqueous media solution frozen and thawed absent the nanoparticle.

In embodiments, the method comprises administering the thawed composition of nucleated cells to a subject. In embodiments, the subject is the donor subject. In embodiments, the donor subject has a cancer, diabetes, an autoimmune disorder, or is in need of a transplant. In embodiments, the subject is a subject other than the donor subject. In embodiments, the subject other than the donor subject is a healthy subject.

In some embodiments of any of the aforesaid compositions and methods, the conservation agent comprises an IL-15 superagonist, e.g., an IL-15 molecule having higher activity than wild type IL-15. In embodiments, the conservation agent comprises an IL-15 molecule and a polypeptide, e.g., an IL-15 polypeptide receptor alpha fragment, (e.g., an extracellular domain of the IL-15 receptor alpha).

In one embodiment, the polypeptide comprises:

a first domain comprising the amino acid sequence of SEQ ID NO: 2 (wild-type IL-15 receptor alpha), or an amino acid sequence having at least 80%, 85%, 90%, 95%, 96%, 97%, 98%, or 99% identity thereto, and having IL-15 binding activity; and optionally, a second, heterologous domain, e.g., an immunoglobulin Fc domain or an antibody molecule, e.g., an immunoglobulin Fab or scFv fragment, a Fab fragment, a $FAB_2$ fragment, or an affibody fragment or derivative, e.g. a sdAb (nanobody) fragment, a heavy chain antibody fragment, single-domain antibody, a bi-specific or a multispecific antibody. In one embodiment, the second heterologous domain is an Fc domain or a Fab.

In another embodiment, the polypeptide comprises:

a first domain comprising the amino acid sequence of SEQ ID NO: 3, or an amino acid sequence having at least 80%, 85%, 90%, 95%, 96%, 97%, 98%, or 99% identity thereto, and having IL-15 binding activity; and optionally, a second, heterologous domain, e.g., an immunoglobulin Fc domain or an antibody molecule, e.g., an immunoglobulin Fab or scFv fragment, a Fab fragment, a $FAB_2$ fragment, or an affibody fragment or derivative, e.g. a sdAb (nanobody) fragment, a heavy chain antibody fragment, single-domain antibody, a bi-specific or a multispecific antibody. In one embodiment, the second heterologous domain is an Fc domain or a Fab.

In one embodiment, the polypeptide comprises:

a first domain comprising the amino acid sequence of SEQ ID NO: 4 (ECD of IL-15 receptor alpha isoform CRA_d), or an amino acid sequence having at least 80%, 85%, 90%, 95%, 96%, 97%, 98%, or 99% identity thereto, and having IL-15 binding activity; and optionally, a second, heterologous domain, e.g., an immunoglobulin Fc domain or an antibody molecule, e.g., an immunoglobulin Fab or scFv fragment, a Fab fragment, a $Fab_2$ fragment, or an affibody fragment or derivative, e.g. a sdAb (nanobody) fragment, a heavy chain antibody fragment, single-domain antibody, a bi-specific or a multispecific antibody. In one embodiment, the second heterologous domain is an Fc domain or a Fab.

In embodiments, the composition, e.g., the nanoparticle and/or the conservation agent, comprises an IL-15 complex, said IL-15 complex comprising an IL-15 molecule complexed, e.g., covalently or noncovalently, with a polypeptide comprising an IL-15 receptor or an IL-15-binding fragment thereof. In embodiments, the IL-15 molecule comprises a human IL-15 N72D polypeptide of SEQ ID NO: 6 or an amino acid sequence having at least 80%, 85%, 90%, 95%, 96%, 97%, 98%, or 99% identity thereto, which has IL-15Ra binding activity. In embodiments, the polypeptide comprising the IL-15 receptor or fragment thereof comprises an IL15RaSu-Fc polypeptide of SEQ ID NO: 5 or an amino acid sequence having at least 80%, 85%, 90%, 95%, 96%, 97%, 98%, or 99% identity thereto, which has IL-15 binding activity. In embodiments, the polypeptide comprising the IL-15 receptor or fragment thereof comprises a sushi domain (e.g., of SEQ ID NO: 7 or SEQ ID NO: 8) and a second, heterologous domain comprising an effector-attenuated Fc domain, e.g., a human IgG2 Fc domain, e.g., a human IgG2 domain of SEQ ID NO: 11 or an amino acid sequence having at least 80%, 85%, 90%, 95%, 96%, 97%, 98%, or 99% identity thereto.

In some embodiments, the composition (e.g., nanoparticle) comprises:

an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;

a sushi-Fc polypeptide of SEQ ID NO: 5 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15 polypeptide of SEQ ID NO: 1 or an amino acid sequence having at least 80%, 85%, 90%, 95%, 96%, 97%, 98%, or 99% identity thereto which has IL-15Ra binding activity;

a sushi-Fc polypeptide comprising a sushi domain of SEQ ID NO: 7 or SEQ ID NO: 8 or an amino acid sequence having at least 80%, 85%, 90%, 95%, 96%, 97%, 98%, or 99% identity thereto, which has IL-15 binding activity, and an Fc domain of SEQ ID NO: 11 or an amino acid sequence having at least 80%, 85%, 90%, 95%, 96%, 97%, 98%, or 99% identity thereto;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;

a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15 polypeptide of SEQ ID NO: 1 or an amino acid sequence having at least 80%, 85%, 90%, 95%, 96%, 97%, 98%, or 99% identity thereto which has IL-15Ra binding activity;

a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In embodiments, the conservation agent is a stimulatory molecule for sustaining nucleated cell viability, proliferation, cytotoxic activity or activation.

In embodiments, interferon gamma production is promoted. In embodiments, activation can be measured by interferon gamma production.

In embodiments, the media contains a compound that stimulates and sustains cell viability and proliferation. In embodiments, the media comprises a compound that protects the cells during freezing and thawing.

In embodiments, the release of conservation agent from the nanoparticle occurs over 1 hour to 3 weeks, such as 1 hour to 24 hours, 1 day to 3 days, 4 days to 6 days, 1 week to 2 weeks, or 2 weeks to 3 weeks.

In embodiments, the nanoparticle is associated, e.g., covalently or noncovalently, with the nucleated cell, e.g., the surface of the nucleated cell, thus forming a nucleated cell-nanoparticle complex.

In embodiments, the nucleated cell is an immune effector cell (e.g., a lymphocyte, T cell, B cell, or Natural Killer cell), or a hematopoietic stem cell. In some embodiments, the nucleated cell is an immune cell (e.g., T cell or NK cell) that comprises, e.g., expresses, a Chimeric Antigen Receptor (CAR), e.g., a CAR that binds to a cancer antigen. In other embodiment, the nucleated cell expresses an exogenous high affinity Fc receptor. In embodiments, the nucleated cell is an NK cell acquired from a patient, or a healthy donor. In other embodiments, the nucleated cell is an NK cell line, e.g., a stable or immortalized cell line as described herein. In one embodiment, the NK cell is an NK-92 cell line.

In embodiments, the nanoparticle comprises at least one ligand, wherein the ligand has affinity for proteins, carbohydrates or lipids on the surface of the nucleated cell.

In embodiments, the nanoparticle is covalently conjugated to the surface of the nucleated cell. In embodiments, the nanoparticle is not covalently conjugated to the surface of the nucleated cell.

In embodiments, the nanoparticle comprises a liposome, a protein nanogel, a nucleotide nanogel, a polymer nanoparticle, or a solid nanoparticle. In embodiments, the nanoparticle comprises a liposome. In embodiments, the nanoparticle comprises a protein nanogel. In embodiments, the nanoparticle optionally comprises at least one polymer, cationic polymer, or cationic block co-polymer on the nanoparticle surface. In embodiments, the nanoparticle comprises polyethylene glycol (PEG).

In embodiments, the composition comprises a compound that stabilizes the nanoparticle in solution or on the cell surface and/or increases the interaction between the nanoparticle and the surface of the nucleated cell. In some embodiments, the agent is chosen from a protamine, a chitosan, a carbohydrate, a heparan-sulfate proteoglycan, a natural polymer, a polysaccharide, a dextramer, a cellulose, a fibronectin, a collagen, a fibrin, or a proteoglycan.

In embodiments, the conservation agent comprises a cytokine molecule, a growth factor molecule, or a costimulatory molecule. In embodiments, the conservation agent comprises a cytokine molecule, e.g., IL-2, IL-7, IL-12, IL-15, IL-18, IL-21, IL-23, IL-4, IL-1alpha, IL-1beta, IL-5, IFNgamma, TNFa, IFNalpha, IFNbeta, GM-CSF, or GCSF, variant thereof, or a cytokine complex, e.g., an IL-15 complex (e.g., an IL-15 superagonist as described herein). In some embodiment, the cytokine molecule further comprises, e.g., is coupled (e.g., fused) to an antibody molecule, (e.g., an immunoglobulin Fab or scFv fragment, a Fab fragment, a FAB$_2$ fragment, or an affibody fragment or derivative, e.g. a sdAb (nanobody) fragment, a heavy chain antibody fragment, e.g., an immunoglobulin Fc, single-domain antibody, a bi-specific or a multispecific antibody.

In embodiments, the composition comprises an agonist (e.g., an antibody molecule or an agonist ligand) of a costimulatory molecule, e.g., OX40, CD28, GITR, VISTA, CD40, CD3, or an agonist of CD137.

In embodiments, the nanoparticle comprises an entity that reduces, e.g., inhibits, diminishes or decreases internalization, by the nucleated cell, of the nanoparticle. In embodiments, the nanoparticle comprises an antibody molecule to CD45, CD11a (integrin alpha-L), CD18 (integrin beta-2), CD11b, CD11c, CD25, CD8, or CD4. In embodiments, the nanoparticle comprises an anti-CD45 affinity or binding ligand conjugated to the surface of the nanoparticle. In embodiments, the nanoparticle comprises a nanogel that is cross linked by a reversible linker that is sensitive to redox (e.g., disulfide) or pH (e.g., hydrolysable groups) or enzymes (e.g., proteases).

In some aspects, the invention features a method of making a thawed composition of nucleated cells, comprising:

a) providing a frozen composition of nucleated cells comprising nucleated cells, a buffered aqueous media solution and a nanoparticle that comprises at least one conservation agent, that, e.g., upon thawing of a frozen preparation of the nucleated cells, promotes, e.g., conserves or enhances, the viability, proliferation, cytotoxic activity or activation of the nucleated cells (e.g., providing a nucleated cell-nanoparticle complex as disclosed herein); and b) warming the frozen composition of nucleated cells sufficiently to thaw the frozen composition of nucleated cells, thereby making a thawed composition of nucleated cells.

In some embodiments, providing comprises receiving the frozen composition from another entity, e.g., an entity which makes and/or freezes the composition of nucleated cells. In some embodiments, providing comprises: combining the nucleated cells with a buffered aqueous media solution and a nanoparticle that comprises at least one conservation agent, thus forming a nucleated cell-nanoparticle complex. In some embodiments, providing comprises receiving the nanoparticle from another entity and combining the nanoparticles with the nucleated cells and the buffered aqueous media solution.

In some embodiments, the method comprises, prior to warming the frozen composition of nucleated cells, maintaining the frozen composition of nucleated cells as frozen for at least one hour.

In embodiments, the subject is the donor subject that donated the nucleated cells. In embodiments, the donor subject, e.g., patient, has a cancer, diabetes, an autoimmune disease or a cardiovascular disease, or is in need of a transplant. In embodiments, the subject is a subject other than the donor subject. In embodiments, the subject other than the donor subject is a healthy subject.

In some embodiments, the conservation agent comprises: an IL-15 polypeptide receptor alpha fragment chosen from one of the following:

i) the amino acid sequence of SEQ ID NO: 2, or an amino acid sequence having at least 80%, 85%, 90%, 95%, 96%, 97%, 98%, or 99% identity thereto, and having IL-15 binding activity;

ii) the amino acid sequence of SEQ ID NO: 3, or an amino acid sequence having at least 80%, 85%, 90%, 95%, 96%, 97%, 98%, or 99% identity thereto, and having IL-15 binding activity;

iii) the amino acid sequence of SEQ ID NO: 4, or an amino acid sequence having at least 80%, 85%, 90%, 95%, 96%, 97%, 98%, or 99% identity thereto, and having IL-15 binding activity;

and optionally, a second, heterologous domain, e.g., an immunoglobulin Fc domain or an antibody molecule, e.g., an immunoglobulin Fab or scFv fragment, a Fab fragment, a FAB$_2$ fragment, or an affibody fragment or derivative, e.g. a sdAb (nanobody) fragment, a heavy chain antibody fragment, single-domain antibody, a bi-specific or a multispecific antibody. In one embodiment, the second heterologous domain is an Fc domain or a Fab.

In some embodiments, the conservation agent comprises a complex of an IL-15 molecule and the IL-15 polypeptide receptor alpha fragment.

In embodiments, the composition, e.g., the nanoparticle and/or the conservation agent, comprises an IL-15 complex, said IL-15 complex comprising an IL-15 molecule complexed, e.g., covalently or noncovalently, with a polypeptide comprising an IL-15 receptor or an IL-15-binding fragment thereof. In embodiments, the IL-15 molecule comprises a human IL-15 N72D polypeptide of SEQ ID NO: 6 or an amino acid sequence having at least 80%, 85%, 90%, 95%, 96%, 97%, 98%, or 99% identity thereto, which has IL-15Ra binding activity. In embodiments, the polypeptide comprising the IL-15 receptor or fragment thereof comprises an IL15RaSu-Fc polypeptide of SEQ ID NO: 5 or an amino acid sequence having at least 80%, 85%, 90%, 95%, 96%, 97%, 98%, or 99% identity thereto, which has IL-15 binding activity. In embodiments, the polypeptide comprising the IL-15 receptor or fragment thereof comprises a sushi domain (e.g., of SEQ ID NO: 7 or SEQ ID NO: 8) and a second, heterologous domain comprising an effector-attenuated Fc domain, e.g., a human IgG2 Fc domain, e.g., a human IgG2 domain of SEQ ID NO: 11 or an amino acid sequence having at least 80%, 85%, 90%, 95%, 96%, 97%, 98%, or 99% identity thereto.

In some embodiments, the composition (e.g., nanoparticle) comprises:

an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;

a sushi-Fc polypeptide of SEQ ID NO: 5 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15 polypeptide of SEQ ID NO: 1 or an amino acid sequence having at least 80%, 85%, 90%, 95%, 96%, 97%, 98%, or 99% identity thereto which has IL-15Ra binding activity;

a sushi-Fc polypeptide comprising a sushi domain of SEQ ID NO: 7 or SEQ ID NO: 8 or an amino acid sequence having at least 80%, 85%, 90%, 95%, 96%, 97%, 98%, or 99% identity thereto, which has IL-15 binding activity, and an Fc domain of SEQ ID NO: 11 or an amino acid sequence having at least 80%, 85%, 90%, 95%, 96%, 97%, 98%, or 99% identity thereto;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;

a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In some embodiments, the composition (e.g., nanoparticle) comprises:

an IL-15 polypeptide of SEQ ID NO: 1 or an amino acid sequence having at least 80%, 85%, 90%, 95%, 96%, 97%, 98%, or 99% identity thereto which has IL-15Ra binding activity;

a sushi-Fc2 Da polypeptide of SEQ ID NO: 15 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

In embodiments, the conservation agent is a stimulatory molecule for sustaining nucleated cell viability, proliferation, cytotoxic activity or activation.

In embodiments, interferon gamma production is promoted. In embodiments, activation can be measured by interferon gamma production.

In embodiments, the media contains a compound that stimulates and sustains cell viability and proliferation. In embodiments, the media comprises a compound that protects the cells during freezing and thawing.

In embodiments, the release of conservation agent from the nanoparticle occurs over 1 hour to 3 weeks, such as 1 hour to 24 hours, 1 day to 3 days, 4 days to 6 days, 1 week to 2 weeks, or 2 weeks to 3 weeks.

In embodiments, the nanoparticle is associated with the surface of the nucleated cell.

In embodiments, the nucleated cell is an immune effector cell (e.g., a lymphocyte, T cell, B cell, or Natural Killer cell) or a hematopoietic stem cell.

In embodiments, the nanoparticle is associated with the cell surface by electrostatic attraction to the nucleated cell. In embodiments, the nanoparticle comprises at least one ligand, wherein the ligand has affinity for proteins, carbohydrates or lipids on the surface of the nucleated cell.

In embodiments, the nanoparticle is covalently conjugated to the surface of the nucleated cell. In embodiments, the nanoparticle is not covalently conjugated to the surface of the nucleated cell.

In embodiments, the nanoparticle comprises a liposome, a protein nanogel, a nucleotide nanogel, a polymer nanoparticle, or a solid nanoparticle. In embodiments, the nanoparticle comprises a liposome. In embodiments, the nanoparticle comprises a protein nanogel.

In embodiments, the nanoparticle comprises at least one polymer, cationic polymer, or cationic block co-polymer on the nanoparticle surface. In embodiments, the nanoparticle comprises polyethylene glycol (PEG).

In embodiments, the composition comprises a compound that stabilizes the nanoparticle in solution or on the cell surface and/or increases the interaction between the nanoparticle and the surface of the nucleated cell, e.g., protamine, chitosan, a carbohydrate, a heparan-sulfate proteoglycan, a natural polymer, a polysaccharide, a dextramer, cellulose, fibronectin, collagen, fibrin, or a proteoglycan.

In embodiments, the conservation agent comprises a cytokine molecule, a cytokine complexed with a polypeptide, e.g. its receptor or a fragment or portion of its receptor, a growth factor molecule, or a costimulatory molecule. In embodiments, the conservation agent comprises a cytokine molecule, e.g., IL2, IL7, IL12, IL15, IL18, IL21, IL-23, IL-4, IL1alpha, IL1beta, IL-5, IFNgamma, TNFa, IFNalpha, IFNbeta, GM-CSF, or GCSF, variant thereof, or a cytokine complex, e.g., an IL-15 complex (e.g., an IL-15 superagonist) as described herein. In embodiments, the conservation agent comprises a cytokine molecule, e.g., IL-15, associated with a fragment of the IL-15 receptor a chain, e.g., a fragment as described herein. In some embodiment, the cytokine molecule further comprises, e.g., is coupled (e.g., fused) to an antibody molecule, (e.g., an immunoglobulin Fab or scFv fragment, a Fab fragment, a $FAB_2$ fragment, or an affibody fragment or derivative, e.g. a sdAb (nanobody) fragment, a heavy chain antibody fragment, e.g., an immunoglobulin Fc, single-domain antibody, a bi-specific or a multispecific antibody. In embodiments, the composition comprises an agonist, e.g., an antibody molecule or agonist ligand against a costimulatory molecule, e.g., wherein the costimulatory molecule is chosen from OX40, CD28, GITR, VISTA, CD40, CD3, or an agonist of CD137.

In embodiments, the nanoparticle comprises an entity that reduces, e.g. inhibits, diminishes or decreases internalization, by the nucleated cell, of the nanoparticle. In embodiments, the nanoparticle comprises an antibody molecule to CD45, CD11a (integrin alpha-L), CD18 (integrin beta-2), CD11b, CD11c, CD25, CD8, or CD4. In embodiments, the nanoparticle comprises a nanogel that is cross linked by a reversible linker that is sensitive to redox (e.g., disulfide) or pH (e.g., hydrolysable groups) or enzymes (e.g., proteases).

In some aspects, the invention features a method for freezing a nucleated cell and a nanoparticle (e.g., the nucleated cell-nanoparticle complex), wherein the nucleated cells are frozen at less than negative 10 degrees centigrade and thawed after at least 1 hour, wherein said nanoparticle comprises at least one agent that is optionally released from the nanoparticle after thawing that maintains the function of the cell, e.g., preserves the cells viability compared to a composition of a nucleated cell frozen without a nanoparticle.

In some embodiments, the agent is a stimulatory molecule for sustaining nucleated cell viability. In embodiments, the nucleated carrier cell is a lymphocyte. In embodiments, the nanoparticle is associated with the surface of the nucleated cell. In embodiments, the nanoparticle is covalently conjugated to the surface of the nucleated cell.

In another aspect, the invention features a pharmaceutical composition comprising the composition described herein, e.g., a composition comprising a nucleated cell and a nanoparticle that comprises at least one conservation agent (e.g., a nucleated cell-nanoparticle complex), and a pharmaceutically acceptable carrier.

In embodiments, a subject herein is in need of a cell-based therapy, e.g., an immune cell therapy. For example, the subject is in need of adoptive cell therapy. In some embodiments, the subject is a patient, e.g., a human patient. In some embodiments, the subject has a disease chosen from cancer, diabetes, an autoimmune disease, allergies or allergic conditions, asthma or a cardiovascular disease. In embodiments, the subject is in need of a transplant.

In embodiments, the methods herein further comprise evaluating a function of the nucleated cells in the complex, e.g., evaluating one or more of proliferative, cytokine release or cytotoxic effect of the nucleated cell, e.g., after thawing.

Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

BRIEF DESCRIPTION OF THE DRAWINGS

FIG. 1A is a schematic of IL-15$^{WT}$/sushi-Fc: WT human IL-15 noncovalently associated with the sushi domain of human IL-15Ra fused to the N-terminus of human IgG1 Fc region. FIG. 1B is schematic of IL-15$^{N72D}$/sushi-Fc: Human IL-15 containing N72D mutation noncovalently associated with the sushi domain of human IL-15Ra fused to the N-terminus of human IgG1 Fc region.

In FIG. 11A, CD3 T cells were associated (rightmost group) or not (3 leftmost groups) with IL-15$^{N72D}$/sushi-Fc protein nanogels (Backpacks) before freezing in serum-free media (Bambanker) for 2 weeks. Upon thawing, first group was cultured in complete media (Media only), second group was cultured in IL-2 containing (20 ng/ml) complete media (IL-2 (soluble)), third group was cultured in IL-15$^{N72D}$/sushi-Fc containing (0.6 ug/ml) complete media (IL-15$^{N72D}$/sushi-Fc (0.6 ug/ml)) and fourth group was cultured in complete media (IL-15$^{N72D}$/sushi-Fc Backpacks). The number of live cells was measured after 16 hours (gray bars) and on day 9 (black bars) by flow cytometry. In FIG. 11B, CD3 T cells were conjugated (rightmost group) or not (3 leftmost groups) with IL-15$^{WT}$/sushi-Fc Backpacks before freezing in serum-free media (Bambanker) overnight. Upon thawing, first group was cultured in complete media (Media only), second group was cultured in IL-2 containing (20 ng/ml) complete media (IL-2 (soluble)), third group was cultured in IL-15$^{WT}$/sushi-Fc containing (12 ug/ml) complete media (IL-15$^{WT}$/sushi-Fc (12 ug/ml)) and fourth group was cultured in complete media (IL-15$^{WT}$/sushi-Fc Backpacks). The number of live cells was measured on day 2 (light gray bars), on day 6 (dark gray bars) and on day 7 (black bars) by microscopy. Complete media for this experiment was IMDM (Lonza), Glutamaxx (Life Tech), 20% FBS (Life Tech), 2.5 ug/ml human albumin (Octapharma), 0.5 ug/ml Inositol (Sigma).

In FIG. 12A, NK-92 cells were associated (2 rightmost groups) or not (3 leftmost groups) with IL-15$^{WT}$/sushi-Fc protein gels (Backpacks). First 4 groups were frozen in serum-free media (Bambanker) for 2 hours, fifth group was washed and cultured in complete media (IL-15$^{WT}$/sushi-Fc Backpacks (no freezing)). Upon thawing of 4 leftmost groups, first group was cultured in complete media (Media only), second group was cultured in IL-2 containing (20 ng/ml) complete media (IL-2 (soluble)), third group was cultured in IL-15$^{WT}$/sushi-Fc containing (12 ug/ml) complete media (IL-15$^{WT}$/sushi-Fc (12 ug/ml)) and fourth group was cultured in complete media (IL-15$^{WT}$/sushi-Fc Backpacks). The number of live cells was measured on day 1 (light gray bars), on day 5 (dark gray bars) and on day 6 (black bars) by microscopy. In FIG. 12B, primary NK cells were associated (rightmost group) or not (3 leftmost groups) with IL-15$^{N72D}$/sushi-Fc protein nanogel (Backpacks) before freezing in serum-free media (Bambanker) for 2 weeks. Upon thawing, first group was cultured in complete media (Media only), second group was cultured in IL-2 containing (20 ng/ml) complete media (IL-2 (soluble)), third group was cultured in IL-15$^{N72D}$/sushi-Fc containing (0.6 ug/ml) complete media (IL-15$^{N72D}$/sushi-Fc (0.6 ug/ml)) and fourth group was cultured in complete media (IL-15$^{N72D}$/sushi-Fc Backpacks). The number of live cells was measured after 16 hours (gray bars) and on day 9 (black bars) by flow cytometry. Complete media for this experiment was Xvivo10 containing recombinant transferrin (Lonza), Glutamaxx (Life Tech), 5% human serum AB (Corning).

In FIG. 13A, CD3 T cells were associated (rightmost group) or not (3 leftmost groups) with IL-15N72D/sushi-Fc protein nanogels (Backpacks) before freezing in serum-free media (Bambanker) for 2 weeks. Upon thawing, the first group was cultured in complete media (Media only), the second group was cultured in IL-2 containing (20 ng/ml) complete media (IL-2 (soluble)), the third group was cultured in IL-15N72D/sushi-Fc containing (0.6 ug/ml) complete media (IL-15N72D/sushi-Fc (0.6 ug/ml)) and the fourth group was cultured in complete media (IL-15N72D/sushi-Fc Backpacks). After 9 days in culture, CD3 T cells were analyzed by flow cytometry for expression of subset (FIG. 13A) and activation (FIG. 13B) markers.

In FIG. 14A, CD3 T cells were associated (rightmost group) or not (3 leftmost groups) with IL-15$^{N72D}$/sushi-Fc protein nanogels (Backpacks) before freezing in serum-free media (Bambanker) for 2 weeks. Upon thawing, the first group was cultured in complete media (Media only), the second group was cultured in IL-2 containing (20 ng/ml) complete media (IL-2 (soluble)), the third group was cultured in IL-15$^{N72D}$/sushi-Fc containing (0.6 ug/ml) complete media (IL-15$^{N72D}$/sushi-Fc (0.6 ug/ml)) and the fourth group was cultured in complete media (IL-15$^{N72D}$/sushi-Fc Backpacks). After 1 day in culture, CD3 T cells were co-cultured with target cells (Daudi) at different effector to target (E:T) ratios. Killing of target cells was measured by flow cytometry after 16 hours. Statistical significance was calculated by 2-way ANOVA with Tukey's multiple comparison test. *: p<0.05; : p<0.01. FIG. 14B shows measurements of IFNg release from same cells as in FIG. 14A**. Complete media for this experiment was IMDM (Lonza), Glutamaxx (Life Tech), 20% FBS (Life Tech), 2.5 ug/ml human albumin (Octapharma), 0.5 ug/ml Inositol (Sigma).

In FIG. 15A, CD8 T cells were associated with IL-15$^{N72D}$/sushi-Fc protein nanogels (Backpacks) and either washed and cultured in complete media or frozen in serum-free media (Bambanker) for 2 days. Upon thawing, CD8 T cells were cultured in complete media. After 18 days in culture (20 days for "No freezing" group), CD8 T cells were co-cultured with target cells (Daudi) at different effector to target (E:T) ratios. Killing of target cells was measured by flow cytometry after 16 hours. Statistical significance was calculated by 2-way ANOVA with Sidak's multiple comparison test. n.s.: non-significant. FIG. 15B shows measurements of IFNg release from same cells as in FIG. 15A. Complete media for this experiment was IMDM (Lonza), Glutamaxx (Life Tech), 20% FBS (Life Tech), 2.5 ug/ml human albumin (Octapharma), 0.5 ug/ml Inositol (Sigma).

In FIG. 16A, CD8 T cells were associated (rightmost group) or not (2 leftmost groups) with IL-15$^{N72D}$/sushi-Fc protein nanogels (Backpacks) and either washed and cultured in IL-2 (20 ng/ml) containing media (leftmost group) or frozen in FBS+ 5% DMSO (2 rightmost groups) overnight. Upon thawing, both groups were cultured in IL-2 containing media (20 ng/ml). After 3 days in culture, CD8 T cells were co-cultured with target cells (Daudi) at different effector to target (E:T) ratios. Killing of target cells was measured by flow cytometry after 16 hours. Statistical significance was calculated by 2-way ANOVA with Sidak's multiple comparison test. **: p<0.0001. FIG. 16B shows measurements of IFNg release from same cells as in FIG. 16A**. Complete media for this experiment was IMDM (Lonza), Glutamaxx (Life Tech), 20% FBS (Life Tech), 2.5 ug/ml human albumin (Octapharma), 0.5 ug/ml Inositol (Sigma).

In FIG. 17A, NK cells were conjugated (rightmost group) or not (3 leftmost groups) with IL-15$^{N72D}$/sushi-Fc Backpacks before freezing in serum-free media (Bambanker) for 2 weeks. Upon thawing, first group was cultured in complete media (Media only), second group was cultured in IL-2 containing (20 ng/ml) complete media (IL-2 (soluble)), third group was cultured in IL-15$^{N72D}$/sushi-Fc containing (0.6 ug/ml) complete media (IL-15$^{N72D}$/sushi-Fc (0.6 ug/ml)) and fourth group was cultured in complete media (IL-15$^{N72D}$/sushi-Fc Backpacks). After 1 day in culture, NK cells were co-cultured with target cells (Daudi) at different effector to target (E:T) ratios. Killing of target cells was measured by flow cytometry after 16 hours. FIG. 17B shows measurements of IFNg release from same cells as in FIG. 17A. Complete media for this experiment was Xvivo10 containing recombinant transferrin (Lonza), Glutamaxx (Life Tech), 5% human serum AB (Corning).

In FIG. 18A, in vitro activated T cells (see Example 14) were incubated (on day 0) with Hank's Balanced Salt Solution (HBSS; black bars) or conjugated with IL-15$^{MUT}$/sushi-Fc2 Da backpacks (gray bars) or conjugated with IL-15$^{WT}$/sushi-Fc2 Da backpacks (gray hatched bars). IL-15$^{MUT}$/sushi-Fc2 Da backpacks carry a D8N mutation within the IL15 protein, which renders it inactive. After washing (see Example 21), T cells were split in half and either cultured in CM-mT (see Example 31) or frozen in serum-free media (Bambanker) for 5 days. T cell viability was measured post-thawing and after 2 days in culture by dual-fluorescence microscopy (Acridine Orange/Propidium Iodide, Cat. CS2-0106; Cellometer, Nexcelom Biosciences LLC). NA: not applicable. F/T: freeze/thaw. BP: backpacks. In FIG. 18B, the same experiment was repeated by an independent operator but without IL-15$^{MUT}$/sushi-Fc2 Da backpacks and by keeping the T cells in culture for 3 days instead of 2.

In FIG. 20A, T cells were cultured fresh, without freezing, in FIG. 20B, T cells were frozen (in 90% FBS+10% DMSO) for 7 days, thawed and cultured for 7 more days. In both panels, culture conditions did not include cytokines. The number of live cells was measured at the indicated time points by flow cytometry. Results are reported as fold-change over day 0. BP: backpacks.

In FIG. 21A, activated T cells were conjugated with IL-15$^{MUT}$/sushi-Fc2 Da or IL-15$^{WT}$/sushi-Fc2 Da backpacks and frozen (Bambanker). In FIG. 21B, activated T cells were incubated with Hank's Balanced Salt Solution (HBSS) or conjugated IL-15$^{WT}$/sushi-Fc2 Da backpacks and frozen (Bambanker). Upon thawing, T cells were washed and injected intravenously, $10^7$ per mouse. The number of live cells was measured on day 5 (FIG. 21A) or day 7 (FIG. 21B) by flow cytometry. The two experiments have been performed by independent operators. Results are reported as number of T cells per ul of blood. Statistical analysis by Mann-Whitney test. BP: backpacks.

DETAILED DESCRIPTION

Figure 1A:
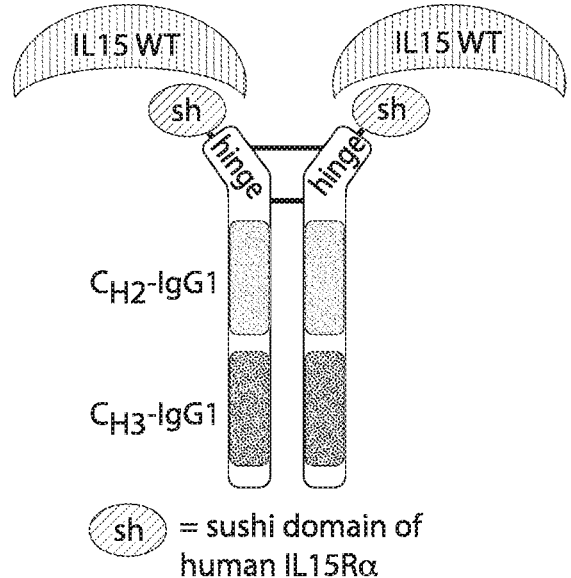
FIGS. 1A-1B depict a schematic of IL-15/sushi-Fc fusion constructs.

Disclosed herein are optimized methods and compositions (also referred to herein as "backpack pillows") to produce (e.g., ex vivo) nucleated cells, e.g., immune cells, having at least one conserved function (e.g., having one or more of viability, proliferation, and cytotoxic activity or activation conserved). In some embodiments, disclosed herein are methods for conserving immune cell function. The method includes contacting a nucleated cell, e.g., an immune cell (e.g., ex vivo contacting, e.g., a population of immune cells obtained from a subject), with a particle, e.g., a nanoparticle, that comprises a conservation agent, e.g., nanoparticle that comprises a protein (e.g., a protein nanogel).

As used herein, a "conservation agent" refers to an agent, e.g., a protein, that that promotes, e.g., conserves or enhances one or more of viability of a nucleated cell, the ability of a nucleated cell to proliferate, or another biological activity of the nucleated cell, e.g., cytotoxic activity, activation of the nucleated cell (e.g., in the context of an immune cell, activation includes an increase in one or more of: immune cell proliferation, cytokine secretion, or target cell killing), the ability to secrete a factor, e.g., a cytokine, e.g., a pro-inflammatory cytokine. In an embodiment, the conservation agent promotes the ability to secrete interferon gamma.

In embodiments, said conservation agent is chosen from one or more (e.g., 2, 3, 4, 5 or more) therapeutic or biologically-active proteins, e.g., one or more cytokine molecules (e.g., an IL-15 IL-2, IL-7, and IL-21, including a variant form thereof, e.g., a mutant; a complex comprising the cytokine molecule with a polypeptide, e.g., a cytokine receptor complex; a fusion or an agonist form thereof); growth factors; and other molecules, e.g., an agonist, e.g., antibody molecule or ligand against a costimulatory molecule such as OX40, CD28, GITR, VISTA, CD40, CD3, or an agonist of CD137. In some embodiments, the conservation agent includes a fusion, e.g., a fusion of a cytokine with an immunoglobulin Fc region, or an antibody molecule (e.g., an immunoglobulin Fab or scFv fragment, a Fab fragment, a $FAB_2$ fragment, or an affibody fragment or derivative, e.g. a sdAb (nanobody) fragment, a heavy chain antibody fragment, single-domain antibody, a bi-specific or multispecific antibody).

Alternatively, or in combination, the backpack pillow includes one or more of: an antibody molecule (e.g., an antibody molecule as described herein), human serum albumin, or other binding moieties, including, e.g., fibronectin molecules, darpins, receptor ectodomains, aptamers, or binding peptides. In embodiments, the therapeutic protein is covalently coupled, e.g., crosslinked, to the nanoparticle, e.g., via a degradable linker (e.g., disulfide linker). Thus, the methods and compositions disclosed herein can provide a significant benefit for cellular therapy, e.g., immunotherapy.

Definitions

Certain terms are defined herein below. Additional definitions are provided throughout the application.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

The term "autologous" refers to any material derived from the same individual to whom it is later to be re-introduced into the individual.

The term "allogeneic" refers to any material derived from a different animal of the same species as the individual to whom the material is introduced.

"Acquire" or "acquiring" as the terms are used herein, refer to obtaining possession of a physical entity (e.g., a sample, a cell or cell population, a polypeptide, a nucleic acid, or a sequence), or a value, e.g., a numerical value, by "directly acquiring" or "indirectly acquiring" the physical entity or value. In one embodiment, acquiring refers to obtaining or harvesting a cell or cell population (e.g., an immune effector cell or population as described herein). "Directly acquiring" means performing a process (e.g., performing a synthetic or analytical or purification method) to obtain the physical entity or value. "Indirectly acquiring" refers to receiving the physical entity or value from another party or source (e.g., a third party laboratory that directly acquired the physical entity or value).

"Immune cell," as that term is used herein, refers to a cell that is involved in an immune response, e.g., in the promotion of an immune response. In some embodiments, the immune cell is an immune effector cell. Examples of immune effector cells include, but are not limited to, T cells, e.g., CD4+ and CD8+ T cells, alpha/beta T cells and gamma/delta T cells, B cells, natural killer (NK) cells, natural killer T (NKT) cells, and mast cells. "Immune cell" also refers to modified versions of cells involved in an immune response, e.g. modified NK cells, including NK cell line NK-92 (ATCC cat. No. CRL-2407), haNK (an NK-92 variant that expresses the high-affinity Fc receptor FcγRIIIa (158V)) and taNK (targeted NK-92 cells transfected with a gene that expresses a CAR for a given tumor antigen), e.g., as described in Klingemann et al. supra.

"Cytotoxic T lymphocytes" (CTLs) as used herein refer to T cells that have the ability to kill a target cell. CTL activation can occur when two steps occur: 1) an interaction between an antigen-bound WIC molecule on the target cell and a T cell receptor on the CTL is made; and 2) a costimulatory signal is made by engagement of costimulatory molecules on the T cell and the target cell. CTLs then recognize specific antigens on target cells and induce the destruction of these target cells, e.g., by cell lysis.

"Tumor infiltrating lymphocytes" (TILs) are used herein refer to lymphocytes that have migrated into a tumor. In embodiments, TILs can be cells at different stages of maturation or differentiation, e.g., TILs can include CTLs, Tregs, and/or effector memory T cells, among other types of lymphocytes.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

A "factor molecule," as used herein refers to a full length naturally occurring wild-type molecule, as well as variants, e.g., functional variants, (e.g., truncations, fragments, mutated (e.g., substantially similar sequences) or derivatized form thereof) having at least 10% of the activity of the naturally occurring molecule. In embodiments the factor molecule has at least 30, 50, or 80% of the activity of the naturally occurring molecule. In an embodiment, a variant has 70, 80, 90 or 95% homology with the corresponding portion of the naturally occurring wild-type molecule. In embodiments, a factor molecule is an antibody molecule, a cytokine molecule, a receptor molecule, a costimulatory molecule.

The term "functional variant" in the context of a polypeptide refers to a polypeptide that is capable of having at least 10% of one or more activities of the naturally-occurring sequence. In some embodiments, the functional variant has substantial amino acid sequence identity to the naturally-occurring sequence, or is encoded by a substantially identical nucleotide sequence, such that the functional variant has one or more activities of the naturally-occurring sequence.

"Antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs).

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

As used herein, a "cytokine molecule" refers to full length, a fragment or a variant of a naturally-occurring, wild type cytokine (including fragments and functional variants thereof having at least 10% of the activity of the naturally-occurring cytokine molecule). In embodiments, the cytokine molecule has at least 30, 50, or 80% of the activity, e.g., the immunomodulatory activity, of the naturally-occurring molecule. In embodiments, the cytokine molecule further comprises a receptor domain, e.g., a cytokine receptor domain, optionally, coupled to an immunoglobulin Fc region. In other embodiments, the cytokine molecule is coupled to an immunoglobulin Fc region. In other embodiments, the cytokine molecule is coupled to an antibody molecule (e.g., an immunoglobulin Fab or scFv fragment, a Fab fragment, a FAB$_2$ fragment, or an affibody fragment or derivative, e.g. a sdAb (nanobody) fragment, a heavy chain antibody fragment, single-domain antibody, a bi-specific or multispecific antibody).

A "cytokine agonist," as used herein can include an agonist of a cytokine receptor, e.g., an antibody molecule (e.g., an agonistic antibody) to a cytokine receptor, that elicits at least one activity of a naturally-occurring cytokine.

"Sample" or "tissue sample" refers to a biological sample obtained from a tissue or bodily fluid of a subject or patient. The source of the tissue sample can be solid tissue as from a fresh, frozen and/or preserved organ, tissue sample, biopsy, or aspirate; blood or any blood constituents (e.g., serum, plasma); bone marrow or any bone marrow constituents; bodily fluids such as urine, cerebral spinal fluid, whole blood, plasma and serum. The sample can include a non-cellular fraction (e.g., urine, plasma, serum, or other non-cellular body fluid). In other embodiments, the body fluid from which the sample is obtained from an individual comprises blood (e.g., whole blood).

The term "subject" includes living organisms in which an immune response can be elicited (e.g., mammals, human). In one embodiment, the subject is a patient, e.g., a patient in need of immune cell therapy. In another embodiment, the subject is a donor, e.g. an allogenic donor of immune cells, e.g., intended for allogenic transplantation.

The term, a "substantially purified cell" refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

Additional definitions are provided throughout the specification.

Conservation Agents

In some embodiments, the conservation agent is a protein, that that promotes, e.g., conserves or enhances one or more of: viability of a nucleated cell (e.g., an immune cell), the ability of a nucleated cell to proliferate, or another biological activity of the nucleated cell, e.g., cytotoxic activity, activation of the nucleated cell, the ability to secrete a factor, e.g., a cytokine, e.g., a pro-inflammatory cytokine. In an embodiment the conservation agent promotes the ability to secrete interferon gamma.

In embodiments, said conservation agent is chosen from one or more (e.g., 2, 3, 4, 5 or more) therapeutic or biologically-active proteins, e.g., one or more cytokine molecules (e.g., an immunostimulatory cytokine, e.g. IL-15, IL-2, IL-7, and IL-21, including a variant, e.g., a mutant forms thereof, or a cytokine complex, e.g., an IL-15 complex as described herein. In some embodiments, the cytokine molecule promotes proliferation, e.g., of immune effector cells such as T or NK cells.

In other embodiments, the conservation agent is a growth factor.

In other embodiments, the conservation agent includes a molecule, e.g., an agonist, e.g., an antibody molecule or a ligand against a costimulatory molecule such as OX40, CD28, GITR, VISTA, CD40, CD3, or an agonist of CD137.

In embodiments, the conservation agent includes an agonist of T cells, e.g., an agonistic antibody or fragment thereof or an activator/agonist of a costimulatory molecule. In embodiments, the agonist of T cells comprises or is a costimulatory molecule. A costimulatory molecule is a cell surface molecule where required, which enhances an efficient response of a lymphocyte, e.g., T cell, to an antigen. In embodiments, a costimulatory molecule is a molecule other than an antigen receptor or its ligands. Without wishing to be bound by theory, costimulation is believed to enhance expansion, survival, and effector function of T cells (e.g., enhance T cell persistence and/or anti-cancer activity. See, e.g., Song et al. BLOOD. 2012; 119(3):696-706). Exemplary costimulatory molecules include but are not limited to CD28, ICOS (CD278), BTLA, LIGHT, HVEM (LIGHTR), CD160 (BY55), OX40, CD27, CD2, CD7, CD40, CD30, 4-1BB (CD137), ICAM-1, B7-1, a toll-like receptor, LFA-1 (CD11a/CD18), GITR, BAFFR, B7-H3, a signaling lymphocytic activation molecules (SLAM protein), SLAMF7, SLAM (SLAMF1, CD150, IPO-3), SLAMF4 (CD244, 2B4), an integrin, IL2R beta, ITGA4, a MHC class I molecule, a TNF receptor, CD49D, CD49f, LFA-1, CD29, CD18, TNFR2, CD84, RANKL, CD229, CD69, CD100 (SEMA4D), and SLAMF6 (NTB-A, Ly108).

In some embodiments, the conservation agent includes an agonist (e.g., an antibody molecule or agonist ligand) against a costimulatory molecule, e.g., OX40, CD28, GITR, VISTA, CD40, CD3, or an agonist of CD137.

In some embodiments, the conservation agent includes a fusion, e.g., a fusion of a cytokine molecule, growth factor or costimulatory molecule with an immunoglobulin Fc region.

Alternatively, or in combination, the conservation agent includes one or more of: an antibody molecule (e.g., an immunoglobulin Fab or scFv fragment, single-domain antibody, a bi-specific or multispecific antibody), human serum albumin, or other binding moieties, including, e.g., fibronectin molecules, darpins, receptor ectodomains, aptamers, or binding peptides.

In some embodiments, the conservation agent includes one or more of: protamine, chitosan carbohydrates, heparan-sulfate proteoglycans, natural polymers, polysaccharides, dextramers, cellulose, fibronectin, collagen, fibrin, or proteoglycans.

In some embodiments, the conservation agent includes one or more (e.g., 2, 3, 4, 5 or more) therapeutic proteins, specifically immunostimulatory cytokines or antibodies (e.g., IL-15, IL-2, IL-7, IL-21, a CD3 agonist, or a CD137 agonist), including mutant or superagonist forms of these cytokines, as well as genetic fusions of such cytokines with immunoglobulin Fc regions, immunoglobulin Fab or scFv fragments, human serum albumin, single-domain antibodies, additional cytokines, bi-specifics, fibronectin, darpins, receptor ectodomains, aptamers, or binding peptides.

Growth Factor Molecules

The methods and compositions, e.g., nanoparticles, described herein can include one or more growth factor molecules. In embodiments, the growth factor molecule is full length, a fragment or a variant of a growth factor, e.g., a growth factor comprising one or more mutations. In embodiments, the growth factor comprises a bone morphogenetic protein (BMP), Leukemia inhibitory factor (LIF), Epidermal growth factor (EGF), an ephrin (e.g., A1, A2, A3, A4, A5, B1, B2, or B3), Erythropoietin (EPO), a Fibroblast growth factor (e.g., FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, or FGF23), GDNF family of ligands Glial cell line-derived neurotrophic factor (GDNF), Growth differentiation factor-9 (GDF9), Hepatocyte growth factor (HGF), Hepatoma-derived growth factor (HDGF), Insulin, an Insulin-like growth factor (e.g., IGF-1 or IGF-2), Keratinocyte growth factor (KGF), Migration-stimulating factor (MSF), Macrophage-stimulating protein (MSP), Myostatin (GDF-8), a Neuregulin (e.g., NRG1, NRG2, NRG3, NRG4), Neurotrophins Brain-derived neurotrophic factor (BDNF), Nerve growth factor (NGF), a Neurotrophin-3 (e.g., NT-3 or NT-4), Placental growth factor (PGF), Platelet-derived growth factor (PDGF), T-cell growth factor (TCGF), Thrombopoietin (TPO, a Transforming growth factor (e.g., TGF-alpha or TGF-beta), or Vascular endothelial growth factor (VEGF), or a fragment or a variant thereof.

Cytokine Molecules

The methods and compositions, e.g., nanoparticles, described herein can include one or more cytokine molecules. In embodiments, the cytokine molecule is full length, a fragment or a variant of a cytokine, e.g., a cytokine comprising one or more mutations. In some embodiments the cytokine molecule comprises a cytokine chosen from interleukin-1 alpha (IL-1 alpha), interleukin-1 beta (IL-1 beta), interleukin-2 (IL-2), interleukin-4 (IL-4), interleukin-5 (IL-5), interleukin-6 (IL-6), interleukin-7 (IL-7), interleukin-12 (IL-12), interleukin-15 (IL-15), interleukin-17 (IL-17), interleukin-18 (IL-18), interleukin-21 (IL-21), interleukin-23 (IL-23), interferon (IFN) alpha, IFN beta, IFN gamma, tumor necrosis alpha, GM-CSF, GCSF, or a fragment or variant thereof, or a combination of any of the aforesaid cytokines. In other embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), interleukin-23 (IL-23) or interferon gamma, or a fragment or variant thereof, or a combination of any of the aforesaid cytokines. The cytokine molecule can be a monomer or a dimer.

In embodiments, the cytokine molecule further comprises a receptor domain, e.g., a cytokine receptor domain. In one embodiment, the cytokine molecule comprises an IL-15 receptor, or a fragment thereof (e.g., an extracellular IL-15 binding domain of an IL-15 receptor alpha) as described herein. In some embodiments, the cytokine molecule is an IL-15 molecule, e.g., IL-15 or an IL-15 superagonist as described herein. As used herein, a "superagonist" form of a cytokine molecule shows increased activity, e.g., by at least 10%, 20%, 30%, compared to the naturally-occurring cytokine. An exemplary superagonist is an IL-15 SA. In some embodiments, the IL-15 SA comprises a complex of IL-15 and an IL-15 binding fragment of an IL-15 receptor, e.g., IL-15 receptor alpha or an IL-15 binding fragment thereof, e.g., as described herein.

In other embodiments, the cytokine molecule further comprises an antibody molecule, e.g., an immunoglobulin Fab or scFv fragment, a Fab fragment, a $FAB_2$ fragment, or an affibody fragment or derivative, e.g. a sdAb (nanobody) fragment, a heavy chain antibody fragment, e.g., an Fc region, single-domain antibody, a bi-specific or multispecific antibody). In one embodiment, the cytokine molecule further comprises an immunoglobulin Fc or a Fab.

In some embodiments, the cytokine molecule is an IL-2 molecule, e.g., IL-2 or IL-2-Fc.

In other embodiments, a cytokine agonist can be used in the methods and compositions disclosed herein. In embodiments, the cytokine agonist is an agonist of a cytokine receptor, e.g., an antibody molecule (e.g., an agonistic antibody) to a cytokine receptor, that elicits at least one activity of a naturally-occurring cytokine. In embodiments, the cytokine agonist is an agonist of a cytokine receptor, e.g., an antibody molecule (e.g., an agonistic antibody) to a cytokine receptor chosen from an IL-15Ra or IL-21R.

IL-15 Molecules

In some embodiments, the cytokine molecule is an IL-15 molecule, e.g., a full length, a fragment or a variant of IL-15, e.g., human IL-15. In embodiments, the IL-15 molecule is a wild-type, human IL-5, e.g., having the amino acid sequence of SEQ ID NO: 1. In other embodiments, the IL-15 molecule is a variant of human IL-5, e.g., having one or more amino acid modifications.

In some embodiments, the IL-15 molecule comprises a mutation, e.g., an N72D point mutation as shown in SEQ ID NO: 6 herein. In some embodiments, the IL-15 molecule comprises a sequence having at least 80%, 85%, 90%, 95%, 96%, 97%, 98%, or 99% identity to SEQ ID NO: 6, wherein the sequence comprises an N72D mutation relative to wild-type human IL-15, and having IL-15Ra binding activity.

In other embodiments, the cytokine molecule further comprises a receptor domain, e.g., an extracellular domain of an IL-15R alpha, optionally, coupled to an immunoglobulin Fc or an antibody molecule. In embodiments, the cytokine molecule is an IL-15 superagonist (IL-15SA) as described in WO 2010/059253. In some embodiments, the cytokine molecule comprises IL-15 and a soluble IL-15 receptor alpha domain fused to an Fc (e.g., a sIL-15Ra-Fc fusion protein), e.g., as described in Rubinstein et al *PNAS* 103:24 p. 9166-9171 (2006).

The IL-15 molecule can further comprise a polypeptide, e.g., a cytokine receptor, e.g., a cytokine receptor domain, and a second, heterologous domain. In one embodiment, the heterologous domain is an immunoglobulin Fc region. In other embodiments, the heterologous domain is an antibody molecule, e.g., a Fab fragment, a Fab$_2$ fragment, a scFv fragment, or an affibody fragment or derivative, e.g. a sdAb (nanobody) fragment, a heavy chain antibody fragment. In some embodiments, the polypeptide also comprises a third heterologous domain. In some embodiments, the cytokine receptor domain is N-terminal of the second domain, and in other embodiments, the cytokine receptor domain is C-terminal of the second domain.

The wild-type IL-15 Receptor alpha sequence and fragment and variants of this sequence are set out below.

```
Wild-type IL-15 Receptor alpha sequence
(Genbank Acc. No. AAI21141.1)
                                       (SEQ ID NO: 2)
MAPRRARGCRTLGLPALLLLLLLRPPATRGITCPPPMSVEHADIWVKSY

SLYSRERYICNSGFKRKAGTSSLTECVLNKATNVAHWTTPSLKCIRDPA

LVHQRPAPPSTVTTAGVTPQPESLSPSGKEPAASSPSSNNTAATTAAIV

PGSQLMPSKSPSTGTTEISSHESSHGTPSQTTAKNWELTASASHQPPGV

YPQGHSDTTVAISTSTVLLCGLSAVSLLACYLKSRQTPPLASVEMEAME

ALPVTWGTSSRDEDLENCSHHL
```

```
Wild-type IL-15 Receptor alpha extracellular
domain (portion of accession number Q13261):
                                       (SEQ ID NO: 3)
MAPRRARGCRTLGLPALLLLLLLRPPATRGITCPPPMSVEHADIWVKSY

SLYSRERYICNSGFKRKAGTSSLTECVLNKATNVAHWTTPSLKCIRDPA

LVHQRPAPPSTVTTAGVTPQPESLSPSGKEPAASSPSSNNTAATTAAIV

PGSQLMPSKSPSTGTTEISSHESSHGTPSQTTAKNWELTASASHQPPGV

YPQGHSDTT
```

```
Isoform CRA_d IL-15 Receptor alpha extracellular
domain (portion of accession number EAW86418):
                                       (SEQ ID NO: 4)
MAPRRARGCRTLGLPALLLLLLLRPPATRGITCPPPMSVEHADIWVKSY

SLYSRERYICNSGFKRKAGTSSLTECVLNKATNVAHWTTPSLKCIKPAA

SSPSSNNTAATTAAIVPGSQLMPSKSPSTGTTEISSHESSHGTPSQTTA

KNWELTASASHQPPGVYPQGHSDTT
```

The wild-type IL-15 Receptor alpha sequence is provided above as SEQ ID NO: 4. IL-15 receptor alpha contains an extracellular domain, a 23 amino acid transmembrane segment, and a 39 amino acid cytoplasmic tail. The extracellular domain of IL-15 Receptor alpha is provided as SEQ ID NO: 3.

In other embodiments, an IL-15 agonist can be used. For example, an agonist of an IL-15 receptor, e.g., an antibody molecule (e.g., an agonistic antibody) to an IL-15 receptor, that elicits at least one activity of a naturally-occurring cytokine.

In embodiments, the IL-15 receptor or fragment thereof is from human or a non-human animal, e.g., mammal, e.g., non-human primate.

The compositions and methods herein can comprise a portion of IL-15Ra, e.g., a Sushi domain of IL-15Ra. In some embodiments, a polypeptide comprises a Sushi domain and a second, heterologous domain. In some embodiments, the polypeptide also comprises a third heterologous domain. In some embodiments, the Sushi domain is N-terminal of the second domain, and in other embodiments, the Sushi domain is C-terminal of the second domain. In embodiments, the second domain comprises an Fc domain.

Fragments and variants of the IL-15 Receptor alpha sequence are set out below.

```
Minimal Sushi domain, wild-type:
                                       (SEQ ID NO: 7)
cpppmsvehadiwvksyslysreryicnsgfkrkagtssltecvlnkatn vahwttpslkci
```

```
Extended Sushi domain, wild-type:
                                       (SEQ ID NO: 8)
itcpppmsvehadiwvksyslysreryicnsgfkrkagtssltecvlnka tnvahwttpslkcir
```

```
Minimal Sushi domain, L77I:
                                       (SEQ ID NO: 9)
cpppmsvehadiwvksyslysreryicnsgfkrkagtssltecvinkatn vahwttpslkci
```

Extended Sushi domain, L77I:

(SEQ ID NO: 10)
itcpppmsvehadiw=vksyslysreryicnsgfkrkagtssltecvinka
tnvahwttpslkcir The wild-type and L77I mutant forms of the sushi domain showed similar activity in one or more of the assays described herein.

The wild-type IL-15 Receptor alpha sequence is provided herein as SEQ ID NO: 2. IL-15 receptor alpha contains an extracellular domain, a 23 amino acid transmembrane segment, and a 39 amino acid cytoplasmic tail. The extracellular domain of IL-15 Receptor alpha is provided as SEQ ID NO: 3. The extracellular domain of IL-15 Receptor alpha comprises a domain referred to as the Sushi domain, which binds IL-15. The Sushi domain is provided as a 62 amino acid minimal domain (SEQ ID NO: 7) and a 65 amino acid extended domain (SEQ ID NO: 8), which comprises the minimal domain.

A Sushi domain as described herein may comprise one or more mutations relative to a wild-type Sushi domain. For instance, residue 77 of IL-15Ra is leucine in the wild-type gene, but can be mutated to isoleucine (L77I). Accordingly, a minimal Sushi domain comprising L77I (with the numbering referring to wild-type IL-15Ra of SEQ ID NO: 2) is provided as SEQ ID NO: 9. An extended Sushi domain comprising L77I (with the numbering referring to the wild-type IL-15Ra of SEQ ID NO: 4) is provided as SEQ ID NO: 10.

In some embodiments, the IL-15Ra portion of the polypeptide consists of 62-171 amino acids of SEQ ID NO: 3 or a sequence having at least 80%, 85%, 90%, 95%, 96%, 97%, 98%, or 99% identity thereto, and having IL-15 binding activity. In some embodiments, the IL-15Ra portion of the polypeptide consists of 65-171 amino acids of SEQ ID NO: 3 or a sequence having at least 80%, 85%, 90%, 95%, 96%, 97%, 98%, or 99% identity thereto, and having IL-15 binding activity. In some embodiments, the IL-15Ra portion of the polypeptide consists of up to 171 amino acids of SEQ ID NO: 3 or a sequence having at least 80%, 85%, 90%, 95%, 96%, 97%, 98%, or 99% identity thereto, and having IL-15 binding activity. In some embodiments, the IL-15Ra portion of the polypeptide consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, or 65-70 amino acids of SEQ ID NO: 3 or a sequence having at least 80%, 85%, 90%, 95%, 96%, 97%, 98%, or 99% identity thereto, and having IL-15 binding activity. In some embodiments, the IL-15Ra portion of the polypeptide consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, or 65-70 amino acids of SEQ ID NO: 3. In some embodiments, the Sushi domain consists of an amino acid sequence of SEQ ID NO: 7 or SEQ ID NO: 8.

In some embodiments, the IL-15Ra portion of the polypeptide consists of 62-171 amino acids of SEQ ID NO: 3 or a sequence having up to 1, 2, 3, 4, 5, 6, 7, 8, 9, 10, 15, 20, 25, 30, 35, or 40 modifications (e.g., substitutions) relative thereto, and having IL-15 binding activity. In some embodiments, the IL-15Ra portion of the polypeptide consists of up to 171 amino acids of SEQ ID NO: 3 or a sequence having up to 1, 2, 3, 4, 5, 6, 7, 8, 9, 10, 15, 20, 25, 30, 35, or 40 modifications (e.g., substitutions) relative thereto, and having IL-15 binding activity. In some embodiments, the IL-15Ra portion of the polypeptide consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, or 65-70 amino acids of SEQ ID NO: 3 or a sequence having up to 1, 2, 3, 4, 5, 6, 7, 8, 9, 10, 15, 20, 25, 30, 35, or 40 modifications (e.g., substitutions) relative thereto, and having IL-15 binding activity.

In some embodiments, the IL-15Ra portion of the polypeptide comprises at least 62 amino acids of SEQ ID NO: 3 or a sequence having at least 80%, 85%, 90%, 95%, 96%, 97%, 98%, or 99% identity thereto, wherein the sequence comprises an L77I mutation relative to wild-type IL-15Ra, and having IL-15 binding activity. In some embodiments, the IL-15Ra portion of the polypeptide comprises at least 65 amino acids of SEQ ID NO: 3 or a sequence having at least 80%, 85%, 90%, 95%, 96%, 97%, 98%, or 99% identity thereto, wherein the sequence comprises an L77I mutation relative to wild-type IL-15Ra, and having IL-15 binding activity. In some embodiments, the IL-15Ra portion of the polypeptide comprises a portion of SEQ ID NO: 3 or a sequence having at least 80%, 85%, 90%, 95%, 96%, 97%, 98%, or 99% identity thereto, wherein the sequence comprises an L77I mutation relative to wild-type IL-15Ra, and having IL-15 binding activity. In some embodiments, the Sushi domain comprises an amino acid sequence of SEQ ID NO: 9 or SEQ ID NO: 10.

In some embodiments, the IL-15Ra portion of the polypeptide comprises at least 62 amino acids of SEQ ID NO: 3 or a sequence having up to 1, 2, 3, 4, 5, 6, 7, 8, 9, 10, 15, 20, 25, 30, 35, or 40 modifications (e.g., substitutions) relative thereto, wherein the sequence comprises an L77I mutation relative to wild-type IL-15Ra, and having IL-15 binding activity. In some embodiments, the IL-15Ra portion of the polypeptide comprises a portion of SEQ ID NO: 3 or a sequence having up to 1, 2, 3, 4, 5, 6, 7, 8, 9, 10, 15, 20, 25, 30, 35, or 40 modifications (e.g., substitutions) relative thereto, wherein the sequence comprises an L77I mutation relative to wild-type IL-15Ra, and having IL-15 binding activity.

In embodiments, the IL-15Ra portion of the polypeptide comprises at least 10, 20, 30, 40, 50, 60, 62, 65, 70, 80, 90, 100, 110, 120, 130, 140, 150, or 160 consecutive amino acids of SEQ ID NO: 3, or a sequence having an L77I mutation relative thereto. In embodiments, the IL-15Ra portion of the polypeptide consists of 10-20, 20-30, 30-40, 40-50, 50-60, 60-70, 70-80, 80-90, 90-100, 100-110, 110-120, 120-130, 130-140, 140-150, 150-160, or 160-170 consecutive amino acids of SEQ ID NO: 3, or a sequence having an L77I mutation relative thereto.

In embodiments, the Sushi domain is a Sushi domain from human or a non-human animal, e.g., mammal, e.g., non-human primate.

In embodiments, the composition comprises, e.g., the nanoparticle and/or the conservation agent comprises, an IL-15 complex, the IL-15 complex comprising an IL-15 molecule complexed, e.g., covalently or noncovalently, with a polypeptide, wherein the polypeptide comprises a first domain comprising:

i) at least 62 amino acids of the wild-type IL-15 Receptor alpha extracellular domain of SEQ ID NO: 3, wherein the longest contiguous IL-15 receptor alpha sequence of the polypeptide is no more than 171 amino acids in length, or a sequence having at least 80%, 85%, 90%, 95%, 96%, 97%, 98%, or 99% identity thereto, and having IL-15 binding activity;

ii) at least 62 amino acids of SEQ ID NO: 3, wherein the longest contiguous IL-15 receptor alpha sequence of the polypeptide is no more than 171 amino acids in length, or a sequence that differs by no more than 1, 2, 3, 4, or 5 amino acids from the corresponding sequence of SEQ ID NO: 3, and having IL-15 binding activity;

iii) at least 62 amino acids of SEQ ID NO: 3, wherein the longest contiguous IL-15 receptor alpha sequence of the polypeptide is no more than 171 amino acids in length, and having IL-15 binding activity;

iv) an active fragment, e.g., an IL-15 binding fragment, of the minimal sushi domain and no more than 171 contiguous amino acid residues of SEQ ID NO: 3, or a sequence having at least 80%, 85%, 90%, 95%, 96%, 97%, 98%, or 99% identity thereto;

v) an active fragment, e.g., an IL-15 binding fragment, of the minimal sushi domain and no more than 171 contiguous amino acid residues of SEQ ID NO: 3, or a sequence that differs by no more than 1, 2, 3, 4, or 5 amino acids from the corresponding sequence of SEQ ID NO: 3;

vi) an active fragment, e.g., an IL-15 binding fragment, of the minimal sushi domain and no more than 171 contiguous amino acid residues of SEQ ID NO: 3;

vii) an active fragment, e.g., an IL-15 binding fragment, of the extended sushi domain and no more than 171 contiguous amino acid residues of SEQ ID NO: 3, or a sequence having at least 80%, 85%, 90%, 95%, 96%, 97%, 98%, or 99% identity thereto;

viii) an active fragment, e.g., an IL-15 binding fragment, of the extended sushi domain and no more than 171 contiguous amino acid residues of SEQ ID NO: 3, or a sequence that differs by no more than 1, 2, 3, 4, or 5 amino acids from the corresponding sequence of SEQ ID NO: 3;

ix) an active fragment, e.g., an IL-15 binding fragment, of the extended sushi domain and no more than 171 contiguous amino acid residues of SEQ ID NO: 3; or x) at least 62 amino acids of SEQ ID NO: 3, or a sequence having at least 80%, 85%, 90%, 95%, 96%, 97%, 98%, or 99% identity thereto, having IL-15 binding activity, and wherein amino acid 77 (with numbering referring to the wild-type IL-15 receptor alpha of SEQ ID NO: 4) is isoleucine;

xi) at least 62 amino acids of SEQ ID NO: 3, or a sequence that differs by no more than 1, 2, 3, 4, or 5 amino acids from the corresponding sequence of SEQ ID NO: 3, having IL-15 binding activity, and wherein amino acid 77 is isoleucine;

xii) at least 62 amino acids of SEQ ID NO: 3 having IL-15 binding activity, and wherein amino acid 77 is isoleucine;

xiii) an active fragment, e.g., an IL-15 binding fragment, of the minimal or extended sushi domain, or a sequence having at least 80%, 85%, 90%, 95%, 96%, 97%, 98%, or 99% identity thereto, wherein amino acid 77 is isoleucine;

xiv) an active fragment, e.g., an IL-15 binding fragment, of the minimal or extended sushi domain, or a sequence that differs by no more than 1, 2, 3, 4, or 5 amino acids from the corresponding sequence of SEQ ID NO: 3, wherein amino acid 77 is isoleucine; or xv) an active fragment, e.g., an IL-15 binding fragment, of the minimal or extended sushi domain, wherein amino acid 77 is isoleucine.

and optionally, a second, heterologous domain, e.g., an Fc domain or a Fab domain.

In some embodiments, the polypeptide comprising the IL-15 receptor or fragment thereof comprises an Fc domain. In embodiments, the Fc domain is an effector-attenuated Fc domain, e.g., a human IgG2 Fc domain, e.g., a human IgG2 domain of SEQ ID NO: 11 or an amino acid sequence having at least 80%, 85%, 90%, 95%, 96%, 97%, 98%, or 99% identity thereto.

(SEQ ID NO: 11)
ERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEY

KCKVSNKGLPAPIEKTISKTKGQPREPQVYTLPPSREEMTKNQVSLTCLV

KGFYPSDIAVEWESNGQPENNYKTTPPMLDSDGSFFLYSKLTVDKSRWQQ

GNVFSCSVMHEALHNHYTQKSLSLSPGK

In embodiments, the effector-attenuated Fc domain has reduced effector activity, e.g., compared to a wild-type IgG1 Fc domain, e.g., compared to a wild-type IgG1 Fc domain of SEQ ID NO: 12. In some embodiments, effector activity comprises antibody-dependent cellular toxicity (ADCC). In embodiments, the effector activity is reduced by 10%, 20%, 30%, 40%, 50%, 60%, 70%, 80%, 90%, 95%, or 99% in an ADCC assay, e.g., compared to a wild-type IgG1 Fc domain of SEQ ID NO: 12. In some embodiments, effector activity comprises complement dependent cytotoxicity (CDC). In embodiments, the effector activity is reduced by 10%, 20%, 30%, 40%, 50%, 60%, 70%, 80%, 90%, 95%, or 99% in a CDC assay such as a CDC assay described in Armour et al., "Recombinant human IgG molecules lacking Fc gamma receptor I binding and monocyte triggering activities." Eur J Immunol (1999) 29:2613-24" e.g., compared to a wild-type IgG1 Fc domain of SEQ ID NO: 12.

In some embodiments, the Fc domain comprises an IgG1 Fc domain of SEQ ID NO: 12 or an amino acid sequence having at least 80%, 85%, 90%, 95%, 96%, 97%, 98%, or 99% identity thereto.

(SEQ ID NO: 12)
EPKSCDKTHTCPPCPAPELLGGPSVFLEPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFELYSKLTVDKS

RWQQGNVFSCSVMHEALHNHYTQKSLSLSPGK

In some embodiments, the Fc domain comprises an IgG2 constant region of SEQ ID NO: 13 or fragment thereof, or an amino acid sequence having at least 80%, 85%, 90%, 95%, 96%, 97%, 98%, or 99% identity thereto.

(SEQ ID NO: 13)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

-continued

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

In some embodiments, the Fc domain comprises an IgG2 Da Fc domain of SEQ ID NO: 14 or an amino acid sequence having at least 80%, 85%, 90%, 95%, 96%, 97%, 98%, or 99% identity thereto. In embodiments, the Fc domain comprises one or both of A330S and P331S mutations using Kabat numbering system. In embodiments, the Fc domain is one described in Armour et al. "Recombinant human IgG molecules lacking Fc gamma receptor I binding and monocyte triggering activities." Eur J Immunol (1999) 29:2613-24.

(SEQ ID NO: 14; IgG2Da-Fc)
ERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEY

KCKVSNKGLPssIEKTISKTKGQPREPQVYTLPPSREEMTKNQVSLTCLV

KGFYPSDIAVEWESNGQPENNYKTTPPMLDSDGSFFLYSKLTVDKSRWQQ

GNVESCSVMHEALHNHYTQKSLSLSPGK

In some embodiments, the Fc domain has dimerization activity.

In some embodiments, the Fc domain is an IgG domain, e.g., an IgG1, IgG2, IgG3, or IgG4 Fc domain. In some embodiments, the Fc domain comprises a CH2 domain and a CH3 domain.

In some embodiments, the nanoparticle comprises a protein having a sequence of SEQ ID NO: 15 or an amino acid sequence having at least 80%, 85%, 90%, 95%, 96%, 97%, 98%, or 99% identity thereto.

(SEQ ID NO: 15; sushi-IgG2Da-Fc)
ITCPPPMSVEHADIWVKSYSLYSRERYICNSGFKRKAGTSSLTECVLNKA

TNVAHWTTPSLKCIRERKCCVECPPCPAPPVAGPSVFLFPPKPKDTLMIS

RTPEVTCVVVDVSHEDPEVQFNWYVDGVEVHNAKTKPREEQFNSTFRVVS

VLTVVHQDWLNGKEYKCKVSNKGLPSSIEKTISKTKGQPREPQVYTLPPS

REEMTKNQVSLTCLVKGFYPSDIAVEWESNGQPENNYKTTPPMLDSDGSF

FLYSKLTVDKSRWQQGNVFSCSVMHEALHNHYTQKSLSLSPGK

In some embodiments, the nanoparticle comprises a sushi domain described herein (e.g., in SEQ ID NO: 7) and an Fc domain described herein, e.g., an IgG2 Fc domain (e.g., SEQ ID NO: 11 or an amino acid sequence having at least 80%, 85%, 90%, 95%, 96%, 97%, 98%, or 99% identity thereto). In some embodiments, the nanoparticle comprises a sushi domain of SEQ ID NO: 7 and an Fc domain described herein, e.g., an IgG1 Fc domain, e.g., an Fc domain of SEQ ID NO: 12 or an amino acid sequence having at least 80%, 85%, 90%, 95%, 96%, 97%, 98%, or 99% identity thereto. In some embodiments, the nanoparticle comprises a sushi domain of SEQ ID NO: 8 and an IgG2 Fc domain, e.g., an Fc domain of SEQ ID NO: 11 or an amino acid sequence having at least 80%, 85%, 90%, 95%, 96%, 97%, 98%, or 99% identity thereto. In some embodiments, the nanoparticle comprises a sushi domain of SEQ ID NO: 8 and an IgG1 Fc domain, e.g., an Fc domain of SEQ ID NO: 12 or an amino acid sequence having at least 80%, 85%, 90%, 95%, 96%, 97%, 98%, or 99% identity thereto.

In some embodiments, the nanoparticle comprises a sushi domain of SEQ ID NO: 7 and an IgG2 Da Fc domain of SEQ ID NO: 14 or an amino acid sequence having at least 80%, 85%, 90%, 95%, 96%, 97%, 98%, or 99% identity thereto. In some embodiments, the nanoparticle comprises a sushi domain of SEQ ID NO: 8 and an IgG2 Da Fc domain of SEQ ID NO: 14 or an amino acid sequence having at least 80%, 85%, 90%, 95%, 96%, 97%, 98%, or 99% identity thereto. In some embodiments, the nanoparticle comprises a sushi-IgG2 Da-Fc protein having a sequence of SEQ ID NO: 15 or an amino acid sequence having at least 80%, 85%, 90%, 95%, 96%, 97%, 98%, or 99% identity thereto.

In embodiments, the IL-15 molecule is a molecule described in International Application WO2017/027843, which is herein incorporated by reference in its entirety.

In some embodiments the conservation agent comprises IL-15SA. The combination of human IL-15 with soluble human IL-15Ra generates a complex termed IL-15 super-agonist (IL-15SA) that possesses greater biological activity than human IL-15 alone.

Soluble human IL-15Ra, as well as truncated versions of the extracellular domain, has been described, e.g., in (Wei et al., 2001, J. of Immunol. 167: 277-282). The amino acid sequence of human IL-15Ra is set forth in SEQ ID NO: 2 herein. Accordingly, some aspects of the disclosure relate to IL-15SA comprising a complex of human IL-15 and soluble human IL-15R molecules. In some aspects of the disclosure, IL-15SA comprises a complex of human IL-15 and soluble human IL-15Ra comprising all or a portion of the extracellular domain, without the transmembrane or cytoplasmic domain. In some aspects of the disclosure, IL-15SA comprises a complex of human IL-15 and soluble human iL-15Ra comprising the full extracellular domain or a truncated form of the extracellular domain which retains IL-15 binding activity. Some aspects of the disclosure relate to IL-15SA comprising a complex of human IL-15 and soluble human IL-15Ra comprising a truncated form of the extracellular domain which retains IL-15 binding activity, such as amino acids 1-60, 1-61, 1-62, 1-63, 1-64 or 1-65 of human IL-15Ra. In some aspects of the disclosure, IL-15SA comprises a complex of human IL-15 and soluble human IL-15Ra comprising a truncated form of the extracellular domain which retains IL-15 binding activity, such as amino acids 1-80, 1-81, 1-82, 1-83, 1-84 or 1-85 of human IL-15Ra. In some aspects of the disclosure, IL-15SA comprises a complex of human IL-15 and soluble human IL-15Ra comprising a truncated form of the extracellular domain which retains IL-15 binding activity, such as amino acids 1-180, 1-181, or 1-182 of human IL-15Ra.

Some aspects of the disclosure relate to IL-15SA comprising a complex of human IL-15 and soluble human IL-15Ra comprising a truncated form of the extracellular domain which retains IL-15 binding activity and comprises a Sushi domain. Truncated forms of soluble human IL-15Ra which retain IL-15 activity and comprise a Sushi domain are useful in IL-15SA of the present disclosure.

Mutant forms of human IL-15 have been described, e.g., in Zhu et al, 2009 J of Immunol. 183:3598. Accordingly, the present disclosure provides any of the foregoing IL-15SA complexes in which human IL-15 is wild-type or mutant IL-15 comprising one or more mutations (e.g., one or more amino acid substitutions, additions or deletions). An exemplary IL-15 mutant having increased biological activity relative to wild-type IL-15 for use in the IL-15SA of the present disclosure comprises an asparagine to aspartic acid substitution at amino acid 72 (N72D).

In any of the foregoing embodiments, the present disclosure relates to a complex comprising soluble human IL-15Ra expressed as a fusion protein, such as an Fc fusion as described herein (e.g., human IgG1 Fc), with IL-15. In some embodiments, IL-15SA comprises a dimeric human IL-15RaFc fusion protein (e.g., human IgG1 Fc) complexed with two human IL-15 molecules.

In some embodiments an IL-15SA cytokine complex comprises an IL-15 molecule comprising an amino acid sequence set forth in SEQ ID NO: 1 or SEQ ID NO: 6 herein. In some embodiments, an IL-15SA cytokine complex comprises an IL-15 molecule comprising an amino acid sequence set forth in SEQ ID NO: 4 or SEQ ID NO: 5 of International Application WO2017/027843, which are herein incorporated by reference. In some embodiments, an IL-15SA cytokine complex comprises a soluble IL-15Ra molecule comprising a sequence of SEQ ID NO: 7, SEQ ID NO: 8, SEQ ID NO: 9, or SEQ ID NO: 10 herein. In some embodiments, an IL-15SA cytokine complex comprises a soluble IL-15Ra molecule comprising a sequence of SEQ ID NO: 3, SEQ ID NO: 7 or SEQ ID NO: 8 of International Application WO2017/027843, which are herein incorporated by reference.

In some embodiments the IL-15SA is a cytokine complex comprising a dimeric IL-15RaFc fusion protein complexed with two IL-15 molecules. In some embodiments, IL-15-SA comprises a dimeric IL-15RaSu (Sushi domain)/Fc (SEQ ID NO: 5) and two IL-15N72D (SEQ ID NO: 6) molecules. In embodiments, the IL-15SA comprises ALT-803, as described in US20140134128, incorporated herein by reference. In some embodiments, the IL-15SA comprises a dimeric IL-15RaSu/Fc molecule (SEQ ID NO: 5) and two IL-15 molecules (SEQ ID NO: 1).

In some embodiments, the IL-15SA comprises a soluble IL-15Ra molecule (e.g., SEQ ID NO: 7 or SEQ ID NO: 8) and two IL-15 molecules (e.g., SEQ ID NO: 1 or SEQ ID NO: 6).

Particles, e.g., Nanogels

Compositions, e.g., nanoparticles (e.g., nanogels) can comprise one or more proteins (e.g., biologically-active proteins, e.g., therapeutic proteins) disclosed herein. Exemplary nanoparticles (e.g., nanogels), and methods of making the same, are described in International published application WO 2010/059253, entitled "Methods and Compositions for Localized Agent Delivery" and International published application WO 2015/048498, entitled "Carrier-Free Biologically-Active Protein Nanoparticles," the contents of both applications are hereby entirely incorporated by reference.

A "particle" as used herein, comprises a plurality of (e.g., at least 2) proteins, e.g., a plurality of cytokine molecules as described herein. In some embodiments, the particles are nanoparticles having a diameter of a range from 1-1000 nanometers (nm). In some embodiments, the diameter of the nanoparticle ranges in size from 20-750 nm, or from 20-500 nm, or from 20-250 nm. In some embodiments, the diameter ranges in size from 50-750 nm, or from 50-500 nm, or from 50-250 nm, or from about 100-300 nm. In some embodiments, the diameter of the nanoparticle is about 100, about 150, about 200, about 250 nm, or about 300 nm. In embodiments, the nanoparticles are substantially spherical.

In embodiments, the nanoparticle has an average hydrodynamic diameter (e.g., measured by dynamic light scattering) between 30 nm and 1200 nm, between 40 nm and 1,100 nm, between 50 nm and 1,000 nanometer, between such as 50-500 nm, more typically, between 70 and 400 nm.

In some embodiments, the nanoparticles comprise, or consist of, a nanogel, e.g., a described herein.

In embodiments, the proteins in the nanoparticle are coupled, e.g., covalently coupled or crosslinked to each other and/or a second component of the particle (e.g., the proteins reversibly linked through a degradable linker). In embodiments, the proteins are present in a polymer or silica, e.g., in a polymer-based or silica shell. In embodiments, the nanoparticle includes a nanoshell as described herein.

In embodiments, the protein is reversibly linked through a degradable linker to a functional group or polymer, or "reversibly modified." The nanoshell can be formed, in some embodiments, by polymerizing functional groups (e.g., silanes) of a protein conjugate with a crosslinker (e.g., silane-PEG-silane) in the presence of a catalyst (e.g., NaF). An example of a protein nanoparticle is a "protein nanogel," which refers to a plurality of proteins crosslinked (e.g., reversibly and covalently crosslinked) to each other through a degradable linker (see, e.g., FIG. 9A of WO2015/048498). In some embodiments, proteins of a nanogel are crosslinked (e.g., reversibly and covalently crosslinked) to a polymer (e.g., a hydrophilic polymer such as polyethylene glycol (PEG); see, e.g., FIG. 9A of WO2015/048498). The polymer, in some embodiments, may be crosslinked to the surface of the nanogel (e.g., to proteins exposed at the surface of the nanogel).

The size of a protein nanogel may be determined at least two ways: based on its "dry size" and based on its "hydrodynamic size." The "dry size" of a protein nanogel refers to the diameter of the nanogel as a dry solid. The "hydrodynamic size" of a protein nanogel refers to the diameter of the nanogel as a hydrated gel (e.g., a nanogel in an aqueous buffer). The dry size of a nanogel may be determined, for example, by transmission electron microscopy, while the hydrodynamic size of the nanogel may be determined, for example, by dynamic light scattering.

In some embodiments, the dry size of a nanogel is less than 400 nm. In some embodiments, the dry size of a nanogel is less than 300 nm, less than 200 nm, less than 100 nm, less than 80 nm, less than 75 nm, less than 70 nm, less than 65 nm, or less than 60 nm. In some embodiments, the dry size of a nanogel is 40 to 90 nm, 40 to 80 nm, 40 to 70 nm, 40 to 60 nm, 50 to 90 nm, 60 to 80 nm, 50 to 70 nm, or 50 to 60 nm. In some embodiments, the dry size of a nanogel is 40 nm, 45 nm, 50 nm, 55 nm, 60 nm, 65 nm, 70 nm, 75 nm, 80 nm, 85 nm, 90 nm or 95 nm.

In some embodiments, the average dry size of a nanoparticle (e.g., nanogel) within a plurality of nanoparticles is less than 400 nm. In some embodiments, the average dry size of a nanoparticle within such a plurality varies by no more than 5% or 10%. In some embodiments, the average dry size of a nanoparticle (e.g., nanogel) within a plurality of nanoparticles is less than 300 nm, less than 200 nm, less than 100 nm, less than 80 nm, less than 75 nm, less than 70 nm, less than 65 nm, or less than 60 nm. In some embodiments, the average dry size of a nanoparticle (e.g., nanogel) within a plurality of nanoparticles is 40 to 90 nm, 40 to 80 nm, 40 to 70 nm, 40 to 60 nm, 50 to 90 nm, 60 to 80 nm, 50 to 70 nm, or 50 to 60 nm. In some embodiments, the dry size of a nanogel is 40 nm, 45 nm, 50 nm, 55 nm, 60 nm, 65 nm, 70 nm, 75 nm, 80 nm, 85 nm, 90 nm or 95 nm.

In some embodiments, the average hydrodynamic size of a nanoparticle (e.g., nanogel) within a plurality of nanoparticles is less than 1000 nm. In some embodiments, the average hydrodynamic size of a nanoparticle within such a plurality has a polydispersity index as measured by dynamic light scattering of less than 0.35. In some embodiments, the average hydrodynamic size of a nanoparticle (e.g., nanogel) within a plurality of nanoparticles is less than 500 nm, less than 400 nm, less than 300 nm, less than 200 nm, or less than 100 nm. In some embodiments, the average hydrodynamic size of a nanoparticle (e.g., nanogel) within a plurality of nanoparticles is 400 to 500 nm, 300 to 400 nm, 200 to 300 nm, 100 to 200 nm, 50 to 100 nm.

In some embodiments, the dry size of the biologically-active protein-polymer nanogels is less than 300 nm in diameter. For example, the dry size of the biologically-active protein-polymer nanogels may be 50-200 nm in diameter. In some embodiments, protein nanogels of a plurality, as provided herein, are of similar dry size (e.g., where 70% of the nanogels are within 10%, 20%, 30%, 40%, 50% or 100% diameter of each other and have a polydispersity index as measured by dynamic light scattering of less than 0.35).

In some embodiments, the hydrodynamic size of the biologically-active protein-polymer nanogels is less than 150 nm in diameter. For example, the hydrodynamic size of the biologically-active protein-polymer nanogels may be 50-100 nm in diameter. In some embodiments, protein nanogels of a plurality, as provided herein, are of similar hydrodynamic size (e.g., where 70% of the nanogels are within 10%, 20%, 30%, 40%, 50% or 100%, diameter of each other and have a polydispersity index as measured by dynamic light scattering of less than 0.35).

In some embodiments, nanoparticles are provided in a dry, solid form, such as a lyophilized form. In other embodiments, nanoparticles are provided in a hydrated form, such as in aqueous or otherwise liquid solution. In other embodiments, nanoparticles are provided in a frozen form.

In some embodiments, proteins of the nanoparticles are reversibly linked to each other through a degradable linker (e.g., a disulfide linker) such that under physiological conditions, the linker degrades and releases the intact, biologically-active protein. In other embodiments, proteins of nanoparticles are reversibly linked to functional groups through a degradable linker such that under physiological conditions, the linker degrades and releases the intact, biologically-active protein. In each instance, the proteins are considered to be reversibly modified, as described below.

A protein that is "reversibly linked to another protein" herein refers to a protein that is attached (e.g., covalently attached) to another protein through a degradable linker. Such proteins are considered to be linked (e.g., crosslinked) to each other through the degradable linker. In some embodiments, nanoparticles (e.g., nanogels) contain a single (e.g., single type of) biologically-active protein (e.g., IL-15, IL-15-Fc, IL-15 Fab fragment, IL-2, or IL-2-Fc, a Fab fragment, a FAB₂ fragment, a scFv fragment, or an affibody fragment or derivative, e.g. a sdAb (nanobody) fragment, a heavy chain antibody fragment etc.), while in other embodiments, nanoparticles contain more than one (e.g., 2, 3, 4, 5 or more) of biologically-active protein (e.g., a combination of different proteins such as IL-2 and IL-15 (or IL-15SA) or IL-15 and IL-21). For example, a protein nanogel may contain a combination of Protein A and Protein B, wherein Protein A is linked to Protein A, Protein A is linked to Protein B and/or Protein B is linked to Protein B.

A protein that is "reversibly linked to a functional group," or a protein that is "reversibly modified," herein refers to a protein that is attached (e.g., covalently attached) to a functional group through a degradable linker. Such a protein may be referred to herein as a "protein conjugate" or a "reversibly modified protein conjugate"—the terms may be used interchangeably herein. It should be understood that proteins and polymers each contain functional groups to which a protein can be linked via a reversible linker (e.g., degradable linker such as a disulfide linker). Examples of protein conjugates and reversibly modified proteins, as provided herein, include without limitation, a protein reversibly linked (e.g., via a degradable linker) to another protein, a protein reversibly linked to a polymer, and a protein reversibly linked to another functional group. It should be understood that the term "protein" includes fusion proteins.

Degradable Linkers

Suitable degradable linkers, e.g., crosslinkers, for the nanoparticles described herein can contain, for example, two N-hydroxysuccinimide (NHS) ester groups joined together by a flexible disulfide-containing linker that is sensitive to a reductive physiological environment, or a hydrolysable linker that is sensitive to an acidic physiological environment (pH<7, for example, a pH of 4-5, 5-6, or 6- to less than 7, e.g., 6.9), or a protease sensitive linker that is sensitive to one or more enzymes present in biological media such as proteases in a tumor microenvironment such a matrix metalloproteases present in a tumor microenvironment or in inflamed tissue (e.g. matrix metalloproteinase 2 (MMP2) or matrix metalloproteinase 9 (MMP9)). A crosslinker sensitive to a reductive physiological environment is, for example, a crosslinker with disulfide containing linker that will react with amine groups on proteins by the presence of NHS groups which cross-link the proteins into high density protein nanogels. The cross-linker used in the Examples herein includes Bis[2-(N-succinimidyl-oxycarbonyloxy)ethyl] disulfide.

In some embodiments, the degradable linker comprises at least one N-hydroxysuccinimide ester. In some embodiments, the degradable linker is a redox responsive linker. In some embodiments, the redox responsive linker comprises a disulfide bond. In some embodiments, the degradable linkers provided herein, comprise at least one N-hydroxysuccinimide ester, which is capable of reacting with proteins at neutral pH (e.g., about 6 to about 8, or about 7) without substantially denaturing the protein. In some embodiments, the degradable linkers are "redox responsive" linkers, meaning that they degrade in the presence of a reducing agent (e.g., glutathione, GSH) under physiological conditions (e.g., 20-40° C. and/or pH 4-8), thereby releasing intact protein from the compound to which it is reversibly linked. An example of a degradable linker for use in accordance with the present disclosure is the following:

Formula I

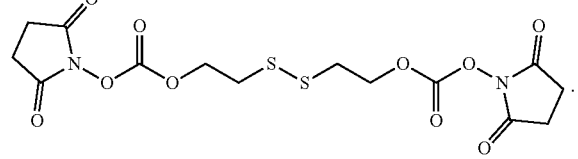

The linker of Formula I contains a disulfide, which is cleaved in the presence of a reducing agent. For example, under physiological conditions, the disulfide bond of the linker of Formula I is cleaved by glutathione.

Proteins may be linked (e.g., covalently linked) to a degradable linker through any terminal or internal —NH₂ functional group (e.g., side chain of a lysine). Thus, an intermediate species formed during the reversible modification of a protein with a degradable linker of Formula I is the following:

Formula II

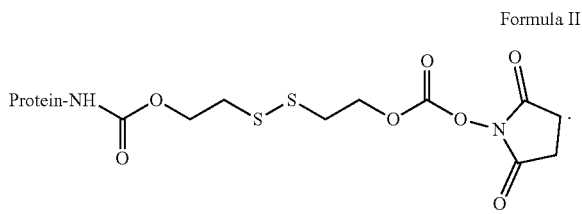

Also provided herein are reversibly modified protein conjugates that comprise Formula III:

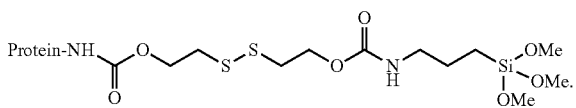

The linkers may be conjugated to the protein of interest at an amine group such as a terminal amine or an internal amine. Internal amines include side chain amines such as lysine amines.

The disclosure further provides protein conjugates comprising Formula III:

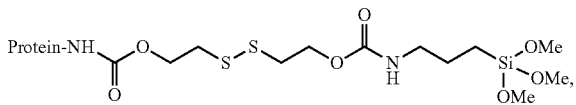

wherein the protein is a cytokine molecule such as, for example, IL-2 or IL-15 molecule.

Silica-based nanoparticles with a high incorporation efficiency (e.g., >~90%) and with high protein drug loading efficiency (e.g., >~80%) are formed by the polymerization of proteins that are reversibly modified with silane. Thus, provided herein are nanoparticles formed by the polymerization of protein conjugates of Formula III with cross-linkers such as, for example, silane-PEG-silane polymers.

In other embodiments, the proteins can be linked by an enzyme-sensitive linker. In embodiments, the linker is degraded or hydrolyzed through the action of an enzyme (e.g., a protease or esterase). In some embodiments, the linker comprises a substrate peptide that is cleaved, e.g., activated, by an enzyme chosen from matrix metalloprotease MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, or TACE. In embodiments, the linker includes a substrate sequence disclosed in U.S. Patent Application No. 2015/0087810, U.S. Pat. Nos. 8,541,203, 8,580,244. In some embodiments, the linker comprises a sequence disclosed in one of the following articles: van Kempen, et al. *Eur Cancer* (2006) 42:728-734; Desnoyers, L. R. et al. *Sci Transl Med* (2013) 5:207; Rice, J. J. et al. *Protein Sci* (2006) 15:825-836; Boulware, K. T. and Daugherty, P. S. *Proc Natl Acad Sci USA* (2006) 103:7583-7588; and Eckhard, U et al *Matrix Biol* (2015) doi: 10.1016/j.matbio.2015.09.003 (epub). The contents of any of the publications referenced herein are hereby expressly incorporated by reference.

Other aspects and embodiments of the nanoparticles are further provided herein.

Reversibly modified proteins provided herein can, in some embodiments, be formed or self-assemble into various nanoparticles including, without limitation, protein-hydrophilic polymer conjugates (e.g., reversibly modified with PEG), protein-hydrophobic polymer conjugates (e.g., reversibly modified PLA or PLGA), bulk crosslinked protein hydrogels, crosslinked protein nanogel particles, protein nanocapsules with different shell materials (e.g., silica), protein-conjugated nanoparticles (e.g., liposome, micelle, polymeric nanoparticles, inorganic nanoparticles), e.g., as described in WO2015/048498. Likewise, proteins crosslinked to each other, as provided herein, in some embodiments, can be formed or can self-assemble into protein nanoparticles.

In some embodiments, protein nanoparticles (e.g., protein nanogels, including protein-polymer nanogels) contain carrier proteins or other carrier molecules. Carrier proteins typically facilitate the diffusion and/or transport of different molecules, and can increase stability of the nanoparticles and/or increase stability of the nanoparticle on the cell surface, and/or increases affinity of the nanoparticle to the cell surface. It should be understood that the term "carrier protein," as used herein, refers to a protein that does not adversely affect a biologically-active protein of a protein nanoparticle. In some embodiments, a carrier protein is an inert protein. In some embodiments, the carrier protein or carrier molecules are chosen from albumin, protamine, chitosan carbohydrates, heparan-sulfate proteoglycans, natural polymers, polysaccharides, dextramers, cellulose, fibronectin, collagen, fibrin, or proteoglycans. Thus, in some embodiments, carrier proteins are not biologically active.

In some embodiments, provided herein is a monodispersed plurality of biologically-active protein-polymer particles, e.g., nanoparticles, e.g., nanogels. In embodiments, the proteins of the nanogels are reversibly and covalently crosslinked to each other through a degradable linker, and wherein proteins of the nanogels are crosslinked to a polymer. In some embodiments, the polymer is crosslinked to the surface of a nanogel (and, thus, is considered to be surface-conjugated).

In some embodiments, a nanoparticle (e.g., nanogel) comprises, consists of, or consists essentially of (a) one or more biologically-active proteins reversibly and covalently crosslinked to each other through a degradable linker (e.g., disulfide linker) and (b) polymers crosslinked to surface-exposed proteins of the nanogel (e.g., reversibly and covalently crosslinked through a degradable linker). In some embodiments, the weight percentage of proteins crosslinked to each other is greater than 75% w/w (e.g., greater than 80%, 85% or 90% w/w) of the nanogel.

A plurality of nanogels is considered to be "monodispersed" in a composition (e.g., an aqueous or otherwise liquid composition) if the nanogels have similar size (e.g., diameter) relative to each other, for example the polydispersity index measured by dynamic light scattering is less than 0.35, more preferably less than 0.3, such as less than 0.25 or less than 0.2. Nanogels of a plurality may be considered to have the same size relative to each other if the sizes among the nanogels in the plurality vary by no more than 5%-10%.

Other aspects of the present disclosure provide nanogels comprising a polymer and at least 75% (e.g., about 80%)

w/w of proteins that are reversibly and covalently crosslinked to each other through a degradable linker. In some embodiments, the degradable linker is a redox responsive linker, such as, for example, a disulfide linker (e.g., Formula I).

Yet other aspects of the present disclosure provide methods of producing a plurality of biologically-active protein nanogels, the methods comprising (a) contacting a protein with a degradable linker (e.g., a disulfide linker) under conditions that permit reversible covalent crosslinking of proteins to each other through the degradable linker, thereby producing a plurality of protein nanogels, and (b) contacting the protein nanogels with a polymer (e.g., polyethylene glycol) under conditions that permit crosslinking of the polymer to proteins of the protein nanogels, thereby producing a plurality of biologically-active protein-polymer nanogels.

In some embodiments, the conditions of (a) include contacting the protein with the degradable linker in an aqueous buffer at a temperature of 4° C. to 25° C. In some embodiments, the conditions of (a) include contacting the protein with the degradable linker in an aqueous buffer for 30 minutes to one hour. In some embodiments, the conditions of (b) include contacting the protein nanogels with the polymer in an aqueous buffer at a temperature of 4° C. to 25° C. In some embodiments, the conditions of (b) include contacting the protein nanogels with the polymer in an aqueous buffer for 30 minutes to one hour. In some embodiments, the aqueous buffer comprises phosphate buffered saline (PBS).

In some embodiments, the conditions of (a) do not include contacting the protein with the degradable linker at a temperature of greater than 30° C. In some embodiments, the conditions of (b) do not include contacting the protein nanogels with the polymer at a temperature of greater than 30° C.

In some embodiments, the conditions of (a) do not include contacting the protein with the degradable linker in an organic solvent (e.g., alcohol). In some embodiments, the conditions of (b) do not include contacting the protein nanogels with the polymer in an organic solvent.

In some embodiments, the protein is a cytokine, growth factor, antibody or antigen. For example, the protein may be a cytokine molecule as described herein. In some embodiments, the cytokine molecule is an IL-2 molecule, e.g., IL-2 or IL-2-Fc. In some embodiments, the cytokine molecule is an IL-15 molecule, e.g., IL-15 or IL-15SA.

In some embodiments, the degradable linker is a redox responsive linker. In some embodiments, the redox responsive linker comprises a disulfide bond. In some embodiments, the degradable linker comprises, or consists of, Formula I.

In some embodiments, the polymer is a hydrophilic polymer. The hydrophilic polymer, in some embodiments, comprises polyethylene glycol (PEG). For example, the hydrophilic polymer may be a 4-arm PEG-NH$_2$ polymer.

In some embodiments, the concentration of the protein in the aqueous buffer is 10 mg/mL to 50 mg/mL (e.g., 10, 15, 20, 25, 30, 35, 40, 45 or 50 mg/mL).

In some embodiments, the plurality of biologically-active protein-polymer nanogels is a monodispersed plurality of biologically-active protein-polymer nanogels.

In some embodiments, the biologically-active protein-polymer nanogels do not include albumin.

In some embodiments, the weight percentage of protein (e.g., biologically-active protein, crosslinked protein) in the biologically-active protein-polymer nanogels is at least 75%. In some embodiments, the weight percentage of protein in the biologically-active protein-polymer nanogels is at least 80%. In some embodiments, the weight percentage of protein in the biologically-active protein-polymer nanogels is at least 85%. In some embodiments, the weight percentage of protein in the biologically-active protein-polymer nanogels is at least 90%.

In some embodiments, the protein, under physiological conditions, is released in its native conformation from the nanogel and is biologically active. In some embodiments, the specific activity of the released protein is at least than 50% (e.g., at least 55%, 60%, 65%, 70%, 75%, 80%, 85%, 90%, 95%, 96%, 97%, 98%, 99% or 100%) of the specific activity of the protein before it was crosslinked to another protein through a degradable linker.

Some aspects of the disclosure provide proteins reversibly linked through a degradable linker to a polymerizable functional group. Such proteins are considered herein to be reversibly modified proteins.

In some embodiments, the polymerizable functional group comprises silane and/or a crosslinkable polymer. In some embodiments, the crosslinkable polymer comprises poly(ethylene oxide), polylactic acid and/or poly(lactic-co-glycolic acid). In some embodiments, the proteins are reversibly linked through a degradable linker to silane.

Other aspects of the disclosure provide pluralities of any reversibly modified protein described herein.

In some embodiments, reversibly modified proteins in such pluralities are crosslinked.

Yet other embodiments of the disclosure provide nanoparticles that comprise a polymer and at least 50% w/w of a protein that is reversibly linked through a degradable linker to a polymerizable functional group. "w/w" here means weight of protein to weight of nanoparticle (e.g., nanogel). A "polymerizable functional group," as used herein, refers to a group of atoms and bonds that can chemically react to form a polymer chain or network. A "polymer" refers to a chain or network of repeating units or a mixture of different repeating units. As used herein, a polymer is itself a functional group. Examples of polymerizable functional groups for use in accordance with the disclosure include, without limitation, silane, ethylene oxide, lactic acid, lactide, glycolic acid, N-(2-hydroxypropyl)methacrylamide, silica, poly(ethylene oxide), polylactic acid, poly(lactic-co-glycolic acid), polyglutamate, polylysine, cyclodextrin and dextran chitosan. Other polymerizable functional groups are contemplated and may be used in accordance with the disclosure. It should be understood, however, that a "polymer," as used herein, is not a protein (is a non-protein), peptide (is a non-peptide) or amino acid (is a non-amino acid).

The term "polymer" encompasses "co-polymer." That is, a polymer may comprise a mixture of different functional groups (e.g., silane-PEG-silane), including shorter polymers or co-polymers. The functional groups are typically polymerized under protein-compatible, neutral conditions. Thus, in some embodiments, polymerization of the functional groups occurs in an at least partially aqueous solution at about pH 6 to about pH 8. For example, polymerization of the functional groups can occur at pH 6, pH 6.5, pH 7, pH 7.5 or pH 8. In some embodiments, polymerization of the functional groups occurs at about pH 7.

In some embodiments, the polymerization reaction is catalyzed by sodium fluoride, potassium fluoride or any other soluble fluoride.

Exemplary polymers that can be reversibly linked to proteins and/or used to form nanoparticles (e.g., nanocapsules, nanogels, hydrogels) include, without limitation, aliphatic polyesters, poly (lactic acid) (PLA), poly (glycolic acid) (PGA), co-polymers of lactic acid and glycolic acid (PLGA), polycarprolactone (PCL), polyanhydrides, poly (ortho)esters, polyurethanes, poly(butyric acid), poly(valeric acid), and poly(lactide-co-caprolactone), and natural polymers such as alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Other polymers are contemplated and may be used in accordance with the disclosure.

In some embodiments, proteins are reversibly linked to hydrophilic polymers such as, for example, polyethylene glycol (PEG), polyethylene glycol-b-poly lysine (PEG-PLL), and/or polyethylene glycol-b-poly arginine (PEG-PArg).

Some embodiments of the present disclosure involve nanoparticles (e.g., nanogels) comprising on their surface a polycation. A polycation is a molecule or chemical complex having positive charges at several sites. Generally, polycations have an overall positive charge. Examples of polycations for use in accordance with the present disclosure include, without limitation, polylysine (poly-L-lysine and/or poly-D-lysine), poly(argininate glyceryl succinate) (PAGS, an arginine-based polymer), polyethyleneimine, polyhistidine, polyarginine, protamine sulfate, polyethylene glycol-b-polylysine (PEG-PLL), or polyethylene glycol-g-polylysine.

In some embodiments, a polycation is added to the surface of a nanogel. In some embodiments, a polycation (e.g., polyethylene glycol-b-polylysine or PEG-PLL) is added to the surface of a nanogel. In some embodiments the polycation is polyethylene glycol-b-polylysine.

In some embodiments the polycation is added to a nanogel with or without an anti-CD45 antibody.

In embodiments, the nanoparticle comprises polyK30. In embodiments, the nanoparticle comprises polyethylene glycol (PEG), polyethylene glycol-b-poly lysine (PEG-PLL), or polyethylene glycol-b-poly arginine (PEG-PArg). In embodiments, the nanoparticle comprise polyK200.

In embodiments, the nanoparticle comprises at least one polymer, cationic polymer, or cationic block co-polymer on the nanoparticle surface. In some embodiments, the cationic polymer comprises poly-lysine, e.g., polyK30 or polyK200. In some embodiments, the poly-lysine is poly-L-lysine. In embodiments, the poly-lysine has an average length of 20-30, 30-40, 40-50, 50-100, 100-150, 150-200, 200-250, 250-300, 300-400, or 400-500 amino acids.

In embodiments, the nanoparticle comprises polyethylene glycol (PEG). In embodiments, the PEG has a molecular weight of 1-2, 2-3, 3-4, 4-5, 5-6, 6-7, 7-8, 8-9, or 9-10 kD.

In some embodiments, the nanoparticle comprises a cationic block co-polymer comprising PEG (e.g., PEG5k) and poly-lysine, e.g., polyK30 or polyK200. In embodiments the cationic block co-polymer comprises PEG5k-polyK30 or PEG5k-polyK200.

Without wishing to be bound by theory, in some embodiments, a nanoparticle comprising a low molecular weight poly-lysine (e.g., having an average length of 10-150, 20-100, 20-80, 20-60, 20-40, or about 30 amino acids) shows superior properties to a nanoparticle comprising a higher molecular weight poly-lysine (eg., having an average length of about 200 amino acids). The superior properties can be, e.g., low toxicity, low aggregation, or high cell loading, or any combination thereof.

In embodiments, the nanoparticle comprising the low molecular weight poly-lysine shows low toxicity to T cells, e.g., as assayed by quantifying the number of live T cells after freezing and thawing, e.g., using the method of Example 23. In embodiments, low toxicity comprises cells that expand at least 1.2-fold, 1.4-fold, 1.6-fold, 1.8-fold, 2-fold, 2.5-fold, 3-fold, 4-fold, or 5-fold after freezing and thawing.

In embodiments, the nanoparticle comprising the low molecular weight poly-lysine shows low aggregation, e.g., as measured by dynamic light scattering, e.g., as described in Example 1. In embodiments, low aggregation comprises a population of nanoparticles having a size of about 80 nm (e.g., 70-90 nm, 60-100 nm, or 50-150 nm).

In embodiments, the nanoparticle comprising the low molecular weight poly-lysine shows high cell loading, as measured by mean fluorescent intensity (MFU) of nanoparticles being loaded onto activated naïve T cells, e.g., as described in Example 18. In embodiments, high cell loading comprises a MFU at least 2, 5, 10, 20, 50, 100, 200, or 500 times greater than a control nanoparticle that is otherwise similar but has polyK200.

In other embodiments, proteins are reversibly linked to hydrophobic polymers such as, for example, polylactic acid (PLA) and/or poly(lactic-co-glycolic acid) (PLGA). These protein-hydrophobic polymer conjugates can, in some embodiments, self-assemble into nanoparticles.

The protein conjugates of the present disclosure, in some embodiments, may be crosslinked to form a hydrogel network, nanogel particle, or protein nanogel, e.g., as described in WO2015/048498 and WO2017/027843, all of which are herein considered to be "nanoparticles."

In some embodiments, the polymerizable functional group comprises silane and/or a crosslinkable polymer. In some embodiments, the crosslinkable polymer comprises poly(ethylene oxide), polylactic acid and/or poly(lactic-co-glycolic acid).

In embodiments, the nanoparticles comprise at least 75% w/w of a protein that is reversibly linked to a polymerizable functional group. In some embodiments, the nanoparticles comprise at least 80% w/w of a protein that is reversibly linked to a polymerizable functional group. Also contemplated herein are nanoparticles that comprise about 50% w/w to about 90% w/w of a protein that is reversibly linked to a polymerizable functional group. For example, in some embodiments, a nanoparticle may have about 50% w/w, about 55% w/w, about 60% w/w, about 65% w/w, about 70% w/w, about 75% w/w, about 80% w/w, about 85% w/w, or about 90% w/w of a protein that is reversibly linked to a polymerizable functional group.

Still other aspects of the disclosure provide methods of producing a nanoparticle, the methods comprising modifying a protein with a degradable linker and polymerizable functional groups, and polymerizing the polymerizable functional groups with a crosslinker and soluble fluoride.

In some embodiments, the polymerizable functional group comprises silane and/or a crosslinkable polymer. In some embodiments, the crosslinkable polymer comprises poly(ethylene oxide), polylactic acid and/or poly(lactic-co-glycolic acid).

In some embodiments, the soluble fluoride is sodium fluoride. In some embodiments, the soluble fluoride is potassium fluoride.

In some embodiments, the nanoparticles comprise one or more reactive group on their surface. In embodiments, the one or more reactive groups on their exterior surface can react with reactive groups on nucleated cells (e.g., T cells). Exemplary nanoparticle reactive groups include, without limitation, thiol-reactive maleimide head groups, haloacetyl (e.g., iodoacetyl) groups, imidoester groups, N-hydroxysuccinimide esters, pyridyl disulfide groups, and the like. These reactive groups react with groups on the nucleated cell surface and, thus, the nanoparticles are bound to the cell surface. In embodiments, when surface modified in this manner, the nanoparticles are intended for use with specific carrier cells having "complementary" reactive groups (i.e., reactive groups that react with those of the nanoparticles). In some embodiments, the nanoparticles will not integrate into the lipid bilayer that comprises the cell surface. Typically, the nanoparticles will not be significantly phagocytosed (or substantially internalized) by the nucleated cells.

In some embodiments, the reactive group is a maleimide, rhodamine or IR783 reactive group.

Targeted Particles

In some embodiments, the particles, e.g., nanoparticles, include a targeting moiety, e.g., an affinity ligand. In some embodiments, the targeting moiety is on the surface of the particle. In some embodiments, the targeting moiety comprise a ligand, or an antibody molecule. In some embodiments, the nanoparticles comprise an antibody molecule that is specific to an immune cell, e.g., a T cell surface moiety. Thus, in some embodiments the nanoparticles themselves do not stimulate nucleated cell activation simply by binding to the nucleated cell. In some embodiments, the targeting moiety increases the surface stability of the nucleated cell, e.g., reduces target protein internalization. In other embodiments, however, the nanoparticles do stimulate nucleated cell activation by binding to the nucleated cell (e.g., binding of the nanoparticles results in crosslinking of cell surface moieties and this activates the nucleated cell). Exemplary targeting moieties include, but are not limited to, affinity ligands, e.g. antibodies to CD45, CD11a (integrin alpha-L), CD18 (integrin beta-2), CD11b, CD11c, CD25, CD8, CD4, or CD2. In some embodiments, the targeting moiety (e.g., an antibody molecule) binds a checkpoint inhibitor such as PD-1, PD-L1, LAG-3, TIM-3, or CTLA-4. In embodiments, the checkpoint inhibitor is present on an immune effector cell, e.g., a T cell or NK cell.

The nanoparticles may comprise an anti-CD45 antibody. In some embodiments, the anti-CD45 antibody is a human anti-CD45 antibody or a humanized anti-CD45 antibody. In some embodiments, the anti-CD45 antibody is an anti-CD45 monoclonal antibody.

In some embodiments, the monoclonal anti-CD45 antibody is BC8 (ACCT: HB-10507), 4B2, 9.4 (ATTC: HB-10508) or GAP8.3 (ATTC: HB-12). Thus, in some embodiments, a nanoparticle (e.g., nanogel) is linked to an anti-CD45 antibody. In some embodiments, a protein nanogel comprising a cytokine (e.g., IL-2, IL-15, IL-15-SA, or a combination thereof) is linked to an anti-CD45 antibody. In some embodiments, the antibody binds to a cell surface receptor and at least 50% (e.g., at least 60%, at least 70%, at least 80%, at least 90%, or at least 95%) of the antibody (e.g., anti-CD45 antibody) remains on the surface of the cell for at least 24 hours (e.g., at least 36 hours, or at least 48 hours). In some embodiments, the antibody (e.g., anti-CD45 antibody) binds to human CD45 with an affinity of 1 uM, 100 nM, 10 nM, 1 nM, 100 pM, 10 pM, 1 pM, 100 fM, 10 fM, or 1 fM or stronger, e.g., as measured by surface plasmon resonance.

In some embodiments, the targeting moiety binds PD-1. For instance, Pidilizumab and other anti-PD-1 antibodies are disclosed in Rosenblatt, J. et al. (2011) J Immunotherapy 34(5): 409-18, U.S. Pat. Nos. 7,695,715, 7,332,582, and 8,686,119, incorporated by reference in their entireties. MEDI0680 and other anti-PD-1 antibodies are disclosed in U.S. Pat. No. 9,205,148 and WO 2012/145493, incorporated by reference in their entireties. Further anti-PD-1 antibodies include those described, e.g., in WO 2010/027827 WO 2011/066342, WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entireties.

In some embodiments, the targeting moiety binds PD-L1. For instance, Atezolizumab and other anti-PD-L1 antibodies are disclosed in U.S. Pat. No. 8,217,149, incorporated by reference in its entirety. Avelumab and other anti-PD-L1 antibodies are disclosed in WO 2013/079174, incorporated by reference in its entirety. Durvalumab and other anti-PD-L1 antibodies are disclosed in U.S. Pat. No. 8,779,108, incorporated by reference in its entirety. BMS-936559 and other anti-PD-L1 antibodies are disclosed in U.S. Pat. No. 7,943,743 and WO 2015/081158, incorporated by reference in their entireties. Further anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entireties.

In some embodiments, the targeting moiety binds LAG-3. The LAG-3 antibody may be chosen from, e.g., LAG525 (Novartis), BMS-986016 (Bristol-Myers Squibb), TSR-033 (Tesaro), MK-4280 (Merck & Co), or REGN3767 (Regeneron). IMP731 and other anti-LAG-3 antibodies are disclosed in WO 2008/132601 and U.S. Pat. No. 9,244,059, incorporated by reference in their entireties. Further anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entireties.

In some embodiments, the targeting moiety binds TIM-3. In some embodiments, the TIM-3 targeting moiety is chosen from MGB453 (Novartis), TSR-022 (Tesaro), or LY3321367 (Eli Lilly). APE5137, APE5121, and other anti-TIM-3 antibodies are disclosed in WO 2016/161270, incorporated by reference in its entireties. Further anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entireties.

In some embodiments, the targeting moiety binds CTLA-4. The antibody Ipilimumab and other anti-CTLA-4 antibodies are disclosed in U.S. Pat. No. 6,984,720, herein incorporated by reference. The antibody Tremelimumab and other anti-CTLA-4 antibodies are disclosed in U.S. Pat. No. 7,411,057, herein incorporated by reference.

The nanoparticles may be covalently conjugated (or attached or bound, as the terms are used interchangeably herein), or they may be non-covalently conjugated to the nucleated cells. Covalent conjugation typically provides a more stable (and thus longer) association between the nanoparticles and the nucleated cells. Covalent conjugation, in some embodiments, also can provide stability and thus more sustained localized delivery of agents in vivo. Non-covalent conjugation includes, without limitation, absorption onto the cell surface and/or lipid bilayer of the cell membrane.

In some instances, covalent attachment can be achieved in a two-step process in which nucleated cells are first incubated with maleimide-bearing nanoparticles to allow conjugation to the cell surface, followed by in situ PEGylation with thiol-terminated poly(ethylene glycol) (PEG) to cap remaining maleimide groups of the particles and avoid particle-mediated crosslinking of cells.

In some embodiments, the protein, under physiological conditions, is released in its native conformation from the nanoparticle and is biologically active.

Nucleated Cells

The nucleated cells are the cells to which the nanoparticles are coupled, e.g., covalently or non-covalently coupled, e.g., thus forming a nucleated cell-nanoparticle complex. In embodiments, the nanoparticles include a protein, e.g., a cytokine molecule as described herein. In some embodiments, the nucleated cell (e.g., a population of nucleated cells) is covalently coupled to a nanoparticle or a plurality of nanoparticles, as disclosed herein. In an embodiment, the nucleated cell (e.g., a population of nucleated cells) is non-covalently coupled to a nanoparticle disclosed herein, e.g., via electrostatic interactions.

In some embodiments, the nucleated cells are modified by contacting the nucleated cells with the nanoparticles disclosed herein after isolation or purification from the subject, e.g., prior to storage, including frozen storage of the cells or transportation of the cells. In some embodiments, the contacting step occurs prior to freezing the cells. In other embodiments, the contacting step occurs after thawing the cells, e.g., prior to administration of the cells.

In one embodiment, the nucleated cells include nucleated cells, including lymphocytes. In some embodiments described herein, the nucleated cells are immune cells, e.g., immune effector cells (e.g., T cells). The T cells may be CD4+ or CD8+ T cells. The T cells may be CD3 T cells. Other suitable cells include B cells, NK cells, NK T cells, and hematopoietic progenitor cells including, without limitation, murine lineage-negative, Sca-1-positive and c-kit-positive cells and their human counterparts. Substantial levels of free thiol (—SH) groups exist on the surfaces of T cells, B cells and hematopoietic progenitor cells, thereby facilitating conjugation of nanocapsules nanoparticles to such cells. In some embodiments, the nanoparticle is linked to a nucleated cell. In some embodiments, the nucleated cell is an immune cell, e.g., a T cell, a B cell, an NK cell or an NKT cell.

Some embodiments of the present disclosure refer to isolated or purified, e.g., substantially purified, nucleated cells. In some embodiments, isolated nucleated cells are cells that have been separated from the environment in which they naturally occur (i.e., they are not present in vivo). T cells in vitro are an example of an isolated cell. It should be understood that nucleated cells may be isolated from their in vivo environment, conjugated to nanoparticles of the present disclosure, and then re-introduced in vivo. Nucleated cells may be isolated from their in vivo environment, associated or conjugated with nanoparticles of the present disclosure, and the nucleated cell-nanoparticle complex mixed with components to permit freezing of the complex and upon thawing may be re-introduced to a patient, e.g. in vivo. Such nucleated cells are still considered to be isolated cells.

In some embodiments, the nucleated cells are acquired, e.g., directly or indirectly, from a subject, e.g., a patient in need to an immune therapy. In embodiments where the nucleated cell is an immune cell, the immune cell, e.g., the T cell, can be obtained from blood, e.g., a blood sample, collected from a subject using any number of techniques known to the skilled artisan. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and, optionally, to place the cells in an appropriate buffer or media for subsequent processing steps.

The nucleated cells, in some embodiments, are genetically engineered to express one or more factors including, without limitation, co-stimulatory molecules or receptors including chimeric receptors. In other embodiments, the nucleated cells are not genetically engineered. In some embodiments, the nucleated cells are isolated and naturally occurring (e.g., they have not been genetically or otherwise engineered).

Depending on their nature and function, the nucleated cells, including genetically engineered nucleated cells, in some embodiments, are manipulated prior to conjugation with the nanoparticles. The nucleated cells, however, need not be surface-modified in order to facilitate conjugation of the nanoparticles. In some of embodiments, instead, reactive groups that normally exist on the nucleated cell surface are used without having to incorporate reactive groups or other entities onto the cell surface. As a result, such nucleated cells do not require the presence of exogenous entities such as antibodies or antibody fragments, among others, on their surface in order to conjugate to nanoparticles.

Such manipulation may also involve activation of the nucleated cells, as is routinely performed for T cells. The nucleated cells may, in some embodiments, be expanded and/or activated (or stimulated, as the terms are used interchangeably herein) in vitro prior to mixing with nanoparticles. Expansion and activation protocols will vary depending on the nucleated cell type but can include incubation with one or more cytokines, incubation with one or more cell types, and incubation with one or more antigens. If the nucleated cell is a T cell, then activation may be performed by stimulation with antibodies to various T cell surface molecules including antibodies to cell surface receptors, e.g. anti-CD3 antibodies, anti-CD28, followed by incubating the T cells with IL-2, IL-15, IL-15 superagonist, and optionally costimulatory molecules such as B7, B7.2, CD40 and the like. In some embodiments, the nucleated cells and more particularly the T cells, are not coated with exogenous antibodies on their cell surface (i.e., the cells have not been contacted with antibodies or antibody fragments in vitro prior to administration).

Expansion may be measured by proliferation assays involving incorporation of radiolabeled nucleotides such as tritiated thymidine. Activation may be measured by production of cytokines such as IL-2, gamma-IFN, IL-1, IL-4, IL-6 and TNF, among others. Other ways of measuring expansion and activation are known in the art and include use of fluorescent labeled antibodies against cell surface receptors which can be monitored by flow cytometry, e.g. antibodies against CD25, CD71, CD28, CD30, CD154, CD69, CD134, and may be used in accordance with the disclosure.

Nucleated cells may be selected in order to enrich higher numbers of such cells in smaller volumes and/or to remove other, potentially unwanted, cells from the composition. Selection may involve positive or negative selection including, for example, column or plate based enrichment protocols.

Immune cells, e.g., T cells, B cells and NK cells, may be harvested from the peripheral blood of a subject.

Hematopoietic progenitor cells may be obtained from a number of sources including but not limited to cord blood, bone marrow, mobilized peripheral blood and, in some instances, differentiated embryonic stem cells.

Hematopoietic progenitor cells have been characterized in the art. Such cells in the human generally have minimally a CD34+ phenotype, although they may also be $CD59^+$, $Thy1/CD90^+$, $CD38^{lo/nrh}$, $CD33^-$, and/or $c$-$kit/CD117^+$. They also are characterized as not expressing lineage specific markers. They can be harvested from bone marrow, cord blood or peripheral blood using affinity columns, magnetic beads, fluorescence activated cell sorting (FACS), some combination thereof, and the like. These cells have the ability to repopulate one or more hematopoietic lineages upon transplantation. Preferably, these cells repopulate more than one lineage, and even more preferably, all lineages. Repopulation or population of lineages as used herein refers to the differentiation of the stem cell into one or more lineages such that progeny of the stem cell contribute to the make-up of that lineage in the subject. It does not, however, require that the entire lineage compartment derive from the transplanted cells, however in some instances this may occur.

Isolated stem cells may be obtained by fractionating a heterogeneous cell population according to one or more markers, including by not limited to cell surface markers.

The nucleated cells may be eukaryotic cells, such as mammalian cells (e.g., human cells). Alternatively, they may be non-mammalian cells. In still other embodiments, the nucleated cells may be prokaryotic cells (e.g., bacterial cells). Several bacterial cell types are of particular interest. For example, attenuated *Salmonella typhimurium* is under study as a candidate vector for oral vaccine delivery (Xiang et al., *Immunol Rev* 222:117, 2008; and Iweala et al., *J Immunol* 183(4):2252, 2009) and engineered *E. coli* bacteria have been shown to be capable of specific homing to poorly oxygenated tumors (Cheong et al., *Science* 314(5803):1308, 2006). Bacteria offer new modes of administration and tissue site targeting possibilities, such as oral administration and the ability to target therapeutics to the gut and gut-associated lymphoid tissues. Such microbial vectors may offer advantages relative to autologous host cells in terms of creating off-the-shelf ready-to-use cell-nanoparticles systems. Particles conjugation to microbes can be achieved using the same suite of chemical strategies described for mammalian cells. In some instances, temporary removal of flagellar coats of microbes (e.g., via simple mechanical shearing as described by Rosu et al., *J Bacteriol* 188(14):5196, 2006) can be used to achieve optimal conjugation of particles to microbe cell bodies.

Methods of Making a Nanoparticle

Provided herein are methods of producing nanoparticles. An example of a nanoparticle is a protein nanogel, such as a protein nanogel that contains intact, biologically-active proteins but does not contain a carrier (e.g., albumin, BSA).

In some embodiments, a method of producing a biologically-active protein nanogel comprises contacting a protein with a degradable linker under conditions that permit reversible covalent crosslinking of proteins to each other through the degradable linker, thereby producing a biologically-active protein nanogel. In some embodiments, a method further comprises contacting the protein nanogel with a polymer under conditions that permit crosslinking of the polymer to proteins of the protein nanogel, thereby producing a biologically-active protein-polymer nanogel. In some embodiments, a plurality of protein nanogels or a plurality of protein-polymer nanogels is produced.

Typically, conditions that permit reversible covalent crosslinking of proteins to each other through a degradable linker include contacting the proteins with degradable linkers at a temperature of 4° C. to 25° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C.). In some embodiments, proteins are incubated with the degradable linkers in an aqueous buffer (e.g., PBS) at a temperature of 4° C. to 25° C. (e.g., room temperature). In some embodiments, proteins are incubated with the degradable linkers in an aqueous buffer (e.g., PBS) at a temperature of no greater than 20° C., 30° C., or 40° C., or at a temperature of about 35-45° C. In some embodiments, conditions that permit reversible covalent crosslinking of proteins to each other through a degradable linker include contacting proteins with degradable linkers for 30 minutes to two hours, or 30 minutes to one hour (e.g., 30, 35, 40, 45, 50, 55 or 60 minutes). In some embodiments, proteins are incubated with the degradable linkers in an aqueous buffer (e.g., PBS) for 30 minutes to two hours, or 30 minutes one hour.

In some embodiments, the concentration of the protein in the aqueous buffer is 10 mg/mL to 50 mg/mL. For example, the concentration of the protein in an aqueous buffer may be 10 mg/mL, 15 mg/mL, 20 mg/mL, 25 mg/mL, 30 mg/mL, 35 mg/mL, 40 mg/mL, 45 mg/mL or 50 mg/mL protein/aqueous buffer).

In some embodiments, the weight percentage of protein in a biologically-active protein nanogel or protein-polymer nanogel is at least 75% w/w. For example, the weight percentage of protein in the biologically-active protein-polymer nanogels is at least 80% w/w, at least 85% w/w, at least 90% w/w, or at least 95% w/w. In some embodiments, the weight percentage of protein in a biologically-active protein nanogel or protein-polymer nanogel is 75% w/w to 90% w/w, 80% w/w to 90% w/w, or 85% w/w to 90% w/w.

Conditions that permit crosslinking of a polymer to proteins of a protein nanogel include contacting the protein nanogel with a polymer at a temperature of 4° C. to 25° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C.). In some embodiments, protein nanogels are incubated with the polymers in an aqueous buffer (e.g., PBS) at a temperature of 4° C. to 25° C. (e.g., room temperature). In some embodiments, protein nanogels are incubated with the polymers in an aqueous buffer (e.g., PBS) at a temperature of no greater than 30° C. In some embodiments, conditions that permit crosslinking of a polymer to proteins of a protein nanogel include contacting the protein nanogel with a polymer for 30 minutes to two hours, or 30 minutes to one hour (e.g., 30, 35, 40, 45, 50, 55 or 60 minutes). In some embodiments, protein nanogels are incubated with the polymer in an aqueous buffer (e.g., PBS) for 30 minutes to two hours, or 30 minutes one hour.

Other methods of producing nanoparticles of the present disclosure may comprise modifying a protein with a degradable linker and polymerizable functional groups, and polymerizing the polymerizable functional groups with a crosslinker and soluble fluoride.

Proteins of the disclosure may be modified with, or conjugated to, a degradable linker such as, for example, a redox responsive linker. The modification may, in some embodiments, be a covalent modification. FIG. 3A of WO 2015/048498 illustrates one example of a protein modification scheme. In this example, a protein is covalently conjugated, through a degradable linker, to silane.

Polymerizable functional groups may be polymerized with a crosslinker in the presence of a soluble fluoride catalyst. In some embodiments, the crosslinker is a polymer (e.g., silane-PEG-silane). In some embodiments, the soluble fluoride is sodium fluoride. In some embodiments, the soluble fluoride is potassium fluoride.

Compositions

Compositions, including pharmaceutical compositions, comprising protein nanoparticles (e.g., nucleated cell-nanoparticle complex) are provided herein. A composition can be formulated in pharmaceutically-acceptable amounts and in pharmaceutically-acceptable compositions. The term "pharmaceutically acceptable" means a non-toxic material that does not interfere with the effectiveness of the biological activity of the active ingredients (e.g., biologically-active proteins of the nanoparticles). Such compositions may, in some embodiments, contain salts, buffering agents, preservatives, and optionally other therapeutic agents.

Pharmaceutical compositions also may contain, in some embodiments, suitable preservatives.

Pharmaceutical compositions may, in some embodiments, be presented in unit dosage form and may be prepared by any of the methods well-known in the art of pharmacy.

Pharmaceutical compositions suitable for parenteral administration, in some embodiments, comprise a sterile aqueous or non-aqueous preparation of the nanoparticles, which is, in some embodiments, isotonic with the blood of the recipient subject. This preparation may be formulated according to known methods. A sterile injectable preparation also may be a sterile injectable solution or suspension in a non-toxic parenterally-acceptable diluent or solvent.

Pharmaceutical compositions of the present disclosure, in some embodiments, may be sterile and contain an effective amount of a nanoparticle (e.g., nanogel) with or without a nucleated cell, alone or in combination with another agent, for producing the desired response in a unit of weight or volume.

Uses

Further aspects of the disclosure provide methods of optimized production of nucleated cells. In an embodiment, a function of the nucleated cell, e.g., an immune cell, is promoted, e.g., conserved, after one or more cycles of freezing and/or thawing. The produced nucleated cells (e.g., including the nanoparticles disclosed herein, e.g., the nucleated cell-nanoparticle complex) can be thawed and administered, e.g., directly administered, to a subject. Accordingly, in another aspect, disclosed herein is a method of administering to a subject, e.g., a human subject, a population of nucleated cells as described herein.

In some embodiments, the subject are human subjects. Subjects also include animals such as household pets (e.g., dogs, cats, rabbits, ferrets), livestock or farm animals (e.g., cows, pigs, sheep, chickens and other poultry), horses such as thoroughbred horses, laboratory animals (e.g., mice, rats, rabbits), and the like. In some embodiments, the subject has, or is at risk of having, a disease. In some embodiments, the subject is a patient, e.g., a human patient. In other embodiments, the disease is cancer, diabetes, an autoimmune disease, allergies or allergic conditions, asthma or a cardiovascular disease. In embodiment, the subject is in need of a transplant.

The subjects to whom the compositions herein (e.g., nucleated cell compositions) are delivered may be normal, or healthy, subjects. Alternatively they may have or may be at risk of developing a condition that can be diagnosed or that can benefit from delivery of one or more cells.

Such conditions include cancer (e.g., solid tumor cancers), autoimmune disorders, transplant rejection, and the like.

In embodiments, the cancer is a hematological cancer. In embodiments, the hematological cancer is a leukemia or a lymphoma. Exemplary hematological cancers include but are not limited to a Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia, chronic myeloid leukemia, myelodysplastic syndrome, multiple myeloma, or acute lymphocytic leukemia. In embodiments, the cancer is other than acute myeloid leukemia (AML).

In embodiments, the cancer is a solid cancer. Exemplary solid cancers include but are not limited to ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In some embodiments, the subject to be treated is the same as the subject from which the nucleated cells, e.g., the immune cells, were isolated from. In other embodiments, the subject to be treated is different from the subject from which the nucleated cells, e.g., the immune cells, were isolated from. In embodiments, both subjects have or have had the same type of cancer.

In embodiments, the nucleated cells are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or the nucleated cells) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

Further aspects and embodiments of the present application are provided herein in the following enumerated paragraphs.

1. A composition comprising a nucleated cell, a buffered aqueous media solution, and a nanoparticle that comprises at least one agent that promotes, e.g. conserves or enhances, viability, proliferation, cytotoxic activity or activation of the nucleated cell, wherein the composition is frozen and upon thawing of the composition, the agent is optionally released from the nanoparticle and improves viability, proliferation, cytotoxic activity or activation of the nucleated cell compared to a nucleated cell in a buffered aqueous media solution frozen and thawed absent the nanoparticle.

2. A composition comprising a nucleated cell, a buffered aqueous media solution, and a nanoparticle that comprises at least one conservation agent that promotes, e.g., conserves or enhances, viability, proliferation, cytotoxic activity or activation of the nucleated cell, wherein upon thawing of a frozen preparation of the composition, the conservation agent is optionally released from the nanoparticle and promotes, e.g., conserves or enhances, viability, proliferation, cytotoxic activity or activation of the nucleated cell as compared to a nucleated cell in a buffered aqueous media solution frozen and thawed absent the nanoparticle, wherein the conservation agent comprises an IL-15 molecule complexed, e.g., covalently or noncovalently, with a polypeptide comprising:
   a first domain comprising the amino acid sequence of SEQ ID NO: 3 or SEQ ID NO: 4, or an amino acid sequence having at least 80%, 85%, 90%, 95%, 96%, 97%, 98%, or 99% identity thereto, and having IL-15 binding activity or a first domain comprising the amino acid sequence of SEQ ID NO: 7 or SEQ ID NO: 8, or an amino acid sequence having at least 80%, 85%, 90%, 95%, 96%, 97%, 98%, or 99% identity thereto, and having IL-15 binding activity; and
   optionally, a second, heterologous domain, e.g., an antibody molecule, e.g., a Fab fragment, a Fab2 fragment, or scFv; a heavy chain antibody fragment; an Fc fragment; or an affibody fragment or derivative, e.g., a sdAb (nanobody) fragment,
   wherein optionally at least part the composition is frozen.

3. The composition of embodiment 1, wherein the composition, e.g., the nanoparticle and/or the conservation agent, comprises an IL-15 complex, said IL-15 complex comprising an IL-15 molecule complexed, e.g., covalently or noncovalently, with a polypeptide comprising an IL-15 receptor or an IL-15-binding fragment thereof.

4. The composition of embodiment 2 or 3, wherein the IL-15 molecule comprises an IL-15 mutant, e.g., a human IL-15 polypeptide having one or more amino acid substitutions, e.g., a substitution at position 72, e.g., an N to D substitution.

5. The composition of any of embodiments 2-4, wherein the IL-15 molecule is an IL-15$^{N72D}$ polypeptide of SEQ ID NO: 6 or an amino acid sequence having at least 80%, 85%, 90%, 95%, 96%, 97%, 98%, or 99% identity thereto, which has IL-15Ra binding activity.

6. The composition of any of embodiments 2-5, wherein the polypeptide comprising the IL-15 receptor or fragment thereof comprises a sushi-Fc polypeptide of SEQ ID NO: 5 or an amino acid sequence having at least 80%, 85%, 90%, 95%, 96%, 97%, 98%, or 99% identity thereto, which has IL-15 binding activity.

7. The composition of any of embodiments 2-5, wherein the polypeptide comprising the IL-15 receptor or fragment thereof comprises a sushi domain (e.g., of SEQ ID NO: 7 or SEQ ID NO: 8) and a second, heterologous domain comprising an effector-attenuated Fc domain, e.g., a human IgG2 Fc domain, e.g., a human IgG2 domain of SEQ ID NO: 11 or an amino acid sequence having at least 80%, 85%, 90%, 95%, 96%, 97%, 98%, or 99% identity thereto.

8. A composition of any of embodiments 1-7, wherein the conservation agent is a stimulatory molecule for sustaining nucleated cell viability, proliferation, cytotoxic activity or activation.

9. The composition of any of embodiments 1-8, wherein interferon gamma production is promoted.

10. The composition of any of embodiments 1-9, wherein activation is measured by interferon gamma production.

11. The composition according to any of embodiments 1-10, wherein the composition comprises (e.g., the media contains) a compound that stimulates and sustains cell viability and proliferation.

12. The composition of any of embodiments 1-11, wherein the composition comprises (e.g., the media contains) a compound that protects the cells during freezing and thawing.

13. The composition of any of embodiments 1-12, wherein the release of the conservation agent from the nanoparticle occurs over 1 hour to 3 weeks, such as 1 hour to 24 hours, 1 day to 3 days, 4 days to 6 days, 1 week to 2 weeks, or 2 weeks to 3 weeks.

14. The composition of any of embodiments 1-13 wherein the nanoparticle is associated with the surface of the nucleated cell.

15. The composition of any of embodiments 1-14, wherein the nucleated cell is an immune effector cell (e.g., a lymphocyte, T cell, B cell, or Natural Killer cell), or a hematopoietic stem cell.

16. The composition of any of embodiments 1-15, wherein the nanoparticle is associated with the cell surface by electrostatic attraction to the nucleated cell.

17. The composition of any of embodiments 1-16, wherein the nanoparticle comprises at least one ligand, wherein the ligand has affinity for proteins, carbohydrates or lipids on the surface of the nucleated cell.

18. The composition of any of embodiments 1-17, wherein the nanoparticle is covalently conjugated, e.g., to the surface, of the nucleated cell.

19. The composition of any of embodiments 1-17, wherein the nanoparticle is not covalently conjugated to the nucleated cell.

20. The composition of any of embodiments 1-19, wherein the nanoparticle comprises a liposome, a protein nanogel, a nucleotide nanogel, a polymer nanoparticle, or a solid nanoparticle.

21. The composition of any of embodiments 1-20, wherein the nanoparticle comprises a liposome.

22. The composition of any of embodiments 1-21, wherein the nanoparticle comprises a protein nanogel.

23. The composition of any of embodiments 1-22, wherein the nanoparticle comprises at least one polymer, cationic polymer, or cationic block co-polymer on the nanoparticle surface.

24. The composition of any of embodiments 1-23, wherein the nanoparticle comprises a cationic block co-polymer comprising PEG (e.g., a PEG having a molecular weight of about 1-10, 2-8, 4-6, or about 5 kD) and a poly-lysine, (e.g., a poly-lysine having an average length of 10-50, 20-40, or about 30 amino acids).

25. The composition of any of embodiments 1-24, comprising a compound that stabilizes the nanoparticle in solution or on the cell surface and/or increases the interaction between the nanoparticle and the surface of the nucleated cell, e.g., protamine, chitosan, a carbohydrate, a heparansulfate proteoglycan, a natural polymer, a polysaccharide, a dextramer, cellulose, fibronectin, collagen, fibrin, or a proteoglycan.

26. The composition of any of embodiments 1-25, comprising a cytokine molecule, growth factor molecule, or a costimulatory molecule.

27. The composition of any of embodiments 1-26, comprising a second conservation agent which comprises a cytokine, e.g., IL2, IL6, IL7, IL12, IL15, IL17, IL18, IL21, IL-23, IL-4, IL1alpha, IL1beta, IL-5, IFNgamma, TNFa, IFNalpha, IFNbeta, GM-CSF, or GCSF, or a variant thereof, e.g., a superagonist thereof.

28. The composition of any of embodiments 1-27, comprising an antibody molecule or agonist ligand against a costimulatory molecule, e.g., wherein the costimulatory molecule is chosen from OX40, CD28, GITR, VISTA, CD40, CD3, or an agonist of CD137.

29. The composition of any of embodiments 1-28, wherein the nanoparticle comprises an entity that reduces, e.g. inhibits, diminishes or decreases internalization, by the nucleated cell, of the nanoparticle.

30. The composition of any of embodiments 1-29, wherein the nanoparticle comprises an antibody molecule to CD45, CD11a (integrin alpha-L), CD18 (integrin beta-2), CD11b, CD11c, CD25, CD8, or CD4.

31. The composition of any of embodiments 1-30, which comprises an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;
a sushi-Fc polypeptide of SEQ ID NO: 5 or an amino acid sequence having at least 80%, 85%, 90%, 95%, 96%, 97%, 98%, or 99% identity thereto, which has IL-15 binding activity;
a cationic block co-polymer comprising PEG having a molecular weight of about 1-10, 2-8, 4-6, or about 5 kD and a poly-lysine having an average length of 10-50, 20-40, or about 30 amino acids; and
optionally, an antibody molecule to CD45.

32. The composition of any of embodiments 1-30, which comprises
an IL-15 polypeptide of SEQ ID NO: 1 or an amino acid sequence having at least 80%, 85%, 90%, 95%, 96%, 97%, 98%, or 99% identity thereto which has IL-15Ra binding activity;
a sushi-Fc polypeptide comprising a sushi domain of SEQ ID NO: 7 or SEQ ID NO: 8 or an amino acid sequence having at least 80%, 85%, 90%, 95%, 96%, 97%, 98%, or 99% identity thereto, which has IL-15 binding activity, and an Fc domain of SEQ ID NO: 11 or an amino acid sequence having at least 80%, 85%, 90%, 95%, 96%, 97%, 98%, or 99% identity thereto;
a cationic block co-polymer comprising PEG having a molecular weight of about 1-10, 2-8, 4-6, or about 5 kD and a poly-lysine having an average length of 10-50, 20-40, or about 30 amino acids; and
optionally, an antibody molecule to CD45.

33. The composition of any of embodiments 1-32, wherein the nanogel is a high-density protein structure (e.g., greater than 80% protein by weight), and/or wherein the protein is cross-linked by a cross-linking molecule that upon degradation releases the proteins in a native form.

34. The composition of any of embodiments 1-33, wherein the nanoparticle comprises a nanogel that is cross linked by a reversible linker that is sensitive to redox (disulfide) or pH (hydrolysable groups) or enzymes (proteases).

35. A method for promoting, e.g., conserving or enhancing the viability, proliferation, cytotoxic activity or activation of a nucleated cell isolated from a patient and further subject to freeze-thaw treatment, wherein the nucleated cell is modified by combination with a buffered aqueous solution, and a nanoparticle that comprises at least one agent that conserves or enhances one or more of the viability, proliferation, cytotoxic activity or activation of the nucleated cell, wherein the modified nucleated cell is frozen and upon thawing, the conservation agent is optionally released from the nanoparticle and improves viability, proliferation, cytotoxic activity or activation of the nucleated cell compared to a nucleated cell in a buffered aqueous media solution frozen and thawed absent the nanoparticle.

36. A method for promoting, e.g., conserving or enhancing the viability, proliferation, cytotoxic activity or activation of a nucleated cell, e.g., prior to freezing the nucleated cell, wherein the nucleated cell has been isolated from a patient, comprising modifying the nucleated cell by combining it with a buffered aqueous solution, and a nanoparticle that comprises at least one conservation agent that conserves or enhances the viability, proliferation, cytotoxic activity or activation of the nucleated cell, e.g., compared to the viability, proliferation, cytotoxic activity or activation of a nucleated cell in a buffered aqueous media solution frozen and thawed absent the nanoparticle.

37. A method for promoting, e.g., enhancing, one or more of the viability, proliferation, cytotoxic activity or activation of a nucleated cell wherein the nucleated cell has been isolated from a patient and modified by combination with a buffered aqueous solution, a nanoparticle that comprises at least one conservation agent that conserves or enhances the viability, proliferation, cytotoxic activity or activation of the nucleated cell, said method comprising subjecting the modified nucleated cell to at least one freeze thaw cycle.

38. A method of making a frozen composition of nucleated cells comprising:
providing an unfrozen composition comprising nucleated cells, a buffered aqueous media solution and a plurality of nanoparticles that comprise at least one conservation agent, that, e.g., upon thawing of a frozen preparation of the nucleated cells, promotes, e.g., conserves or enhances, the viability, proliferation, cytotoxic activity or activation of the nucleated cells,
optionally, reducing the temperature of the composition sufficiently for the composition to freeze,
thereby freezing a composition of nucleated cells.

39. The method of embodiment 38, wherein the temperature of the composition is reduced to less than 0 degrees centigrade.

40. The method of embodiment 38 or 39, wherein the temperature of the composition is reduced to less than negative 10 degrees centigrade.

41. The method of any of embodiments 37-40, comprising maintaining the frozen composition of nucleated cells as frozen for at least one hour.

42. The method of any of embodiments 37-41, wherein providing comprises:
combining the nucleated cells with a nanoparticle that comprises a conservation agent, and optionally combining the nucleated cells with a buffered aqueous media solution.

43. The method of any of embodiments 37-42, wherein providing comprises receiving the nanoparticle from another entity and combining the nanoparticles with the nucleated cells.

44. The method of any of embodiments 37-43, wherein providing comprises receiving the unfrozen composition of nucleated cells from another entity.

45. The method of any of embodiments 37-44, comprising providing or releasing the frozen composition of nucleated cells to another entity, e.g., a healthcare provider, e.g., a hospital, clinic, or doctor's office.

46. The method of any of embodiments 37-45, comprising thawing the frozen composition of nucleated cells to provide a thawed composition of nucleated cells.

47. The method of any of embodiment 37-46, wherein upon thawing of a frozen preparation of the composition, the conservation agent is released from the nanoparticle and promotes, e.g., conserves or enhances, viability, proliferation, cytotoxic activity or activation of the nucleated cell as compared to a nucleated cell in a buffered aqueous media solution frozen and thawed absent the nanoparticle.

48. The method of any of embodiments 37-47, wherein the conservation agent comprises: an IL-15 polypeptide receptor alpha fragment; and
optionally, a second, heterologous domain, e.g., an antibody molecule, e.g., a Fab fragment, a Fab2 fragment, or scFv; a heavy chain antibody fragment; an Fc fragment; or an affibody fragment or derivative, e.g., a sdAb (nanobody) fragment.

49. The method of any of embodiments 37-48, wherein the conservation agent is a stimulatory molecule for sustaining nucleated cell viability, proliferation, cytotoxic activity or activation.

50. The method of any of embodiments 37-49, wherein interferon gamma production is promoted.

51. The method of embodiment 50, wherein activation is measured by interferon gamma production.

52. The method of any of embodiments 37-51, wherein the composition comprises (e.g., the media contains) a compound that stimulates and sustains cell viability and proliferation.

53. The method of any of embodiments 37-52, wherein the media comprises a compound that protects the cells during freezing and thawing.

54. The method of any of embodiments 37-53, wherein the release of conservation agent from the nanoparticle occurs over 1 hour to 3 weeks, such as 1 hour to 24 hours, 1 day to 3 days, 4 days to 6 days, 1 week to 2 weeks, or 2 weeks to 3 weeks.

55. The method of any of embodiments 37-54, wherein nanoparticle is associated with the surface of the nucleated cell.

56. The method of any of embodiments 37-55, wherein the nucleated cell comprises an immune effector cell (e.g., a lymphocyte, T cell, B cell, or Natural Killer cell), or a hematopoietic stem cell.

57. The method of any of embodiments 37-56, wherein the nanoparticle is associated with the cell surface by electrostatic attraction to the nucleated cell.

58. The method of any of embodiments 37-57, wherein the nanoparticle comprises a ligand, wherein the ligand has affinity for proteins, carbohydrates or lipids on the surface of the nucleated cell.

59. The method of any of embodiments 37-58, wherein the nanoparticle is covalently conjugated, e.g., to the surface, of the nucleated cell.

60. The method of any of embodiments 37-58, wherein the nanoparticle is not covalently conjugated to the nucleated cell.

61. The method of any of embodiments 37-60, wherein the nanoparticle comprises a liposome, a protein nanogel, a nucleotide nanogel, a polymer nanoparticle, or a solid nanoparticle.

62. The method of embodiment 61, wherein the nanoparticle comprises a liposome.

63. The method of embodiment 61, wherein the nanoparticle comprises a protein nanogel.

64. The method of any of embodiments 37-63, wherein the nanoparticle comprises at least one polymer, cationic polymer, or cationic block co-polymer on the nanoparticle surface.

65. The method of any of embodiments 37-64, wherein the nanoparticle comprises a cationic block co-polymer comprising PEG (e.g., a PEG having a molecular weight of about 1-10, 2-8, 4-6, or about 5 kD) and a poly-lysine, (e.g., a poly-lysine having an average length of 10-50, 20-40, or about 30 amino acids).

66. The method of any of embodiments 37-65, wherein the composition comprises a compound that stabilizes the nanoparticle in solution or on the cell surface and/or increases the interaction between the nanoparticle and the surface of the nucleated cell, e.g., protamine, chitosan, a carbohydrate, a heparan-sulfate proteoglycan, a natural polymer, a polysaccharide, a dextramer, cellulose, fibronectin, collagen, fibrin, or a proteoglycan.

67. The method of any of embodiments 37-66, wherein the conservation agent is a stimulatory molecule for sustaining nucleated cell viability, proliferation, cytotoxic activity or activation.

68. The method of any of embodiments 37-67, wherein the conservation agent comprises an IL-15 molecule complexed, e.g., covalently or noncovalently, with a polypeptide comprising:
a first domain comprising the amino acid sequence of SEQ ID NO: 3 or SEQ ID NO: 4, or an amino acid sequence having at least 80%, 85%, 90%, 95%, 96%, 97%, 98%, or 99% identity thereto, and having IL-15 binding activity or a first domain comprising the amino acid sequence of SEQ ID NO: 7 or SEQ ID NO: 8, or an amino acid sequence having at least 80%, 85%, 90%, 95%, 96%, 97%, 98%, or 99% identity thereto, and having IL-15 binding activity; and
optionally, a second, heterologous domain, e.g., an antibody molecule, e.g., a Fab fragment, a Fab2 fragment, or scFv; a heavy chain antibody fragment; an Fc fragment; or an affibody fragment or derivative, e.g., a sdAb (nanobody) fragment.

69. The method of any of embodiments 37-68, wherein the conservation agent comprises a cytokine molecule, growth factor molecule, or a costimulatory molecule.

70. The method of any of embodiments 37-69, wherein the conservation agent comprises a cytokine molecule, e.g., IL2, IL6, IL7, IL12, IL15, IL17, IL18, IL21, IL-23, IL-4, IL1alpha, IL1beta, IL-5, IFNgamma, TNFa, IFNalpha, IFNbeta, GM-CSF, or GCSF, or a variant, e.g., a superagonist thereof.

71. The method of any of embodiments 37-70, wherein the composition comprises an antibody molecule or agonist ligand against a costimulatory molecule, e.g., wherein the costimulatory molecule is chosen from OX40, CD28, GITR, VISTA, CD40, CD3, or an agonist of CD137.

72. The method of any of embodiments 37-71, wherein the composition, e.g., the nanoparticle, comprises an entity that reduces, e.g. inhibits, diminishes or decreases internalization, by the nucleated cell, of the nanoparticle.

73. The method of any of embodiments 37-72, wherein the composition, e.g., the nanoparticle comprises an antibody molecule to CD45, CD11a (integrin alpha-L), CD18 (integrin beta-2), CD11b, CD11c, CD25, CD8, or CD4.

74. The method of any of embodiments 37-73, wherein the nanogel is a high-density protein structure (e.g., greater than 80% protein by weight), and/or wherein the protein is cross-linked by a cross-linking molecule that upon degradation releases the proteins in a native form.

75. The method of any of embodiments 37-74, wherein the nanoparticle comprises a nanogel that is cross linked by a reversible linker that is sensitive to redox (e.g., disulfide) or pH (e.g., hydrolysable groups) or enzymes (e.g., proteases).

76. The method of any of embodiments 37-75, wherein the nanoparticle comprises an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;

a sushi-Fc polypeptide of SEQ ID NO: 5 or an amino acid sequence having at least 80%, 85%, 90%, 95%, 96%, 97%, 98%, or 99% identity thereto, which has IL-15 binding activity;

a cationic block co-polymer comprising PEG having a molecular weight of about 1-10, 2-8, 4-6, or about 5 kD and a poly-lysine having an average length of 10-50, 20-40, or about 30 amino acids; and optionally, an antibody molecule to CD45.

77. A method of making a thawed composition of nucleated cells, comprising:

providing a frozen composition of nucleated cells comprising nucleated cells and a nanoparticle that comprises at least one conservation agent; and warming the frozen composition of nucleated cells sufficiently to thaw the frozen composition of nucleated cells, thereby making a thawed composition of nucleated cells.

78. The method of embodiment 77, wherein providing comprises receiving the frozen composition from another entity, e.g., an entity which makes and/or freezes the composition of nucleated cells.

79. The method of embodiment 77, wherein providing comprises:

combining the nucleated cells with a buffered aqueous media solution and a nanoparticle that comprises at least one conservation agent.

80. The method of embodiment 77, wherein providing comprises receiving the nanoparticle from another entity and combining the nanoparticles with the nucleated cells.

81. The method of any of embodiments 77-80, comprising prior to warming the frozen composition of nucleated cells, maintaining the frozen composition of nucleated cells as frozen for at least one hour.

82. The method of any of embodiments 77-81, wherein upon thawing of a frozen composition, the conservation agent is released from the nanoparticle and promotes, e.g., conserves or enhances, viability, proliferation, cytotoxic activity or activation of the nucleated cell as compared to a nucleated cell in a buffered aqueous media solution frozen and thawed absent the nanoparticle.

83. The method of any of embodiments 77-82, wherein the conservation agent is a stimulatory molecule for sustaining nucleated cell viability, proliferation, cytotoxic activity or activation.

84. The method of any of embodiments 77-83, wherein interferon gamma production is promoted.

85. The method of embodiment 84, wherein activation is measured by interferon gamma production.

86. The method according to any of embodiments 77-85, wherein the composition comprises (e.g., the media contains) a compound that stimulates and sustains cell viability and proliferation.

87. The method of any of embodiments 77-86, wherein the composition (e.g., the media) comprises a compound that protects the cells during freezing and thawing.

88. The method of any of embodiments 77-87, wherein the release of conservation agent from the nanoparticle occurs over 1 hour to 3 weeks, such as 1 hour to 24 hours, 1 day to 3 days, 4 days to 6 days, 1 week to 2 weeks, or 2 weeks to 3 weeks.

89. The method of any of embodiments 77-88, wherein nanoparticle is associated with the surface of the nucleated cell.

90. The method of any of embodiments 77-89, wherein the nucleated cell is an immune effector cell (e.g., a lymphocyte, T cell, B cell, or Natural Killer cell), or a hematopoietic stem cell.

91. The method of any of embodiments 77-90, wherein the nanoparticle is associated with the cell surface by electrostatic attraction to the nucleated cell.

92. The method of any of embodiments 77-91, wherein the nanoparticle comprises a ligand, wherein the ligand has affinity for proteins, carbohydrates or lipids on the surface of the nucleated cell.

93. The method of any of embodiments 77-92, wherein the nanoparticle is covalently conjugated, e.g., to the surface, of the nucleated cell.

94. The method of any of embodiments 77-92, wherein the nanoparticle is not covalently conjugated to the nucleated cell.

95. The method of any of embodiments 77-94, wherein the nanoparticle comprises a liposome, a protein nanogel, a nucleotide nanogel, a polymer nanoparticle, or a solid nanoparticle.

96. The method of embodiment 95, wherein the nanoparticle comprises a liposome.

97. The method of embodiment 95, wherein the nanoparticle comprises a protein nanogel.

98. The method of any of embodiments 77-97, wherein the nanoparticle comprises at least one polymer, cationic polymer, or cationic block co-polymer on the nanoparticle surface.

99. The method of any of embodiments 77-98, wherein the nanoparticle comprises a cationic block co-polymer comprising PEG (e.g., a PEG having a molecular weight of about 1-10, 2-8, 4-6, or about 5 kD) and a poly-lysine, (e.g., a poly-lysine having an average length of 10-50, 20-40, or about 30 amino acids)

100. The method of any of embodiments 77-99, wherein the composition comprises a compound that stabilizes the nanoparticle in solution or on the cell surface and/or increases the interaction between the nanoparticle and the surface of the nucleated cell, e.g., protamine, chitosan, a carbohydrate, a heparan-sulfate proteoglycan, a natural polymer, a polysaccharide, a dextramer, cellulose, fibronectin, collagen, fibrin, or a proteoglycan.

101. The method of any of embodiments 77-100, wherein the conservation agent is a stimulatory molecule for sustaining nucleated cell viability, proliferation, cytotoxic activity or activation.

102. The method of any of embodiments 77-101, wherein the conservation agent comprises an IL-15 molecule complexed, e.g., covalently or noncovalently, with a polypeptide comprising:
a first domain comprising the amino acid sequence of SEQ ID NO: 3 or SEQ ID NO: 4, or an amino acid sequence having at least 80%, 85%, 90%, 95%, 96%, 97%, 98%, or 99% identity thereto, and having IL-15 binding activity or a first domain comprising the amino acid sequence of SEQ ID NO: 7 or SEQ ID NO: 8, or an amino acid sequence having at least 80%, 85%, 90%, 95%, 96%, 97%, 98%, or 99% identity thereto, and having IL-15 binding activity; and
optionally, a second, heterologous domain, e.g., an antibody molecule, e.g., a Fab fragment, a Fab2 fragment, or scFv; a heavy chain antibody fragment; an Fc fragment; or an affibody fragment or derivative, e.g., a sdAb (nanobody) fragment.

103. The method of any of embodiments 77-102, wherein the nanoparticle comprises
an IL-15$^{N72D}$ polypeptide of SEQ ID NO: 6 or an amino acid sequence having at least 80%, 85%, 90%, 95%, 96%, 97%, 98%, or 99% identity thereto which has IL-15Ra binding activity;
a sushi-Fc polypeptide of SEQ ID NO: 5 or an amino acid sequence having at least 80%, 85%, 90%, 95%, 96%, 97%, 98%, or 99% identity thereto, which has IL-15 binding activity;
a cationic block co-polymer comprising PEG having a molecular weight of about 1-10, 2-8, 4-6, or about 5 kD and a poly-lysine having an average length of 10-50, 20-40, or about 30 amino acids; and
optionally, an antibody molecule to CD45.

104. The method of any of embodiments 77-103, wherein the conservation agent comprises a cytokine molecule, growth factor molecule, or a costimulatory molecule 105. The method of any of embodiments 77-104, wherein the composition comprises a second conservation agent which comprises a cytokine, e.g., IL2, IL6, IL7, IL12, IL15, IL17, IL18, IL21, IL-23, IL-4, IL1alpha, IL1beta, IL-5, IFNgamma, TNFa, IFNalpha, IFNbeta, GM-CSF, or GCSF, or a variant, e.g., a superagonist thereof.

106. The method of any of embodiments 77-105, wherein the composition comprises an antibody molecule or agonist ligand against a costimulatory molecule, e.g., wherein the costimulatory molecule is chosen from OX40, CD28, GITR, VISTA, CD40, CD3, or an agonist of CD137.

107. The method of any of embodiments 77-106, wherein the composition, e.g., the nanoparticle, comprises an entity that reduces, e.g. inhibits, diminishes or decreases internalization, by the nucleated cell, of the nanoparticle.

108. The method of any of embodiments 77-107, wherein the composition, e.g., the nanoparticle, comprises an antibody molecule to CD45, CD11a (integrin alpha-L), CD18 (integrin beta-2), CD11b, CD11c, CD25, CD8, or CD4.

109. The method of any of embodiments 77-108, wherein the nanogel is a high-density protein structure (e.g., greater than 80% protein by weight), and/or wherein the protein is cross-linked by a cross-linking molecule that upon degradation releases the proteins in a native form.

110. The method of any of embodiments 77-109, wherein the nanoparticle comprises a nanogel that is cross linked by a reversible linker that is sensitive to redox (e.g., disulfide) or pH (e.g., hydrolysable groups) or enzymes (e.g., proteases).

111. A method for freezing a nucleated cell and a nanoparticle, wherein the cells are frozen at less than negative 10 degrees centigrade and thawed after at least 1 hour, wherein said nanoparticle comprises at least one agent that is released from the nanoparticle after thawing that keeps the cells viable to a higher extent than a composition of a nucleated cell without a nanoparticle.

112. The method of embodiment 111, wherein the agent is a stimulatory molecule for sustaining nucleated cell viability.

113. The method according to any of embodiments 111-112, wherein the nucleated cell is a lymphocyte.

114. The method according to any of embodiments 111-113, wherein nanoparticle is associated with the surface of the nucleated cell.

115. The method according to any of embodiments 111-114, wherein the nanoparticle is covalently conjugated to the surface of the nucleated cell.

EXAMPLES

Example 1: Formation of Protein Nanogel

Proteins are produced from suspension-adapted HEK 293 cells in serum-free media and then purified by protein A affinity and buffer exchanged into Dulbecco's phosphate buffered saline (DPBS).

Backpack protein nanogels comprising a crosslinked protein nanogel (backpacks) are formed as follows. Proteins or protein complexes described herein are cross-linked into protein nanoparticles using excess of a degradable cross-linker. A suitable protein complex is the IL-15 superagonist described in Rubinstein et al PNAS 103:24 p. 9166-9171 (2006).

In some embodiments, the protein complex comprises a wild-type human IL-15 protein sequence as follows:

(SEQ ID NO: 1)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

A suitable crosslinker is Bis[2-(N-succinimidyl-oxycarbonyloxy)ethyl] disulfide, which contains two N-hydroxysuccinimide (NHS) ester groups joined together by a flexible disulfide-containing linker.

After incubation at room temperature the reaction is diluted with DPBS to a desired final concentration. Protein nanogels are then purified from linker leaving groups (which comprise molecular fragments of the linker that are removed as part of the cross-linking reaction) and unreacted linker by buffer exchange into DPBS using a Zeba column. Protein nanogels are optionally further conjugated with a polymer, an antibody molecule, or both of a polymer and an antibody molecule. A suitable antibody molecule is an anti-CD45 monoclonal antibody (clone BC8; purified from hybridoma culture; ATCC cat. no. HB-10507). Buffer-exchanged protein nanogels are then diluted with an equal volume of Hank's Balanced Salt Solution (HBSS) to a desired final concentration for use in downstream assays such as association with activated primary T cells, primary NK cells, NK cell line NK-92 (ATCC cat. No. CRL-2407), or modified versions of these T and NK cells.

Formation of the protein nanogel is evaluated by SDS-PAGE, size-exclusion chromatography (SEC) and dynamic light scattering (DLS) analyses. When the protein nanogel is formed, free protein or protein complex is converted into a crosslinked protein by the degradable linker. This crosslinking results in a larger hydrodynamic radius of the particle, which manifests as a protein particle that does not efficiently migrate by polyacrylamide gel electrophoresis (SDS-PAGE). In analysis by SEC using a BioSep™ SEC-s4000 column (Phenomenex Inc.) with PBS (pH 7.2) as eluent (flow rate 0.5 mL/min) on a Prominence HPLC system equipped with a photodiode array (Shimadzu Corp.), a protein nanogel will traveled with a faster elution time, consistent with a larger molecular species. Nanogel size and polydispersity is analyzed by dynamic light scattering (DLS) at 90 degrees angle on a NanoBrook Omni particle sizer (NanoBrook Instruments Corp.)

Example 2: Isolation of T Cells, B Cells and NK Cells

T cells and NK cells are isolated from healthy donors. One day old leukopack cells (Biospecialties, Inc.) are diluted 1:1 in volume with DPBS and layered on a density cushion (Lymphoprep, Stemcell Tech.) in a 50 ml tube (35 ml of diluted leukopack on top of 15 ml of Lymphoprep). After 30 minutes centrifugation at 800 g, mononuclear cells are harvested at the interface between lymphoprep and DPBS. Cells are washed in 50 ml of DPBS 3 times to remove residual lymphoprep and cell debris. T cells and NK cells are isolated by sequential magnetic beads sorting using anti-CD3 (or anti-CD8) and anti-CD56 conjugated beads (Miltenyi), respectively, according to the manufacturer's instructions. Briefly, LS columns are equilibrated with 3 ml of ice-cold DPBS while antibody-conjugated beads are incubated with mononuclear cells (30 minutes at +4° C.). After loading the cells in the column, 3 washes with 3 ml of ice-cold DPBS are performed and cells flushed out of the column with 5 ml of ice-cold DPBS.

After isolation, T cells are rested in complete media (CM-T): IMDM (Lonza), Glutamaxx (Life Tech), 20% FBS (Life Tech), 2.5 ug/ml human albumin (Octapharma), 0.5 ug/ml Inositol (Sigma) supplemented with 20 ng/ml of interleukin-2 (IL-2) for at least 2 hours. After isolation, NK cells are rested in NK complete media (CM-NK): Xvivo10 containing recombinant transferrin (Lonza), Glutamaxx (Life Tech), 5% human serum AB (Corning) supplemented with 20 ng/ml of interleukin-2 (IL-2) for at least 2 hours.

Example 3: Activation of T Cells Before Labeling

Prior to association with protein nanogels, pooled CD4$^+$ and CD8$^+$ T cells (which are the dominant cell type resulting from anti-CD3 selection described in Example 2) or isolated CD8$^+$ T cells, each obtained as described in Example 2, are first activated with CD3/CD28 Dynabeads (ThermoFisher, Cat. No. 1132D) following the manufacturer's instructions. T cells and CD3/CD28 Dynabeads are incubated in CM-T supplemented with 20 ng/ml of interleukin-2 (IL-2) for 2 days at 37° C. and 5% $CO_2$. CD3/CD28 Dynabeads are then removed from the T cells by magnetic separation.

Example 4: Association of Protein Nanogel to T Cell and Cryopreservation

Protein nanogels (Backpack pillows) are associated with activated human T cells and subjected to a freeze-thaw cycle. Briefly, backpack pillows are prepared as described in Example 1. To support downstream flow cytometric analysis, the backpack pillow is generated using 3 mass % Alexa-647-labeled protein or protein complex and 97 mass % unlabeled protein or protein complex. Protein or protein complex is fluorescently labeled using an Alexa-Fluor-647 labeling kit according to the manufacturer's instructions (ThermoFisher, cat. no. A20186, 100 ug scale kit; or cat. no. A20173, 1 mg scale kit). All other steps for protein nanogel synthesis are performed as described in Example 1.

Activated T cells prepared according to Example 3 are washed with DPBS and incubated for 1 hr at 37° C. at a final cell density of approximately $10^8$ cells/mL with protein nanogel backpack pillows. The solution is mixed every 10-15 min by inversion or gentle vortexing. Cells are then resuspended in cell freezing media containing FBS with 5% dimethyl sulfoxide (DMSO) or serum-free freezing media (Bambanker, Lymphotec, Inc. cat. no. BB02) as specified, at a density of $10^7$ cells/mL, and transferred to cryogenic vials to be frozen in a Mr. Frosty™ freezing container (Nalgene) as described by the manufacturer. Following overnight incubation at −80° C. in the Mr. Frosty™ container, cells are thawed by incubation in a water bath at 37° C. and washed with DPBS to remove freezing medium and unbound backpacks. Alternative freezing lengths are described in other Examples below (e.g. 2 hours or 2 weeks). Cells are then cultured in CM-T with 20 ng/mL IL-2 at 37° C. and 5% $CO_2$. Association of backpack pillows with the T cells is monitored by flow cytometry using a FACSCelesta™ flow cytometer with FACSDiva™ software (BD Biosciences), to quantify persistent association of backpack pillows with the T cells following the freezing and thawing.

Example 5: Association of Protein Nanogel to Primary NK Cell and NK-92 Cell Line Protein nanogels (backpack pillows) are associated with primary human NK cells (isolated as described in Example 2) and NK-92 cells (ATCC cat. No. CRL-2407) and subjected to a freeze-thaw cycle. Protein nanogel synthesis is performed as described in Example 1.

NK cells are washed with DPBS and incubated for 1 hr at 37° C. at a final cell density of approximately $10^8$ cells/mL with protein nanogel backpack pillows. The solution is mixed every 10-15 min by inversion or gentle vortexing. Cells are then resuspended in serum-free freezing media (Bambanker, Lymphotec, Inc. cat. no. BB02) at a density of $10^7$ cells/mL, and transferred to cryogenic vials to be frozen in a Mr. Frosty™ freezing container (Nalgene) as described by the manufacturer. Following 2 hours incubation at −80° C. in the Mr. Frosty™ container, cells are thawed by incubation in a water bath at 37° C. and washed with DPBS to remove freezing medium and unbound backpacks. Alternative freezing lengths are described in other Examples (e.g. 2 hours or 2 weeks). Cells are then cultured in CM-NK with 20 ng/mL IL-2 at 37° C. and 5% $CO_2$.

Example 6: Cell Expansion of CD8 T Cell in IL-2 Containing CM-T

CD8 T cells are incubated with backpack pillows before freezing in FBS+5% DMSO overnight. Upon thawing, backpack-associated T cells are cultured in IL-2 containing CM-T, along with control CD8 T cell treated the same way but without backpacks. The number of live cells is measured at timepoints (e.g., 4 hours and 48 hours) after thawing to quantify the recovery speed of CD8 T cells with and without the backpack pillows.

Example 7: Cell Expansion of CD3 T Cell in IL-2 Free CM-T

CD3 T cells are incubated with backpack pillows before freezing in serum-free media (Bambanker). Upon thawing, backpack-associated CD3 T cells are cultured in IL-2 free CM-T, along with control CD3 T cell treated the same way but without backpacks. Suitable controls include CD3 T cells thawed and cultured in IL-2 free CM-T, CD3 T cells thawed and cultured in soluble IL-2 containing (20 ng/ml) CM-T, and CD3 T cells thawed and cultured in a soluble (non-crosslinked) form of the same protein used in the protein nanogel. The number of live cells is measured at timepoints (e.g., 16 hours, 2 days, 7 days, and 9 days) after thawing.

Example 8: Cell Expansion of NK-92 Cell Line and Primary NK Cells

NK-92 cells and primary NK cells are incubated with backpack pillows before freezing in serum-free media (Bambanker). Upon thawing, backpack-associated cells are cultured in IL-2 free CM-NK. Suitable controls include primary NK cells and NK-92 cells thawed and cultured in IL-2 free CM-NK, primary NK cells and NK-92 cells thawed and cultured in soluble IL-2 containing (20 ng/ml) CM-NK, primary NK cells and NK-92 cells thawed and cultured in a soluble (non-crosslinked) form of the same protein used in the protein nanogel, and NK-92 cells associated with backpack pillows but not cryopreserved and cultured in IL-2 free CM-NK. The number of live cells is measured timepoints after thawing (e.g., 16 hours, 1 day, 5 days, 6 days, and 9 days).

Example 9: T Cell Subsets and Activation

CD3 T cells treated as in Example 7 are further characterized by flow cytometry using the following fluorochrome-conjugated antibodies (BD Biosciences): CD4, CD8, CD45RA and CD45RO. The proportion of CD8 T cells and their activation state are measured.

Example 10: Short Term Potency of Activated CD3 T Cells Against Target Cell

The cytotoxic activity of CD3 T cells treated as in Example 7 is characterized 1 day after thawing. CD3 T cells are co-cultured with target cells (Daudi, ATCC) previously labeled with PKH67 (Sigma) at different effector to target (E:T) ratios. Killing of target cells is measured by flow cytometry after 16 hours. The co-culture is performed in CM-T with IL-2 (20 ng/ml) for 16 hours. Dead cells are stained with Propidium Iodide (PI, BD Biosciences) and analyzed by flow cytometry. The fraction killing is calculated after dividing the number of PI+ PKH67+ cells by the total number of PKH67+ cells and subtracting the ratio obtained from culturing the target cells alone (background target cell viability). Cell co-culture supernatants from the cytotoxicity assay are harvested after centrifugation of the cells and stored at −20° C. IFNg concentration in supernatants is measured by ELISA (R&D) following the manufacturer's specifications.

Example 11: Long Term Potency of Activated CD8 T Cells Against Target Cells

CD8 T cells are incubated with backpack pillows and either cryopreserved or returned to culture with IL-2 free CM-T. Their cytotoxic activity is compared after 18 days of culture in IL-2 free CM-T. CD8 T are co-cultured with target cells (Daudi, ATCC) previously labeled with PKH67 (Sigma) at different effector to target (E:T) ratios. Killing of target cells is measured by flow cytometry after 16 hours. The co-culture is performed in CM-T with IL-2 (20 ng/ml) for 16 hours. Dead cells are stained with Propidium Iodide (BD Biosciences) and analyzed by flow cytometry. The fraction killing is calculated after dividing the number of PI+ PKH67+ cells by the total number of PKH67+ cells and subtracting the ratio obtained from culturing the target cells alone (background target cell viability). Cell co-culture supernatants from the cytotoxicity assay are harvested after centrifugation of the cells and stored at −20° C. IFNg concentration in supernatants is measured by ELISA (R&D) following the manufacturer's specifications.

Example 12: Potency of Activated CD8 T Cells Against Target Cell in Presence of IL-2

The cytotoxic activity of CD8 T cells treated as in Example 6 is characterized. CD8 T cells are co-cultured with target cells (Daudi, ATCC) previously labeled with PKH67 (Sigma) at different effector to target (E:T) ratios. Killing of target cells is measured by flow cytometry after 16 hours. The co-culture is performed in CM-T with IL-2 (20 ng/ml) for 16 hours. Dead cells are stained with Propidium Iodide (BD Biosciences) and analyzed by flow cytometry. The fraction killing is calculated after dividing the number of PI+ PKH67+ cells by the total number of PKH67+ cells and subtracting the ratio obtained from culturing the target cells alone (background target cell viability). Cell co-culture supernatants from the cytotoxicity assay are harvested after centrifugation of the cells and stored at −20° C. IFNg concentration in supernatants is measured by ELISA (R&D) following the manufacturer's specifications.

Example 13: Potency of Primary NK Cells Against Target Cells

The cytotoxic activity of primary NK cells treated as in Example 8 is characterized. Primary NK cells are co-cultured with target cells (Daudi, ATCC) previously labeled with PKH67 (Sigma) at different effector to target (E:T) ratios. Killing of target cells is measured by flow cytometry after 16 hours. The co-culture is performed in CM-NK with IL-2 (20 ng/ml) for 16 hours. Dead cells are stained with Propidium Iodide (BD Biosciences) and analyzed by flow cytometry. The fraction killing is calculated after dividing the number of PI+ PKH67+ cells by the total number of PKH67+ cells and subtracting the ratio obtained from culturing the target cells alone (background target cell viability). Cell co-culture supernatants from the cytotoxicity assay are harvested after centrifugation of the cells and stored at −20° C. IFNg concentration in supernatants are measured by ELISA (R&D) following the manufacturer's specifications.

Example 14: Generation of IL-15 Protein Variants

Figure 1B:
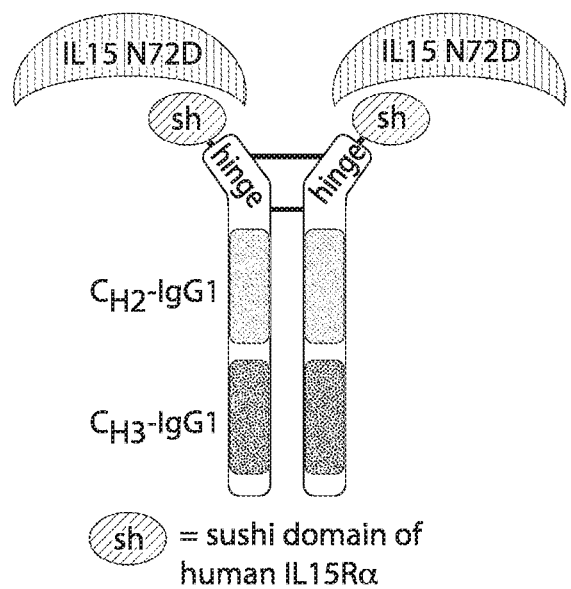

Two IL-15 protein variants were generated. A first IL-15 variant (hereafter referred to as IL-15$^{WT}$/sushi-Fc; see FIG. 1A) comprises a noncovalent complex of wild-type human IL-15 (SEQ ID NO: 1) with an Fc fusion of the sushi domain of human IL-15 receptor alpha (IL-15Ra; SEQ ID NO: 5). Wild-type IL-15 and IL-15Ra are given by GenBank Accession Nos. CAA62616.1 and AAI21141.1, respectively, which are herein incorporated by reference in their entireties. The second IL-15 variant (hereafter referred to as IL-15$^{N72D}$/sushi-Fc; see FIG. 1B) comprises a noncovalent complex of human IL-15 containing an N72D point mutation (SEQ ID NO: 6) with an Fc fusion of the sushi domain of human IL-15 receptor alpha (IL-15Ra; SEQ ID NO: 5). Proteins were produced from suspension adapted HEK 293 in serum-free media and then purified by protein A affinity and buffer exchanged into Dulbecco's phosphate buffered saline (DPBS).

```
Fc fusion of the sushi domain of human IL-15
receptor alpha:
                                        (SEQ ID NO: 5)
ITCPPPMSVEHADIWVKSYSLYSRERYICNSGFKRKAGTSSLTECVINKA

TNVAHWTTPSLKCIREPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

Human IL-15 containing an N72D point mutation:
                                        (SEQ ID NO: 6)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS
```

Example 15: Formation of Protein Nanogel

Backpack protein nanogels comprising a crosslinked protein nanogel (backpacks) were formed as follows. IL-15$^{WT}$/sushi-Fc or IL-15$^{N72D}$/sushi-Fc at a concentration of 15 mg/mL were cross-linked into protein nanoparticles using 25-fold molar excess of a degradable crosslinker. The crosslinker used in this study, Bis[2-(N-succinimidyl-oxycarbonyloxy)ethyl] disulfide, contains two N-hydroxysuccinimide (NHS) ester groups joined together by a flexible disulfide-containing linker as shown in Formula I.

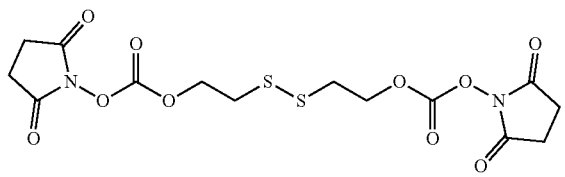

Formula I

After 30 min incubation at room temperature the reaction was diluted 10-fold with DPBS to a final cytokine concentration of 1.5 mg/mL. Protein nanogels were then purified from linker leaving groups (which comprise molecular fragments of the linker that are removed as part of the cross-linking reaction) and unreacted linker by buffer exchange into DPBS using a Zeba column (7,000 or 40,000 MW cut-off, available from Thermo-Fisher). Zeba columns were used according to the manufacturer's instructions, including equilibrating the column in DPBS by three consecutive washes with DPBS to facilitate buffer exchange, followed by application of the reaction products. Buffer-exchanged protein nanogels at a cytokine concentration of approximately 1-1.5 mg/mL were diluted with an equal volume of Hank's Balanced Salt Solution (HBSS) to a final concentration of approximately 0.5-0.75 mg/mL for use in downstream assays such as association with activated primary T cells, primary NK cells, NK cell line NK-92 (ATCC cat. No. CRL-2407), or modified versions of these T and NK cells.

Figure 2:
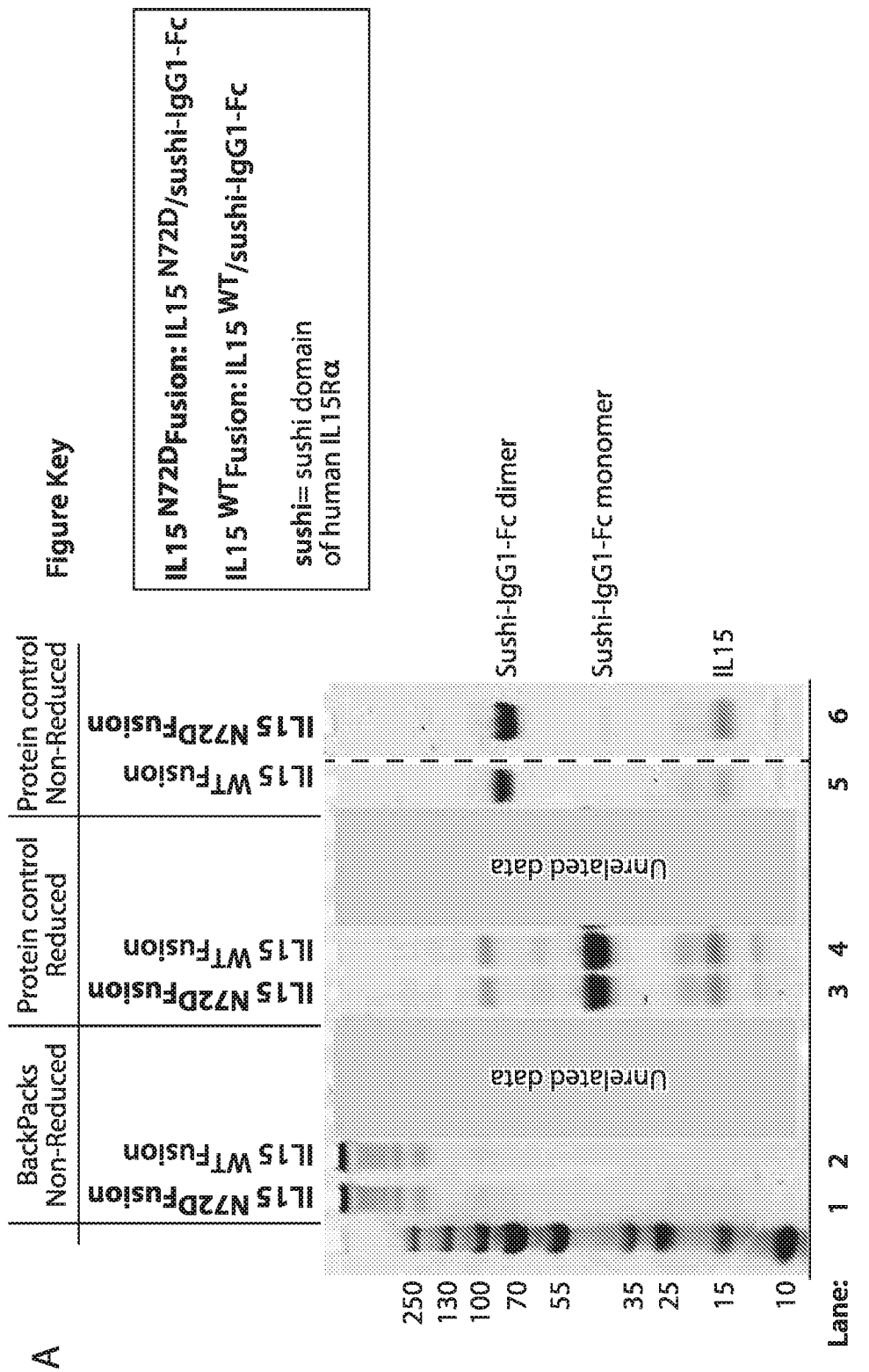
FIG. 2 depicts SDS-PAGE analysis of IL15/sushi-IgG1-Fc constructs used for protein nanogel (backpacks) formation. Analysis of IL-15$^{WT}$/sushi-Fc (black) and IL-15$^{N72D}$/sushi-Fc (blue) protein nanogels following crosslinking with a reversible crosslinker (lanes 1 and 2). The resultant protein nanogels are highly crosslinked and do not efficiently enter the polyacrylamide gel. Controls showing reduced (lanes 3 and 4) and non-reduced (lanes 5 and 6) IL-15 variants are also included. Unrelated data on the same SDS-PAGE has been omitted from the figure.
Figure 3:
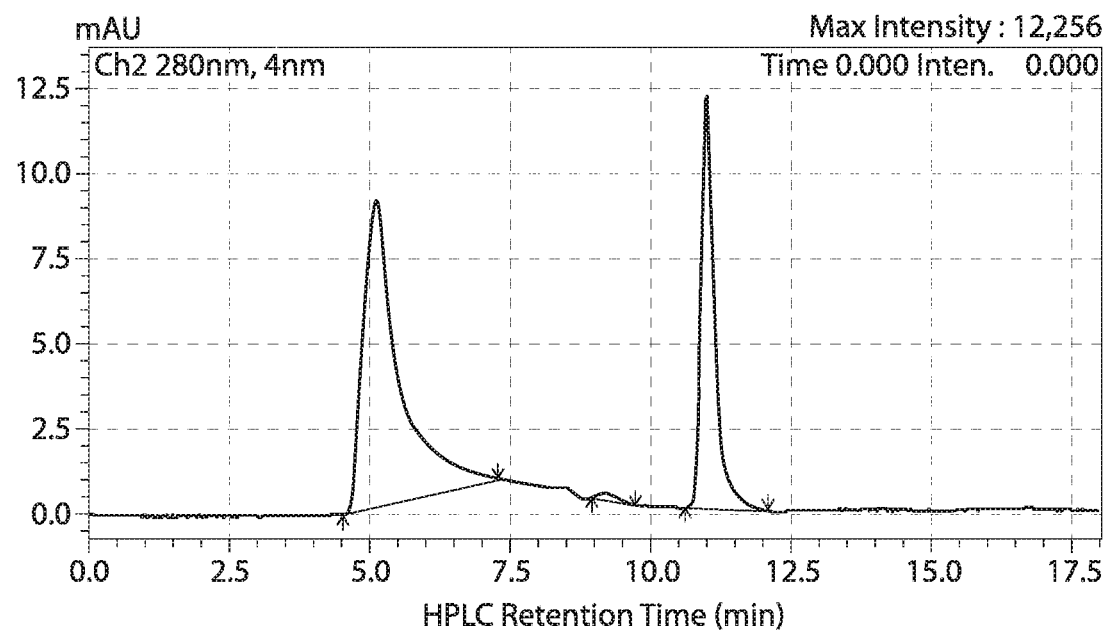
FIG. 3 shows cross-linked IL-15$^{N72D}$/sushi-Fc protein nanogel analyzed by HPLC on BioSep4000 size-exclusion chromatography column (peak at 11 minutes is unincorporated linker); peak at 5 minutes is cross-linked IL-15$^{N72D}$/sushi-Fc.
Figure 4:
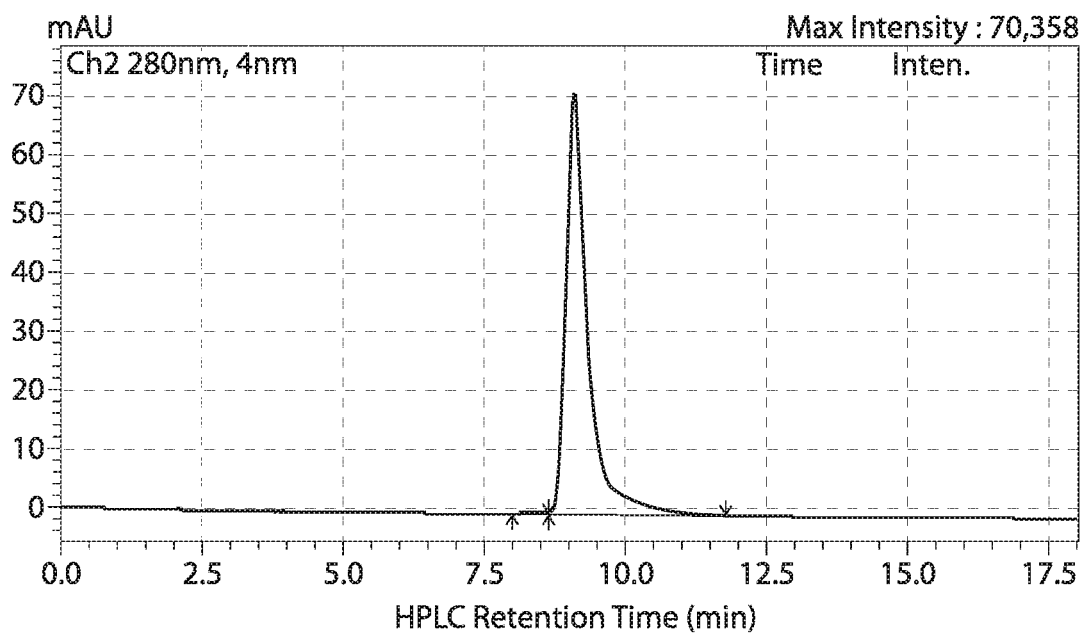
FIG. 4 shows non cross-linked IL-15$^{N72D}$/sushi-Fc as analyzed by HPLC on BioSep4000 size-exclusion chromatography column.

Formation of the protein nanogel was evaluated by SDS-PAGE, size-exclusion chromatography (SEC) and dynamic light scattering (DLS) analyses. When the protein nanogel is formed, free IL-15/sushi-Fc is converted into a crosslinked protein by the degradable linker. This cross-linking resulted in a larger hydrodynamic radius of the particle, which manifested as a protein particle that did not efficiently migrate by polyacrylamide gel electrophoresis (SDS-PAGE), see FIG. 2. Analysis by SEC using a BioSep™ SEC-s4000 column (Phenomenex Inc.) with PBS (pH 7.2) as eluent (flow rate 0.5 mL/min) on a Prominence HPLC system equipped with a photodiode array (Shimadzu Corp.) revealed that the protein nanogel traveled with a faster elution time, consistent with a larger molecular species (FIG. 3). Comparison of HPLC traces of the protein nanogel (FIG. 3) with the free (noncrosslinked) protein (FIG. 4) revealed a minimal amount of free protein remaining in the cross-linked nanogel, suggesting nearly complete conversion of the protein to crosslinked nanogel. Nanogel size and polydispersity were analyzed by dynamic light scattering (DLS) at 90 degrees angle on a NanoBrook Omni particle sizer (NanoBrook Instruments Corp.), see Table 1. The hydrodynamic diameter of uncrosslinked IL-15$^{N72D}$/sushi-Fc was estimated to be ~10 nm based on the radius of similarly sized molecules (IgG).

TABLE 1

Cross-linked particle sizes based on DLS

| Sample | Intensity-Based Size (nm) | Number-Based Size (nm) | Polydispersity |
|---|---|---|---|
| Cross-linked IL-15$^{N72D}$/sushi-Fc | 189 | 66 | 0.23 |
| IL-15$^{N72D}$/sushi-Fc + PEG5k-polyK30 | 220 | 68 | 0.26 |
| Cross-linked IL-15$^{N72D}$/sushi-Fc + anti-CD45 IgG | 230 | 80 | 0.23 |
| IL-15$^{N72D}$/sushi-Fc + PEG5k-polyK30 + anti-CD45 IgG | 299 | 80 | 0.29 |

Example 16: Formation of Protein Nanogel with Polycationic Polymer on Surface

Figure 5:
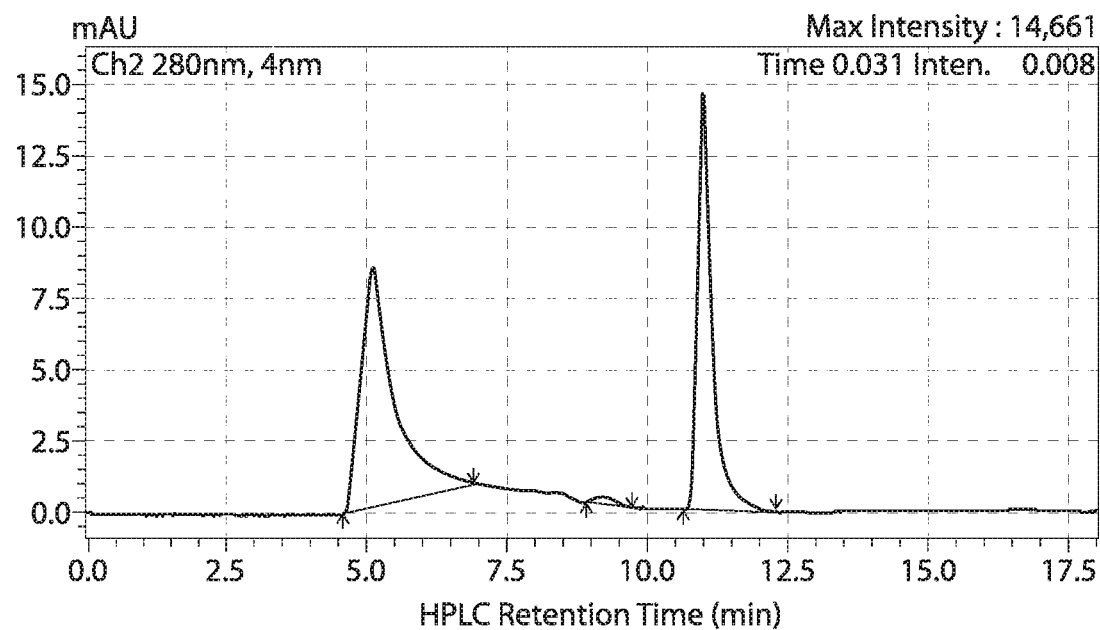
FIG. 5 shows HPLC of cross-linked IL-15$^{N72D}$/sushi-Fc protein nanogel functionalized with polyK30 on BioSep4000 size-exclusion chromatography column.

Protein nanogels (backpack pillows) comprising a protein nanogel with cationic polymer surface were formed as follows. IL-15$^{WT}$/sushi-Fc or IL-15$^{N72D}$/sushi-Fc at a concentration of 15 mg/mL were cross-linked into protein nanoparticles using 25-fold molar excess of the degradable crosslinker specified in Formula I. After 30 min incubation at room temperature the reaction was diluted 10-fold with DPBS to a final cytokine concentration of 1.5 mg/mL. Protein nanogels were then purified from linker leaving groups (which comprise molecular fragments of the linker that are removed as part of the cross-linking reaction) and unreacted linker by buffer exchange into DPBS using a Zeba column (7,000 or 40,000 MW cut-off, available from Thermo-Fisher). Zeba columns were used according to the manufacturer's instructions, including equilibrating the column in DPBS by three consecutive washes with DPBS to facilitate buffer exchange, followed by application of the reaction products. Buffer-exchanged protein nanogels at a cytokine concentration of approximately 1-1.5 mg/mL were then conjugated with a polyethylene glycol-polylysine (PEG-polyK) block copolymer: PEG5k-polyK30 (Alamanda Polymers cat. no. 050-KC030), which is a block co-polymer comprising 5 kiloDalton (kD) polyethylene glycol (PEG5k) and a 30 amino acid polylysine polymer (polylysine30 or polyK30), or PEG5k-polyK200 (Alamanda Polymers ca. no. 050-KC200). PEG5k-polyK30 or PEG5k-polyK200 were reconstituted to 10 mg/mL in DPBS and added to protein nanogels at a final block copolymer concentration of 50 ug/mL and incubated at room temperature for 30 min. Size and polydispersity of surface functionalized nanoparticles were analyzed by dynamic light scattering (DLS) at 90 degrees angle on a NanoBrook Omni particle sizer (NanoBrook Instruments Corp.), See Table 1, and relative conversion to nanoparticle was evaluated by size-exclusion chromatography using a BioSep™ SEC-s4000 column (Phenomenex Inc.) on a Prominence HPLC system with PBS (pH 7.2) as eluent (flow rate 0.5 mL/min) equipped with a photodiode array (Shimadzu Corp.), see FIG. 5.

The final backpack-pillow protein nanogels were diluted with an equal volume of Hank's Balanced Salt Solution (HBSS) to a final concentration of approximately 0.5-0.75 mg/mL for use in downstream assays such as association with activated primary T cells, primary NK cells, NK cell line NK-92 (ATCC cat. No. CRL-2407), or modified versions of these T and NK cells.

Example 17: Formation of Protein Nanogel with Surface Bound Affinity Ligand

Protein nanogels (backpack pillows) comprising a protein nanogel with surface bound affinity ligand and cationic polymer surface were formed as follows. IL-15$^{WT}$/sushi-Fc or IL-15$^{N72D}$/sushi-Fc at a concentration of 15 mg/mL were cross-linked into protein nanoparticles using 25-fold molar excess of the degradable crosslinker specified in Formula I. After 30 min incubation at room temperature the reaction was diluted 10-fold with DPBS to a final cytokine concentration of 1.5 mg/mL. An anti-CD45 monoclonal antibody (clone BC8; purified from hybridoma culture; ATCC cat. no. HB-10507) was then conjugated to the cross-linked protein nanoparticle by adding the antibody to a final concentration of 50 ug/mL and incubated 30-60 min at room temperature. Protein nanogels with surface conjugated anti-CD45 antibody were then purified from linker leaving groups (which comprise molecular fragments of the linker that are removed as part of the cross-linking reaction) and unreacted linker by buffer exchange into DPBS using a Zeba column (7,000 or 40,000 MW cut-off, available from Thermo-Fisher). Zeba columns were used according to the manufacturer's instructions, including equilibrating the column in DPBS by three consecutive washes with DPBS to facilitate buffer exchange, followed by application of the reaction products.

Buffer-exchanged protein nanogels at a cytokine concentration of approximately 1-1.5 mg/mL were diluted with an equal volume of Hank's Balanced Salt Solution (HBSS) to a final concentration of approximately 0.5-0.75 mg/mL for use in downstream assays such as association with activated primary T cells, primary NK cells, NK cell line NK-92 (ATCC cat. No. CRL-2407), or modified versions of these T and NK cells.

Figure 6:
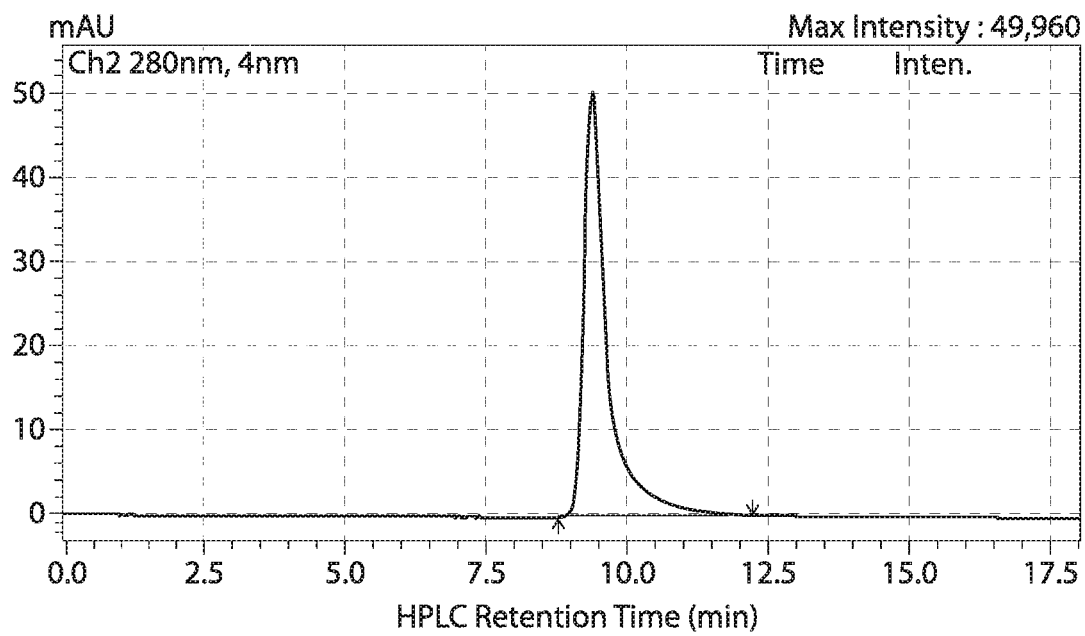
FIG. 6 shows non-crosslinked anti-CD45 IgG analyzed by HPLC on BioSep4000 size-exclusion chromatography column.
Figure 7:
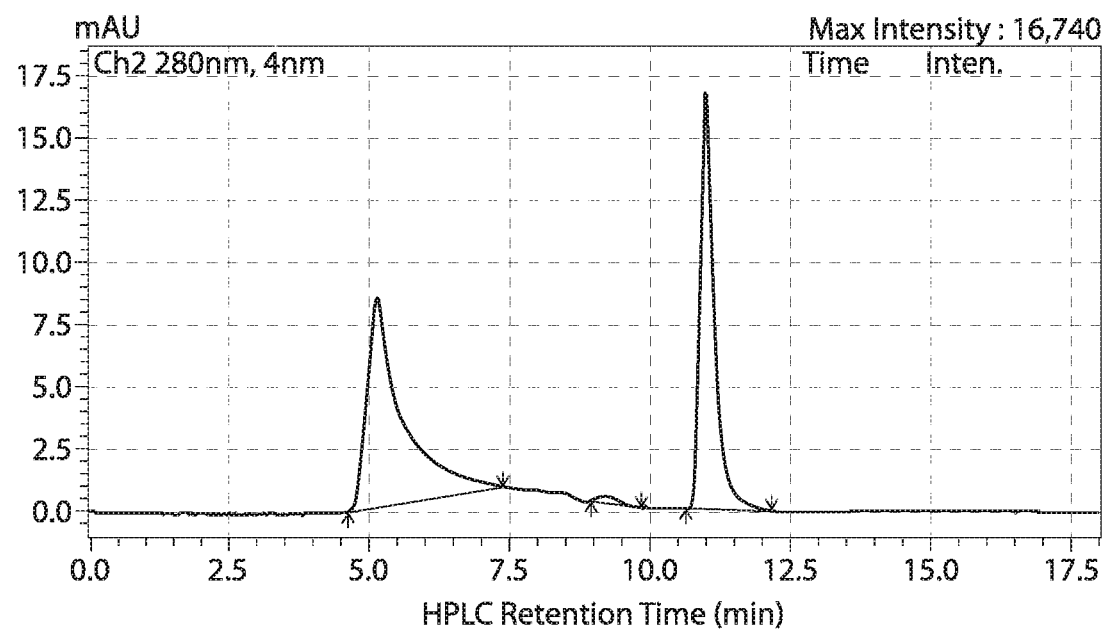
FIG. 7: Cross-linked IL-15$^{N72D}$/sushi-Fc protein nanogel functionalized with anti-CD45 IgG (same initial concentration of anti-CD45 IgG as above) analyzed by HPLC on BioSep4000 size-exclusion chromatography column.

Size and polydispersity of surface functionalized nanoparticles were analyzed by DLS (Table 1). Efficiency of incorporation of the anti-CD45 antibody was evaluated by SEC on a BioSep™ SEC-s4000 column (Phenomenex Inc.): comparison of free anti-CD45 antibody (FIG. 6) to anti-CD45 surface functionalized protein nanogels (FIG. 7) reveal minimal free IgG in the nanogel sample, indicating nearly complete conjugation of the antibody to the nanogel surface.

Figure 8:
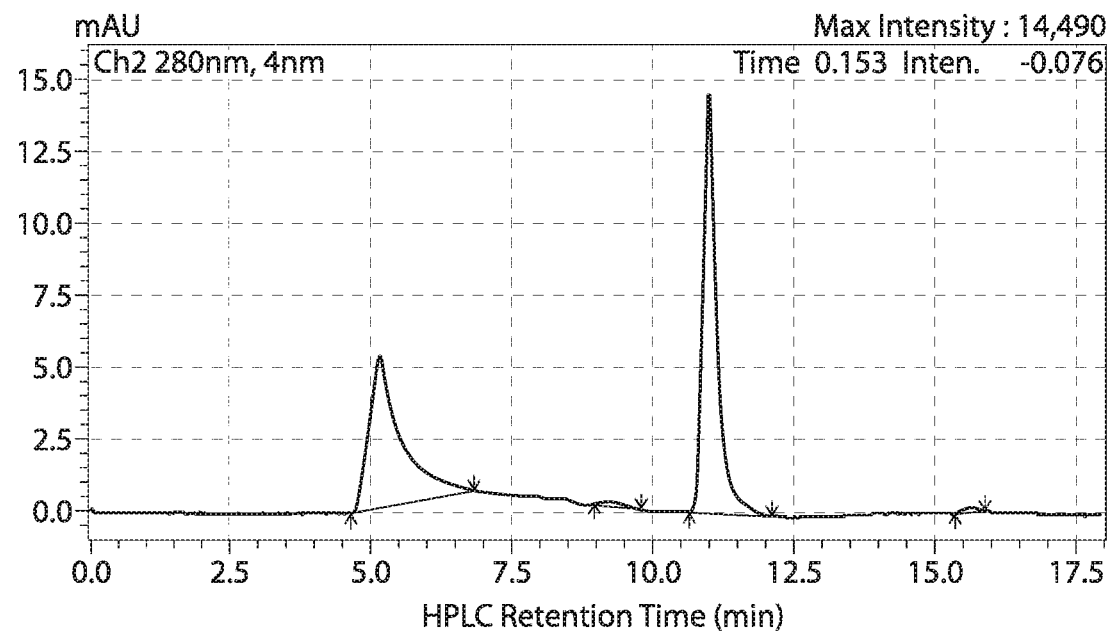
FIG. 8: Cross-linked IL-15$^{N72D}$/sushi-Fc protein nanogel functionalized with anti-CD45 IgG and polyK30 analyzed by HPLC on BioSep4000 size-exclusion chromatography column.

Example 18: Formation of Protein Nanogel with Surface Bound Affinity Ligand and Cationic Polymer on Surface Protein nanogels (backpack pillows) comprising a protein nanogel with surface bound affinity ligand and cationic polymer surface were formed as follows. IL-15$^{WT}$/sushi-Fc or IL-15$^{N72D}$/sushi-Fc at a concentration of 15 mg/mL were cross-linked into protein nanoparticles using 25-fold molar excess of the degradable crosslinker specified in Formula I. After 30 min incubation at room temperature the reaction was diluted 10-fold with DPBS to a final cytokine concentration of 1.5 mg/mL. An anti-CD45 monoclonal antibody (clone BC8; purified from hybridoma culture; ATCC cat. no. HB-10507) was then conjugated to the cross-linked protein nanoparticle by adding the antibody to a final concentration of 50 ug/mL and incubated 30-60 min at room temperature. Protein nanogels with surface conjugated anti-CD45 antibody were then purified from linker leaving groups (which comprise molecular fragments of the linker that are removed as part of the cross-linking reaction) and unreacted linker by buffer exchange into DPBS using a Zeba column (7,000 or 40,000 MW cut-off, available from Thermo-Fisher). Zeba columns were used according to the manufacturer's instructions, including equilibrating the column in DPBS by three consecutive washes with DPBS to facilitate buffer exchange, followed by application of the reaction products. Buffer-exchanged protein nanogels at approximately 1-1.5 mg/mL were then conjugated with PEG5k-polyK30 (Alamanda Polymers cat. no. 050-KC030) or PEG5k-polyK200 (Alamanda Polymers ca. no. 050-KC200). PEG5k-polyK30 or PEG5k-polyK200 were first reconstituted to 10 mg/mL in DPBS and then added to protein nanogels at a final block copolymer concentration of 50 ug/mL and incubated at room temperature for 30 min. Size and polydispersity of surface functionalized nanoparticles were analyzed by DLS (Table 2) on a NanoBrook Omni particle sizer (NanoBrook Instruments Corp.) and by SEC using a BioSep™ SEC-s4000 column (Phenomenex Inc.) on a Prominence HPLC system with PBS (pH 7.2) as eluent (flow rate 0.5 mL/min) equipped with a photodiode array (Shimadzu Corp.), FIG. 8.

TABLE 2

Size of nanoparticles after polyK addition.
Potential aggregation is shown as
bolded and italicized numbers in Table 2
Size of Nanoparticles after polyK addition (nm)

| PolyK | Concentration of polyK | | |
|---|---|---|---|
| | 10 mg/mL | 1 mg/mL | 0.1 mg/mL |
| PEG5kpolyK200 | *1,530* | *618* | *166* |
| PEG20kpolyK100 | *204* | *140* | 90 |
| PEG20kpolyK50 | 105 | 93 | 86 |
| PEG5KpolyK30 | *1,239* | 106 | 85 |
| PEG20kpolyK10 | 95 | 87 | 88 |
| No PolyK | 89 | | |

The final backpack-pillow protein nanogels were diluted with an equal volume of Hank's Balanced Salt Solution (HBSS) to a final concentration of approximately 0.5-0.75 mg/mL for use in downstream assays such as association with activated primary T cells, primary NK cells, NK cell line NK-92 (ATCC cat. No. CRL-2407), or modified versions of these T and NK cells.

Loading of fluorescently labeled nanoparticles onto activated naïve T-cells was quantified as shown below in Table 3.

| Amount and type of polymer in nanoparticle | Mean fluorescent intensity |
|---|---|
| No polyK | 34,228 |
| 1 mg/ml PEG5k polyK200 | 561 |
| BC8 1 mg/ml PEG5k polyK200 | 2,758 |
| 0.1 mg/ml PEG5k polyK200 | 11,151 |
| 1 mg/ml PEG20k polyK100 | 92,912 |
| 10 mg/ml PEG20k polyK50 | 26,048 |
| 1 mg/ml PEG5k polyK30 | 127,922 |
| 50 mg/ml PEG20k polyK10 | 8,726 |

Example 19: Isolation of T Cells, B Cells and NK Cells

T cells and NK cells were isolated from healthy donors. One day old leukopack cells (Biospecialties Inc.) were diluted 1:1 in volume with DPBS and layered on a density cushion (Lymphoprep, Stemcell Tech.) in a 50 ml tube (35 ml of diluted leukopack on top of 15 ml of Lymphoprep). After 30 minutes centrifugation at 800 g, mononuclear cells were harvested at the interface between lymphoprep and DPBS. Cells were washed in 50 ml of DPBS 3 times to remove residual lymphoprep and cell debris. T cells and NK cells were isolated by sequential magnetic beads sorting using anti-CD3 (or anti-CD8) and anti-CD56 conjugated beads (Miltenyi), respectively, according to the manufacturer's instructions. Briefly, LS columns were equilibrated with 3 ml of ice-cold DPBS while antibody-conjugated beads were incubated with mononuclear cells (30 minutes at +4° C.). After loading the cells in the column, 3 washes with 3 ml of ice-cold DPBS were performed and cells flushed out of the column with 5 ml of ice-cold DPBS.

After isolation, T cells were rested in complete media (CM-T): IMDM (Lonza), Glutamaxx (Life Tech), 20% FBS (Life Tech), 2.5 ug/ml human albumin (Octapharma), 0.5 ug/ml Inositol (Sigma) supplemented with 20 ng/ml of interleukin-2 (IL-2) for at least 2 hours. After isolation, NK cells were rested in NK complete media (CM-NK): Xvivo10 containing recombinant transferrin (Lonza), Glutamaxx (Life Tech), 5% human serum AB (Corning) supplemented with 20 ng/ml of interleukin-2 (IL-2) for at least 2 hours.

Example 20: Activation of T Cells Before Labeling

Prior to association with protein nanogels, pooled CD4+ and CD8+ T cells (which are the dominant cell type resulting from anti-CD3 selection described in Example 19) or isolated CD8+ T cells, each obtained as described in Example 19, were first activated with CD3/CD28 Dynabeads (ThermoFisher cat. no. 1132D) following the manufacturer's instructions. T cells and CD3/CD28 Dynabeads were incubated in CM-T supplemented with 20 ng/ml of interleukin-2 (IL-2) for 2 days at 37° C. and 5% $CO_2$. CD3/CD28 Dynabeads were then removed from the T cells by magnetic separation.

Example 21: Association of Protein Nanogel to T Cell and Cryopreservation

Protein nanogels (Backpack pillows) were associated with activated human T cells and subjected to a freeze-thaw cycle. Briefly, backpack pillows consisting of IL-15$^{N72D}$/sushi-Fc or IL-15$^{WT}$/sushi-Fc protein nanogels surface functionalized with a polycationic polymer (PEG5k-polyK30) were prepared as described in Example 16. To support downstream flow cytometric analysis, the backpack pillow was generated using 3 mass % Alexa-647-labeled IL-15$^{N72D}$/sushi-Fc and 97 mass % unlabeled IL-15$^{N72D}$/sushi-Fc. IL-15$^{N72D}$/sushi-Fc was fluorescently labeled using an Alexa-Fluor-647 labeling kit according to the manufacturer's instructions (ThermoFisher, cat. no. A20186, 100 ug scale kit; or cat. no. A20173, 1 mg scale kit). All other steps for protein nanogel synthesis were performed as described in Example 16.

Figure 9:
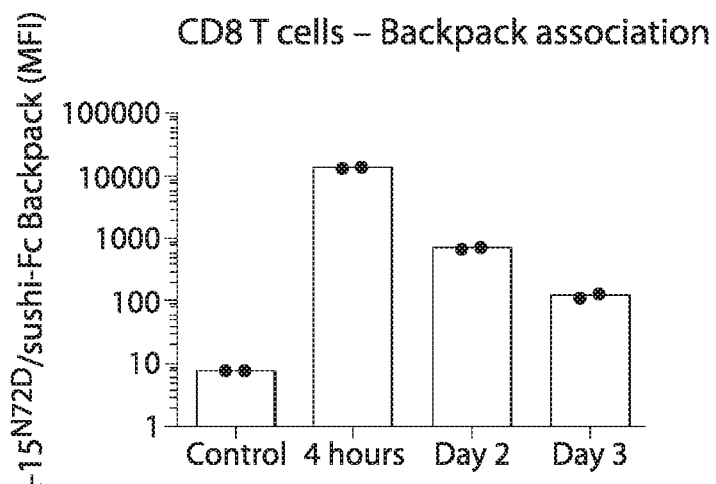
FIG. 9 depicts protein nanogel association with CD8 T cells. CD8 T cells were associated with IL-15$^{N72D}$/sushi-Fc protein nanogels (backpacks) containing 3% in weight of Alexa-647 conjugated IL-15$^{N72D}$/sushi-Fc. CD8 T cells were frozen in FBS+5% DMSO overnight. Upon thawing, CD8 T cells were cultured in IL-2 containing media (20 ng/ml) and their Alexa-647 fluorescence measured at the indicated time points by flow cytometry.

Activated T cells prepared according to Example 20 were washed with DPBS and incubated for 1 hr at 37° C. at a final cell density of approximately $10^8$ cells/mL with protein nanogel backpack pillows at an equivalent cytokine concentration of approximately 0.5-0.75 mg/mL. The solution was mixed every 10-15 min by inversion or gentle vortexing. Cells were then resuspended in cell freezing media containing FBS with 5% dimethyl sulfoxide (DMSO) or serum-free freezing media (Bambanker, Lymphotec, Inc. cat. no. BB02) as specified, at a density of $10^7$ cells/mL, and transferred to cryogenic vials to be frozen in a Mr. Frosty™ freezing container (Nalgene) as described by the manufacturer. Following overnight incubation at −80° C. in the Mr. Frosty™ container, cells were thawed by incubation in a water bath at 37° C. and washed with DPBS to remove freezing medium and unbound backpacks. Alternative freezing lengths are described in other Examples below (e.g. 2 hours or 2 weeks). Cells were then cultured in CM-T with 20 ng/mL IL-2 at 37° C. and 5% $CO_2$. Association of backpack pillows with the T cells was monitored by flow cytometry using a FACSCelesta™ flow cytometer with FACSDiva™ software (BD Biosciences), and revealed persistent association of backpack pillows with the T cells following the freezing and thawing (FIG. 9).

Example 22: Association of Protein Nanogel to Primary NK Cell and NK-92 Cell Line Protein nanogels (backpack pillows) were associated with primary human NK cells (isolated as described in Example 19) and NK-92 cells (ATCC cat. No. CRL-2407) and subjected to a freeze-thaw cycle. Briefly, backpack pillows of IL-15$^{N72D}$/sushi-Fc protein nanogels surface functionalized with a polycationic polymer (PEG5k-polyK30) were prepared as described in Example 16. All other steps for protein nanogel synthesis were performed as described in Example 16.

NK cells were washed with DPBS and incubated for 1 hr at 37° C. at a final cell density of approximately $10^8$ cells/mL with protein nanogel backpack pillows at an equivalent cytokine concentration of approximately 0.5-0.75 mg/mL. The solution was mixed every 10-15 min by inversion or gentle vortexing. Cells were then resuspended in serum-free freezing media (Bambanker, Lymphotec, Inc. cat. no. BB02) at a density of $10^7$ cells/mL, and transferred to cryogenic vials to be frozen in a Mr. Frosty™ freezing container (Nalgene) as described by the manufacturer. Following 2 hours incubation at −80° C. in the Mr. Frosty™ container, cells were thawed by incubation in a water bath at 37° C. and washed with DPBS to remove freezing medium and unbound backpacks. Alternative freezing lengths are described in other Examples (e.g. 2 hours or 2 weeks). Cells were then cultured in CM-NK with 20 ng/mL IL-2 at 37° C. and 5% $CO_2$.

Example 23: Cell Expansion of CD8 T Cell in IL-2 Containing CM-T

Figure 10:
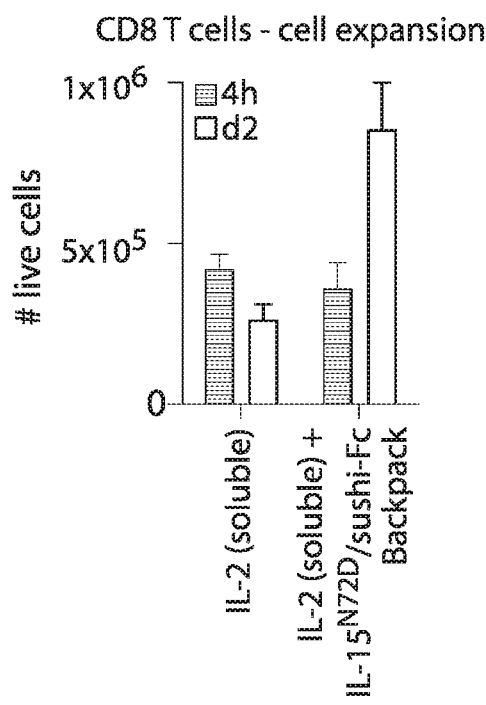
FIG. 10 depicts T cell expansion analysis. CD8 T cells were conjugated (right group) or not (left group) with IL-15$^{N72D}$/sushi-Fc Backpacks before freezing in FBS+5% DMSO overnight. Upon thawing, both groups were cultured in IL-2 containing media (20 ng/ml) and the number of live cells was measured after 4 hours (gray bars) and on day 2 (black bars) by flow cytometry. Complete media for this experiment was IMDM (Lonza), Glutamaxx (Life Tech), 20% FBS (Life Tech), 2.5 ug/ml human albumin (Octapharma), 0.5 ug/ml Inositol (Sigma).

CD8 T cells were incubated with IL-15$^{N72D}$/sushi-Fc backpacks before freezing in FBS+5% DMSO overnight. Upon thawing, backpack-associated T cells were cultured in IL-2 containing CM-T, along with control CD8 T cell treated the same way but without backpacks. The number of live cells was measured at the indicated times after thawing. Association of backpacks before cryopreservation of activated CD8 T cells promoted a faster recovery of CD8 T cells. Indeed, already 2 days after thawing, backpack-carrying CD8 T cells expanded ~2-fold, as compared to CD8 T cells thawed and culture in IL-2 containing media. (FIG. 10).

Example 24: Cell Expansion of CD3 T Cell in IL-2 Free CM-T

Figure 11A:
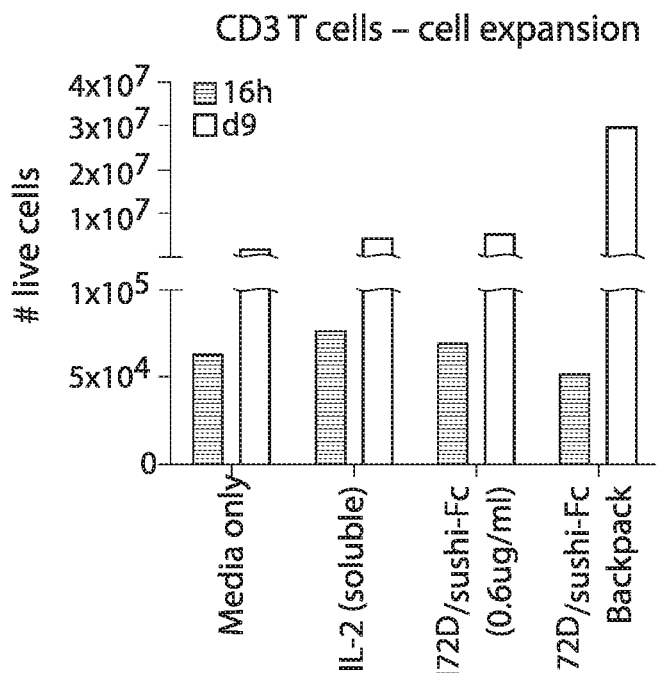
FIGS. 11A-11B shows T-cell expansion analysis.
Figure 11B:
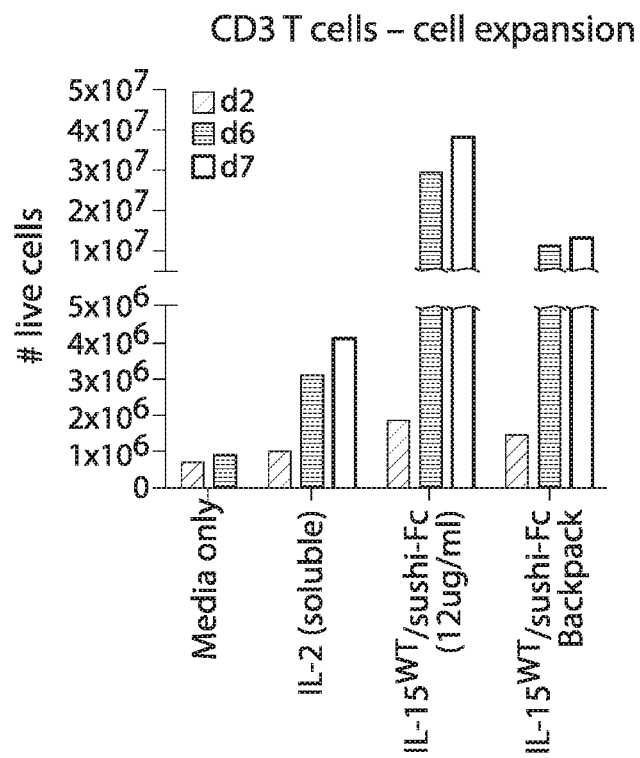

CD3 T cells were incubated with IL-15$^{N72D}$/sushi-Fc or IL-15$^{WT}$/sushi-Fc backpacks before freezing in serum-free media (Bambanker) for the indicated amount of time. Upon thawing, backpack-associated CD3 T cells were cultured in IL-2 free CM-T, along with control CD3 T cell treated the same way but without backpacks. Among the controls tested were CD3 T cells thawed and cultured in IL-2 free CM-T ("Media only"), CD3 T cells thawed and cultured in soluble IL-2 containing (20 ng/ml) CM-T ("IL-2 (soluble)"), CD3 T cells thawed and cultured in soluble IL-15$^{N72D}$/sushi-Fc ("IL-15$^{N72D}$/sushi-Fc (0.6 ug/ml)") or in soluble IL-15$^{WT}$/sushi-Fc containing ("IL-15$^{WT}$/sushi-Fc (12 ug/ml)") CM-T. The number of live cells was measured at the indicated times after thawing. Association of backpacks before cryopreservation of activated CD3 T cells increased the expansion of CD3 T cells. Indeed, after a week or 9 days, the gain in CD3 T cell expansion was ~5-fold to –10-fold, respectively (FIGS. 11A-11B).

Example 25: Cell Expansion of NK-92 Cell Line and Primary NK Cells

Figure 12A:
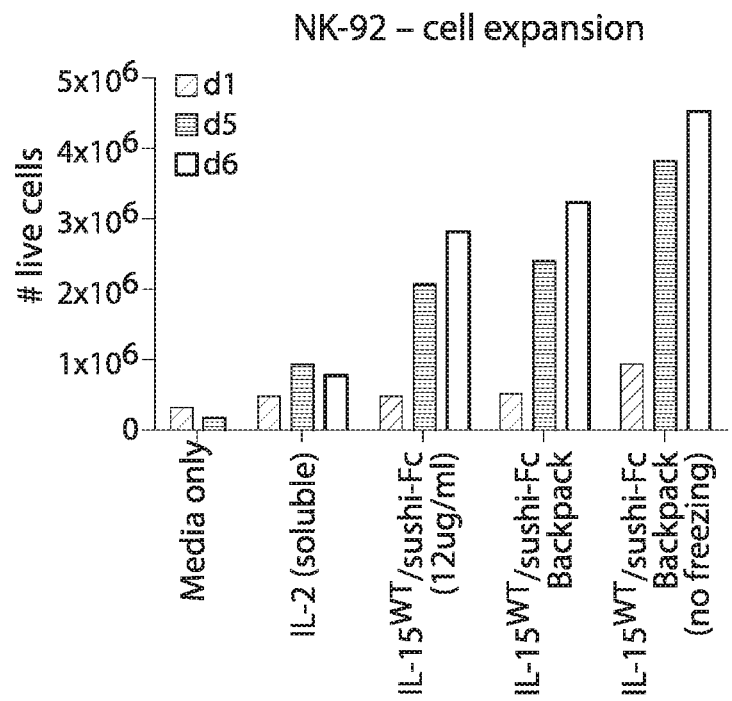
FIGS. 12A-12B depict NK-92 cell line and primary NK cell expansion analysis.
Figure 12B:
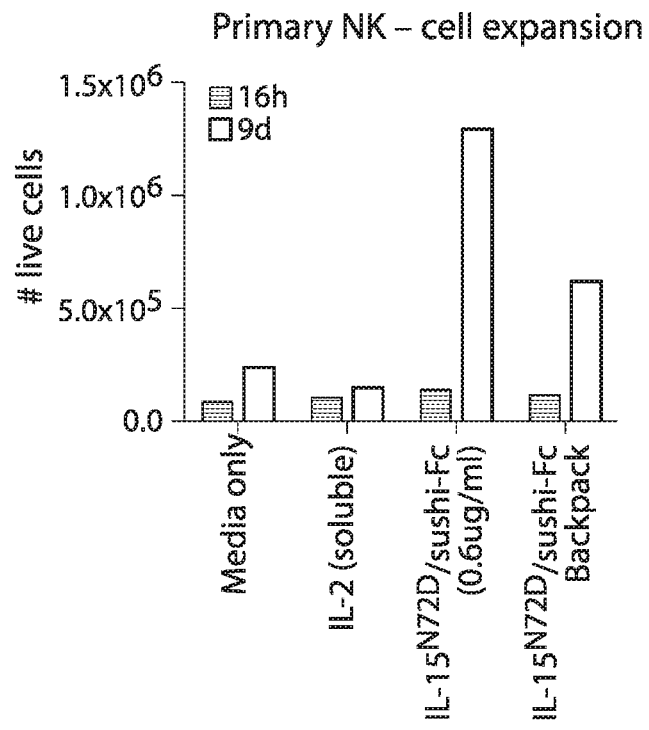

NK-92 cells and primary NK cells were incubated with IL-15$^{N72D}$/sushi-Fc or IL-15$^{WT}$/sushi-Fc backpacks before freezing in serum-free media (Bambanker) for the indicated amount of time. Upon thawing, backpack-associated cells were cultured in IL-2 free CM-NK. Among the controls tested were primary NK cells and NK-92 cells thawed and cultured in IL-2 free CM-NK ("Media only"), primary NK cells and NK-92 cells thawed and cultured in soluble IL-2 containing (20 ng/ml) CM-NK ("IL-2 (soluble)"), primary NK cells and NK-92 cells thawed and cultured in soluble IL-15$^{N72D}$/sushi-Fc ("IL-15$^{N72D}$/sushi-Fc (0.6 ug/ml)"), NK-92 cells thawed and cultured in soluble IL-15$^{WT}$/sushi-Fc containing ("IL-15$^{WT}$/sushi-Fc (12 ug/ml)") CM-NK, NK-92 cells associated with IL-15$^{WT}$/sushi-Fc backpacks but not cryopreserved and cultured in IL-2 free CM-NK ("IL-15$^{WT}$/sushi-Fc backpack (no freezing)"). The number of live cells was measured at the indicated times after thawing. Association of backpacks before cryopreservation of NK-92 and primary NK cells increased the expansion of cells. Indeed, after 5 days, the gain in NK-92 cell expansion was ~2.5-fold as compared to IL-2 containing NK-92 cultures treated the same way. The maximum expansion was ~4-fold for backpack-treated, not cryopreserved NK-92 cells. Primary NK cell expansion was also increased ~5-fold as compared to IL-2 containing primary NK cultures treated the same way (FIGS. 12A-12B).

Example 26: T Cell Subsets and Activation

Figure 13A:
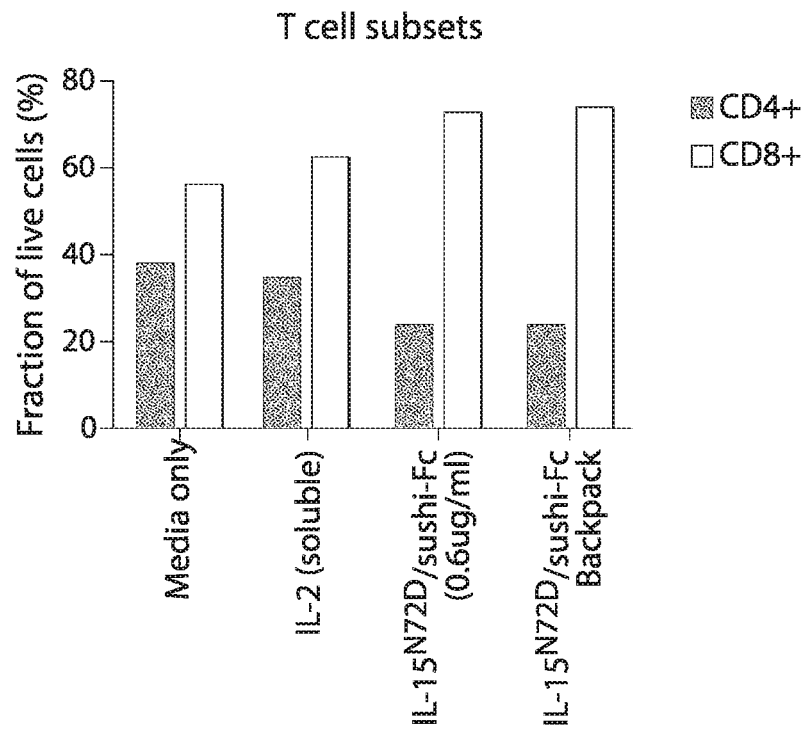
FIGS. 13A-13B depict T cell subset analysis.
Figure 13B:
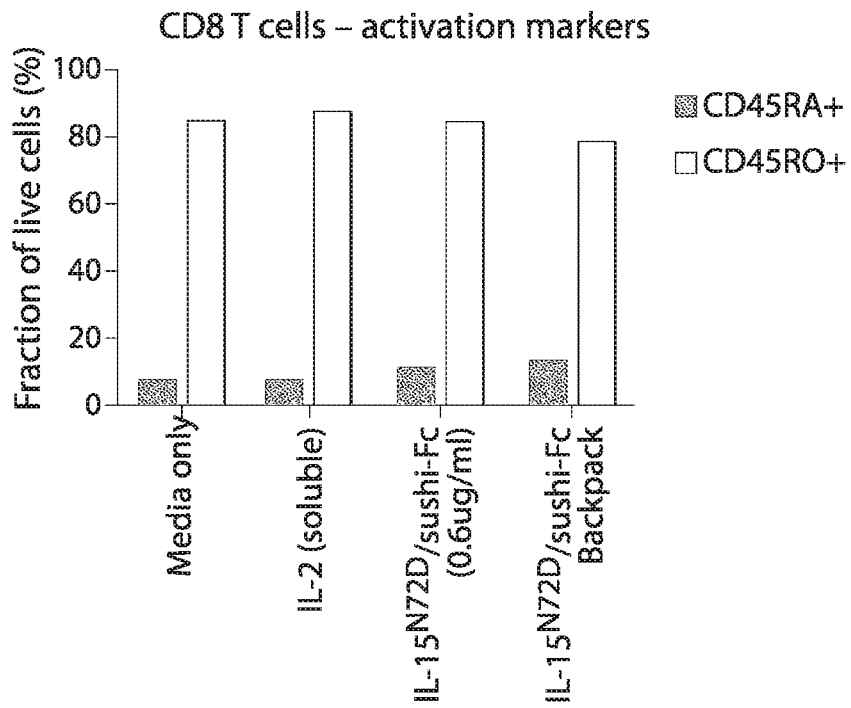

CD3 T cells treated as in Example 24 were further characterized by flow cytometry using the following fluorochrome-conjugated antibodies (BD Biosciences): CD4, CD8, CD45RA and CD45RO. Treatment with IL-15$^{N72D}$/sushi-Fc, either in solution or as a backpack, increased the proportion of CD8 T cells, without affecting their activation state, measured as fraction CD45RA+ (FIGS. 13A-13B).

Example 27: Short Term Potency of Activated CD3 T Cells Against Target Cell

Figure 14A:
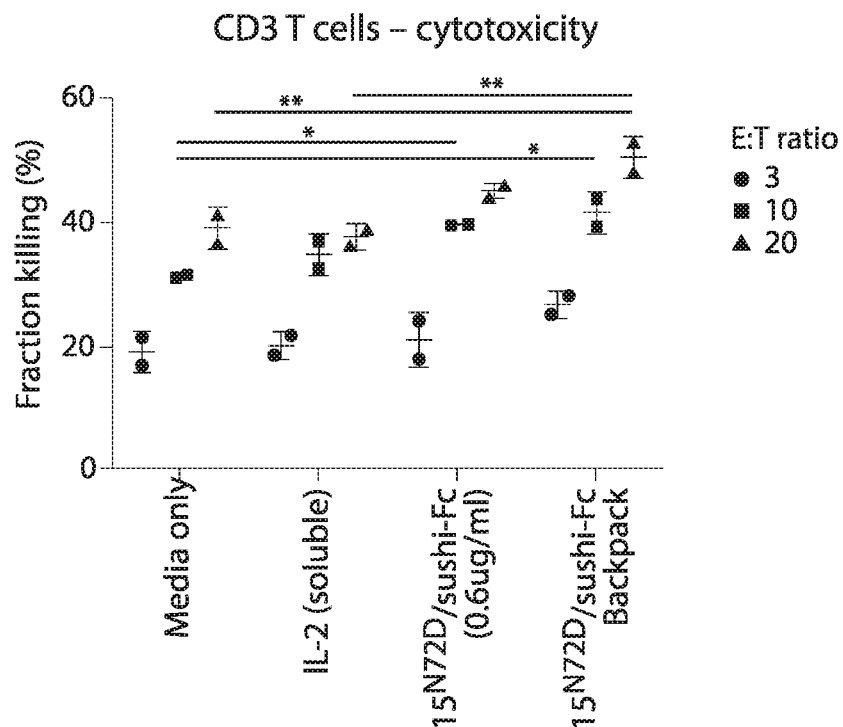
FIGS. 14A-14B depict T cell potency analysis.
Figure 14B:
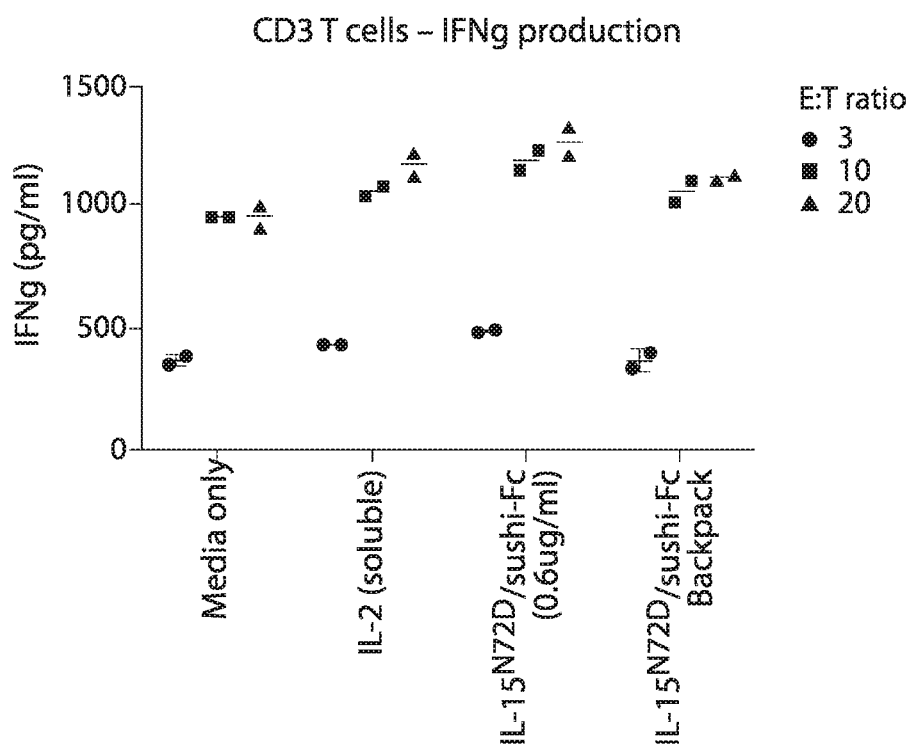

The cytotoxic activity of CD3 T cells treated as in Example 24 was characterized 1 day after thawing. CD3 T cells were co-cultured with target cells (Daudi, ATCC) previously labeled with PKH67 (Sigma) at different effector to target (E:T) ratios. Killing of target cells was measured by flow cytometry after 16 hours. The co-culture was performed in CM-T with IL-2 (20 ng/ml) for 16 hours. Dead cells were stained with Propidium Iodide (PI, BD Biosciences) and analyzed by flow cytometry. The fraction killing was calculated after dividing the number of PI+ PKH67+ cells by the total number of PKH67+ cells and subtracting the ratio obtained from culturing the target cells alone (background target cell viability). Cell co-culture supernatants from the cytotoxicity assay was harvested after centrifugation of the cells and stored at –20° C. IFNg concentration in supernatants was measured by ELISA (R&D) following the manufacturer's specifications. Backpack association did not hamper CD3 T cells in exerting their cytotoxic activity. To the contrary, association of IL-15$^{N72D}$/sushi-Fc backpacks before cryopreservation improved the potency of CD3 T cells, as compared to IL-2 containing CD3 T cell cultures treated the same way (FIGS. 14A-14B).

Example 28: Long Term Potency of Activated CD8 T Cells Against Target Cells

Figure 15A:
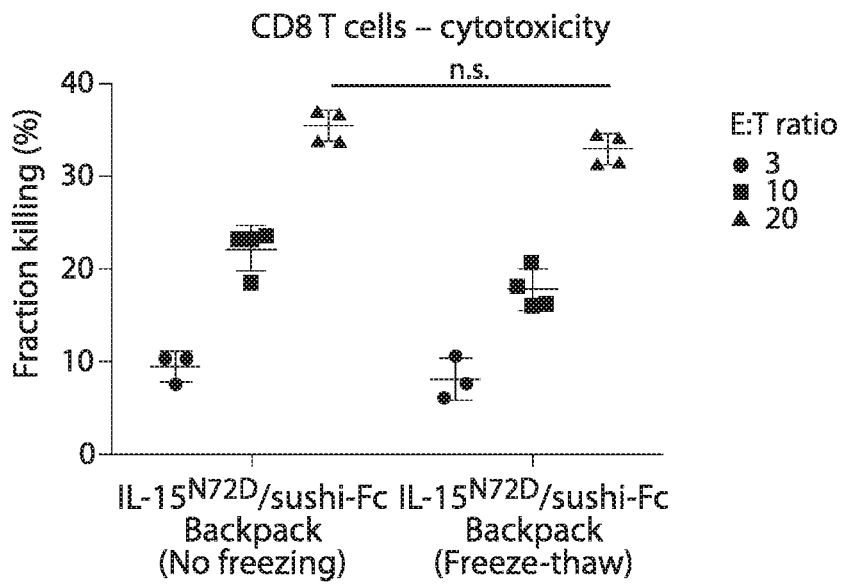
FIGS. 15A-15B depict T cell potency analysis.
Figure 15B:
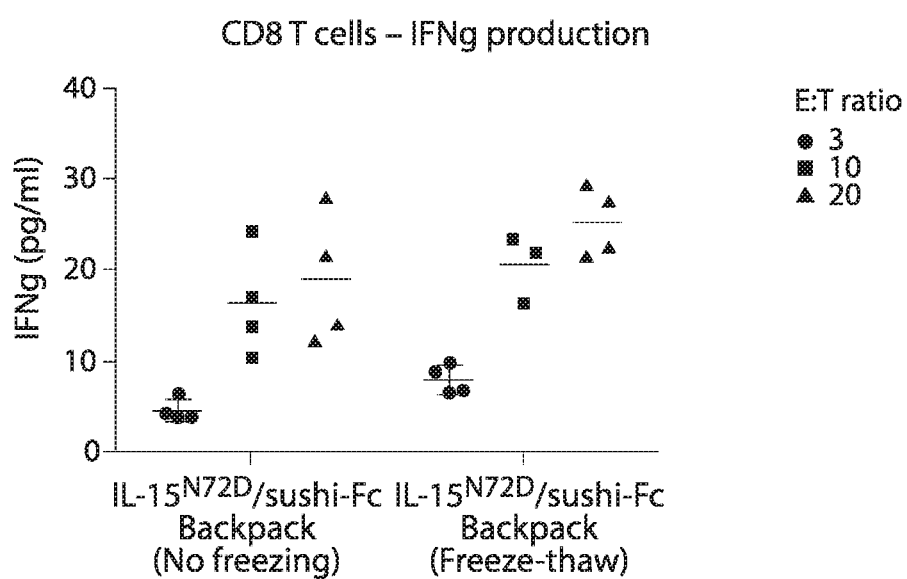

CD8 T cells were incubated with IL-15$^{N72D}$/sushi-Fc backpacks and either cryopreserved or returned to culture with IL-2 free CM-T. Their cytotoxic activity was compared after 18 days of culture in IL-2 free CM-T. CD8 T cells were co-cultured with target cells (Daudi, ATCC) previously labeled with PKH67 (Sigma) at different effector to target (E:T) ratios. Killing of target cells was measured by flow cytometry after 16 hours. The co-culture was performed in CM-T with IL-2 (20 ng/ml) for 16 hours. Dead cells were stained with Propidium Iodide (BD Biosciences) and analyzed by flow cytometry. The fraction killing was calculated after dividing the number of PI+ PKH67+ cells by the total number of PKH67+ cells and subtracting the ratio obtained from culturing the target cells alone (background target cell viability). Cell co-culture supernatants from the cytotoxicity assay was harvested after centrifugation of the cells and stored at –20° C. IFNg concentration in supernatants was measured by ELISA (R&D) following the manufacturer's specifications. Backpack association to CD8 T cells allowed them to expand and survive for 18 days in IL-2 free cultures and completely abolished the negative effects of cryopreservation on T cells (FIGS. 15A-15B).

Example 29: Potency of Activated CD8 T Cells Against Target Cell in Presence of IL-2

Figure 16A:
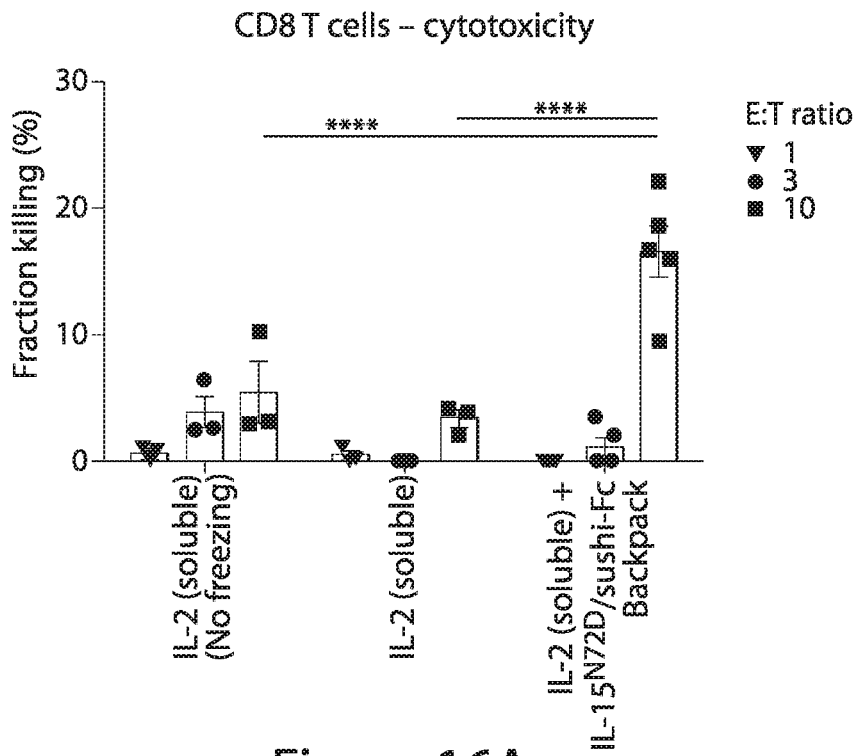
FIGS. 16A-16B depict T cell potency analysis.
Figure 16B:
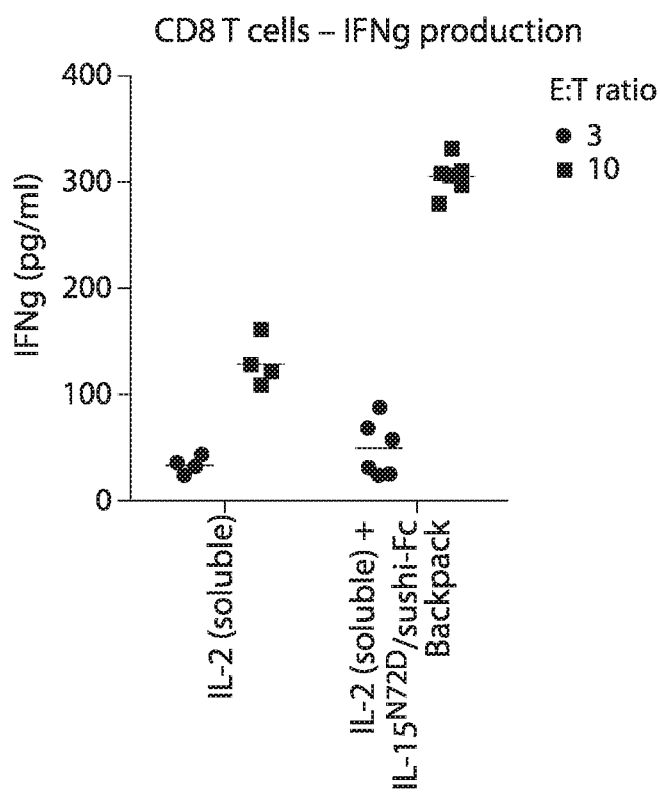

The cytotoxic activity of CD8 T cells treated as in Example 23 was characterized. CD8 T cells were co-cultured with target cells (Daudi, ATCC) previously labeled with PKH67 (Sigma) at different effector to target (E:T) ratios. Killing of target cells was measured by flow cytometry after 16 hours. The co-culture was performed in CM-T with IL-2 (20 ng/ml) for 16 hours. Dead cells were stained with Propidium Iodide (BD Biosciences) and analyzed by flow cytometry. The fraction killing was calculated after dividing the number of PI+ PKH67+ cells by the total number of PKH67+ cells and subtracting the ratio obtained from culturing the target cells alone (background target cell viability). Cell co-culture supernatants from the cytotoxicity assay was harvested after centrifugation of the cells and stored at −20° C. IFNg concentration in supernatants was measured by ELISA (R&D) following the manufacturer's specifications. Backpack association to CD8 T cells before cryopreservation and the presence of soluble IL-2 during culturing after thawing improved the potency of activated CD8 T cells, as compared to thawed CD8 T cells cultured in IL-2 containing CM-T (FIGS. 16A-16B).

Example 30: Potency of Primary NK Cells Against Target Cells

Figure 17A:
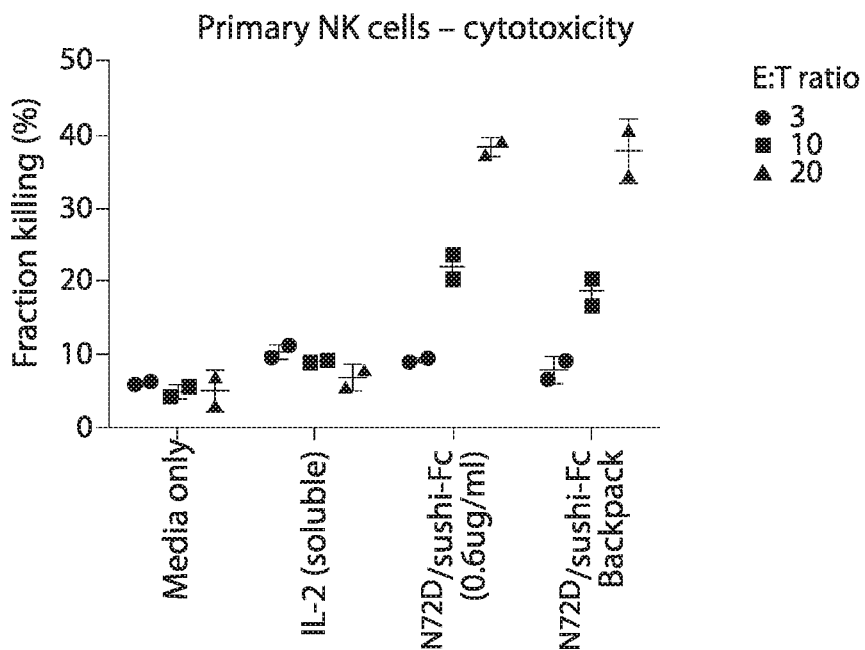
FIGS. 17A-17B depict primary NK cell potency analysis.
Figure 17B:
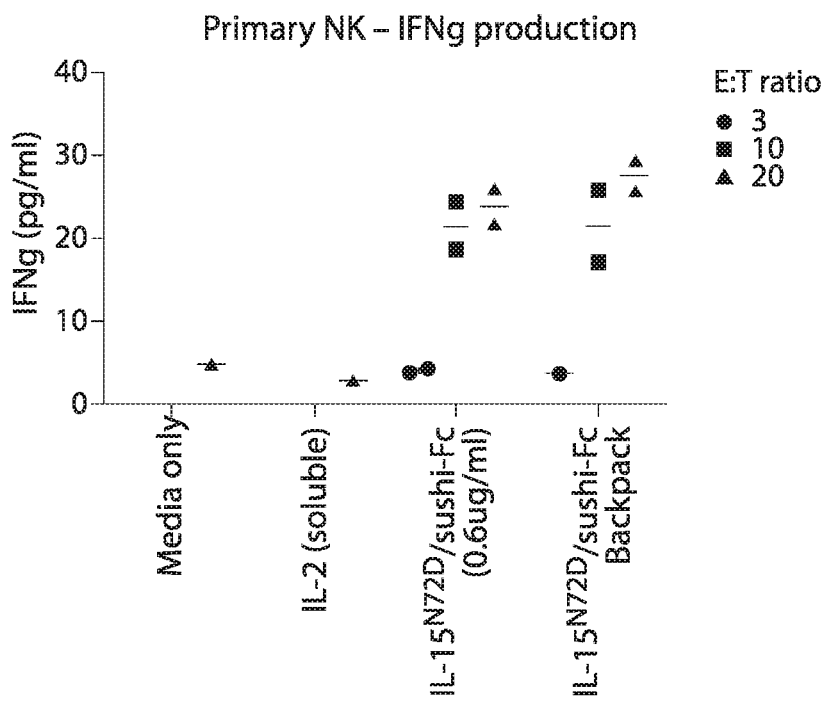

The cytotoxic activity of primary NK cells treated as in Example 25 was characterized. Primary NK cells were co-cultured with target cells (Daudi, ATCC) previously labeled with PKH67 (Sigma) at different effector to target (E:T) ratios. Killing of target cells was measured by flow cytometry after 16 hours. The co-culture was performed in CM-NK with IL-2 (20 ng/ml) for 16 hours. Dead cells were stained with Propidium Iodide (BD Biosciences) and analyzed by flow cytometry. The fraction killing was calculated after dividing the number of PI+ PKH67+ cells by the total number of PKH67+ cells and subtracting the ratio obtained from culturing the target cells alone (background target cell viability). Cell co-culture supernatants from the cytotoxicity assay was harvested after centrifugation of the cells and stored at −20° C. IFNg concentration in supernatants was measured by ELISA (R&D) following the manufacturer's specifications. Backpack association with primary NK cells before cryopreservation clearly improved the potency of primary NK cells, as compared to cryopreserved primary NK cells cultured in IL-2 containing CM-NK (FIGS. 17A-17B).

Example 31: Isolation and Activation of Primary Murine CD8 T Cells

Murine CD8 T cells were purified from spleens of C57B/6 mice through negative selection. The cells were activated by plating at a density of $10^6$/mL on 6-well plates coated with anti-CD3 and anti-CD28 antibodies (BE0001-1 and BE0015-1 respectively, Bio-Xcell) in murine T-cell complete media (CM-mT: RPMI, 10% FBS, 1×Pen-Strep, 1×L-Glut, 50 uM beta-mercaptoethanol, Sigma; ITS 1%, Sigma; Day 0). After one day of incubation, murine IL-2 (20 ng/mL; 402-ML, R&D Systems) and murine IL-7 (0.5 ng/mL; 407-ML, R&D Systems) were added (Day 1). After an additional day of incubation, the cells were re-seeded to $0.2 \times 10^5$ cells/mL (Day 2) and then re-seeded to the same density again the following day (Day 3). Cells were harvested on Day 4 for backpack attachment.

Figure 18A:
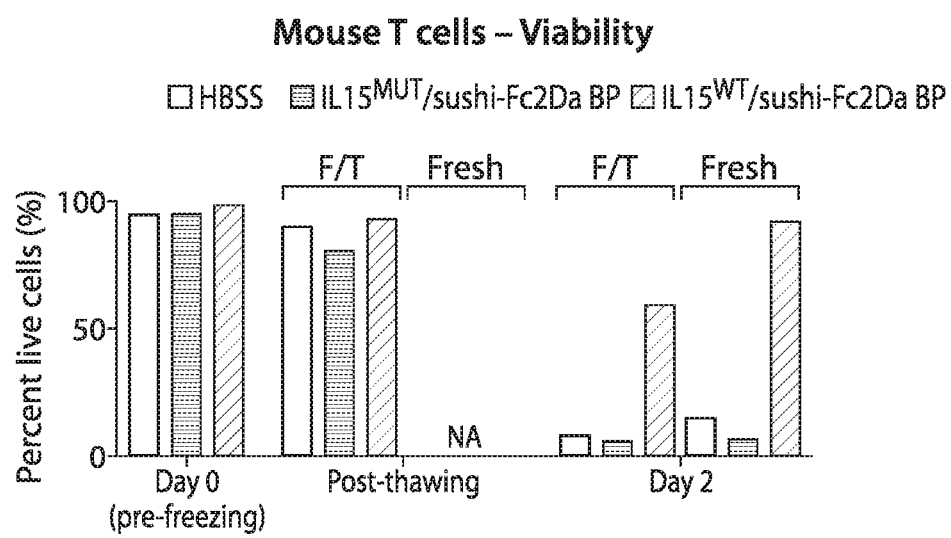
FIGS. 18A-18B depict primary mouse T cell viability analysis.
Figure 18B:
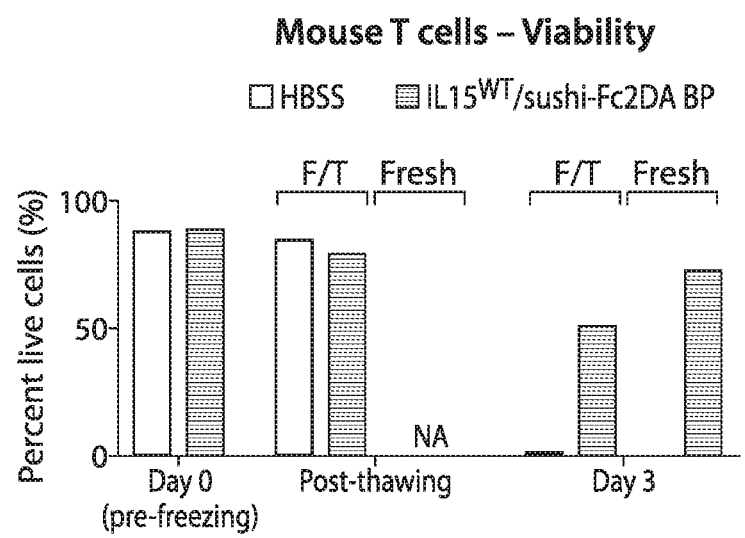

Example 32: Viability of Primary Frozen Murine CD8 T Cells in IL-2-Free CM-mT Cells generated in Example 31 were incubated with Hank's Balanced Salt Solution (HBSS, no backpack control) or backpacks comprising a non-functional IL15 mutant ($IL15^{MUT}$/sushi-FcDa BP) or functional IL-15 ($IL15^{WT}$/sushi-FcDa BP) as described for IL15/sushi-Fc constructs in Example 4. The $IL15^{MUT}$/sushi-Fc2 Da protein comprises a IL-15 D8N mutation and possesses minimal biological activity; backpacks from $IL15^{MUT}$/sushi-Fc2 Da were used as a negative control to explore requirement of functionally active IL-15. $IL15^{WT}$/sushi-FcDa and $IL15^{MUT}$/sushi-Fc2 Da proteins were produced as described for IL15/sushi-Fc in Example 14. The cells were frozen at −80 C for 5 days before being thawed as described in Example 4. The thawed cells were cultured in CM-mT for 2 days (FIG. 18A) or 3 days (FIG. 18B). Viability of the cells before freezing ("pre-freezing"), immediately after thawing ("Post-thawing"), and after culturing was assessed via dual-fluorescence microscopy (Acridine Orange/Propidium Iodide, Cat. CS2-0106; Cellometer, Nexcelom).

Figure 19:
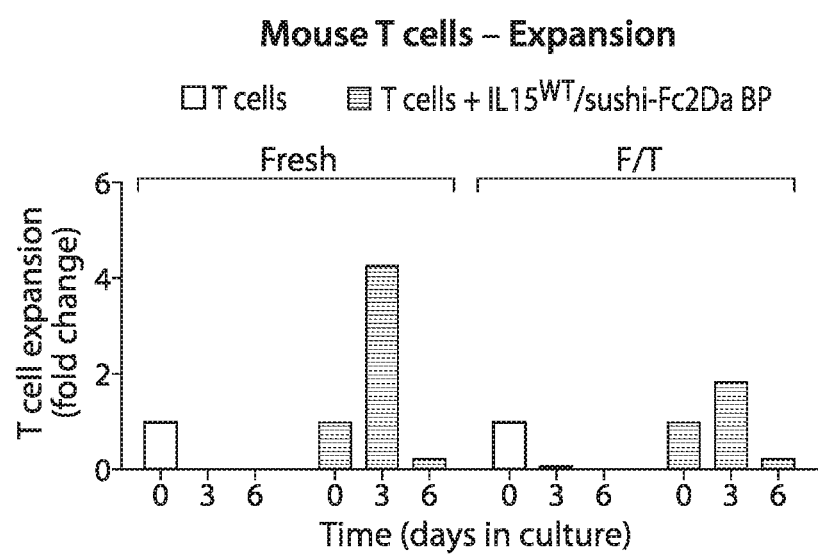
FIG. 19 depicts primary mouse T cell expansion in culture. In vitro activated T cells (see Example 31) were incubated (on day 0) with Hank's Balanced Salt Solution (HBSS; black bars) or conjugated with IL-15$^{WT}$/sushi-Fc2 Da backpacks (gray hatched bars). After washing (see Example 21), T cells were split in half and either cultured in CM-mT (see Example 31) or frozen in serum-free media (Bambanker) for 5 days. T cells were counted post-thawing and after 3 and 6 days in culture by dual-fluorescence microscopy (Acridine Orange/Propidium Iodide, Cat. CS2-0106; Cellometer, Nexcelom). Results are reported as fold-change over day 0. F/T: freeze/thaw. BP: backpacks.

Example 33: Expansion of Primary Frozen Murine CD8 T Cells in IL-2-Free CM-mT Activated murine CD8 T cells were incubated in HBSS ("T-cells") or backpack comprising functional IL15 ("T-cells+$IL15^{WT}$/Sushi-Fc2 Da BP") as described. The cells were then frozen for 3 hours in a Mr. Frosty at −80 C ("FIT"). After thawing the cells were cultured in CM-mT with viability assessed via dual-fluorescence microscopy acridine orange/propidium iodide (AO/PI) on a Cellometer K2 (Nexcelom Bioscience LLC) just after thaw ("0") and on Days 3 and 6 of culturing. T-cells and backpacked T-cells that were not subjected to freeze/thaw ("Fresh") were similarly cultured for comparison (see FIG. 19). Data are reported as viable cell count normalized to the viable cell count on Day 0 (i.e. "fold-change" of viable cells over viable cell count on Day 0).

Example 34: Expansion of Primary Human CD8 T Cells in IL-2-Free CM-T

Figure 20A:
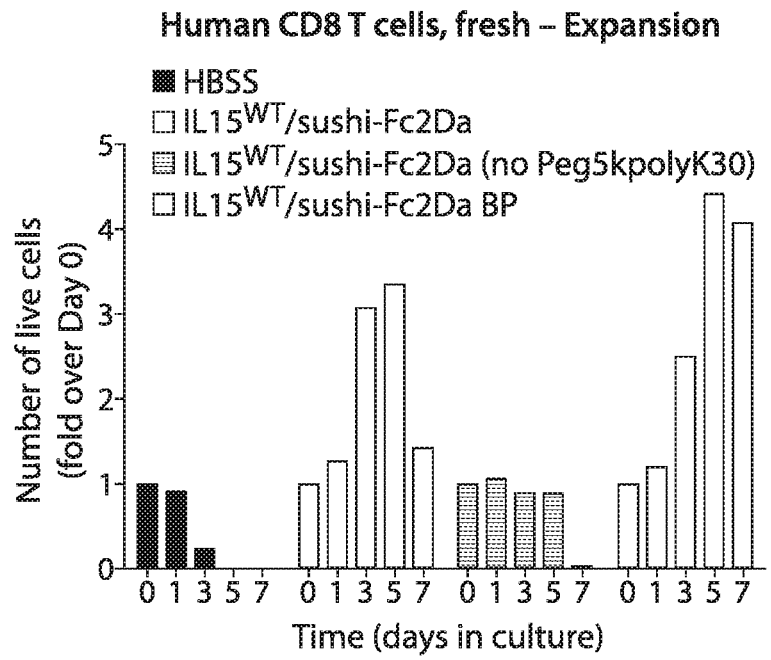
FIGS. 20A-20B depict primary human T cell expansion in culture. In both panels, CD8 T cells were incubated with Hank's Balanced Salt Solution (HBSS; black bars) or with IL-15$^{WT}$/sushi-Fc2 Da (dark gray bars), or conjugated with IL-15$^{WT}$/sushi-Fc2 Da backpacks without Peg5kpolyK30 (light gray bars) or with IL-15$^{WT}$/sushi-Fc2 Da backpacks with Peg5kpolyK30 (open bars).
Figure 20B:
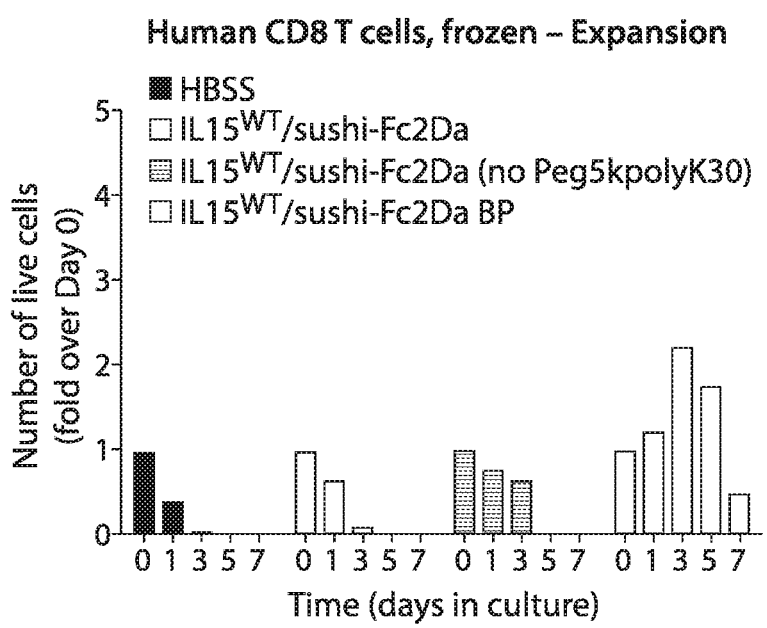

Human CD8 T-cells were isolated and purified as described in Examples 2 and 3. Cells were incubated in HBSS, soluble (non-backpacked) $IL15^{WT}$/sushi-Fc2 Da, backpacks comprising $IL15^{WT}$/sushi-Fc2 Da without PEG5kpolyK30 polycation, or backpacks comprising $IL15^{WT}$/sushi-Fc2 Da with PEG5kpolyK30 as described in Example 4. Treated cells were washed and either put directly into culture (FIG. 20A) or subjected to freezing for 7 days before thawing and culturing (FIG. 20B). The cells were counted via flow cytometric counting beads (C36950 Thermofisher) before plating (Day 0) and on Days 1, 3, 5, and 7 of culture. Data are reported as fold increase over cell count on Day 0.

Example 35: In Vivo Expansion of CD8 T Cells Frozen with IL15 Backpack

Figure 21A:
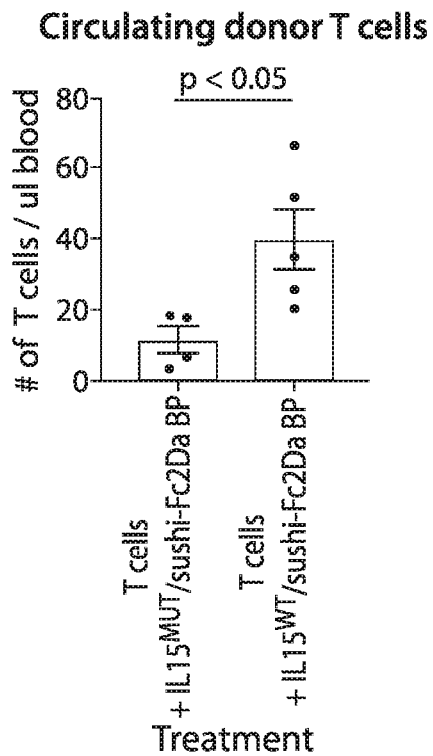
FIGS. 21A-21B depict the concentration of transferred mouse Pmel T cells in the circulation of recipient mice. In both panels, primary murine T cells were isolated from spleens of Pmel transgenic mice and activated in vitro (Example 31).
Figure 21B:
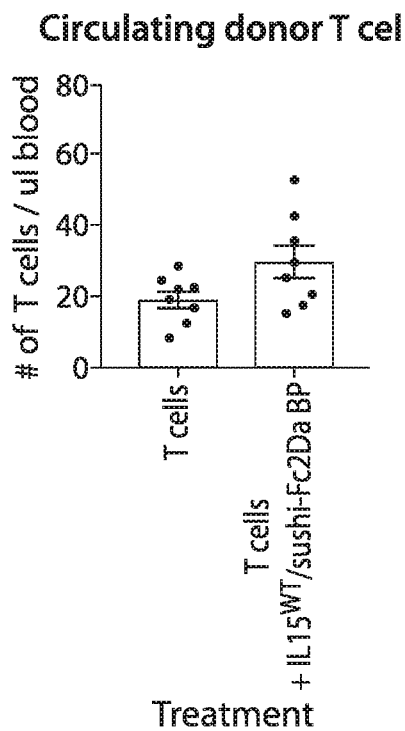

B16F10 murine melanoma cells were injected intra-dermally into the shaved flank of 6-week old C57BL/6 female mice ($10^5$ cells/mouse). After 7 days, Pmel transgenic CD8 T cells previously incubated with HBSS, $IL15^{WT}$/sushi-Fc2 Da backpack, or non-functional $IL15^{MUT}$/sushi-Fc2 Da backpack and frozen in Bambanker for 5 days were thawed and dosed intravenously ($10^7$/mouse). On day 5 (FIG. 21A) or day 7 (FIG. 21B), transferred T-cells in the blood were counted by flow cytometry. Data are reported as number of donor CD8 T cells per ul of blood.

Example 36: Tumor Targeting of CD8 T Cells Frozen with IL15 Backpack

Figure 22:
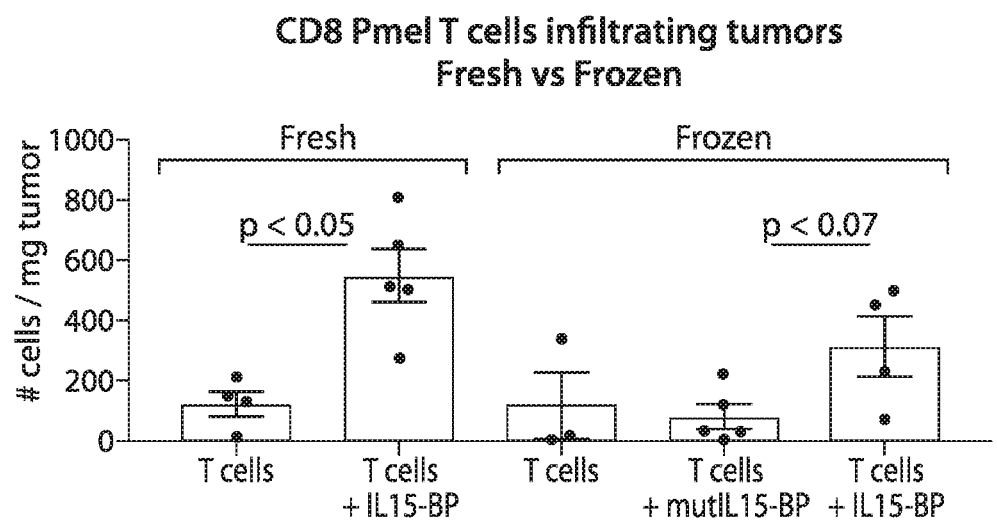
FIG. 22 depicts the concentration of transferred mouse Pmel T cells in the tumor microenvironment of recipient mice. Primary murine T cells were isolated from spleens of Pmel transgenic mice and activated in vitro (Example 31). Activated T cells were either incubated with Hank's Balanced Salt Solution (HBSS), conjugated with IL-15$^{MUT}$/sushi-Fc2 Da backpacks or conjugated with IL-15$^{WT}$/sushi-Fc2 Da backpacks. Animals were either injected with fresh or frozen cells ($10^7$ per mouse). The number of live transferred T cells infiltrating the tumors was measured on day 26 by flow cytometry. Results are reported as number of T cells per mg of tumor. Statistical analysis by Mann-Whitney test. BP: backpacks.

Tumor masses from mice in Example 35 were excised and analyzed by flow cytometry. As reference, mice receiving fresh CD8 T cells (with or without $IL15^{WT}$/sushi-Fc2 Da backpack) are shown. Data are reported as number of donor CD8 T cells per mg tumor (FIG. 22).

---

We claim:

1. A frozen composition comprising a lymphocyte and a protein nanogel, wherein the protein nanogel comprises a plurality of conservation agents crosslinked to each other by a reversible linker, wherein at least one of the conservation agents comprises an IL-15 molecule complexed with a receptor polypeptide, the receptor polypeptide comprising a first domain comprising an amino acid sequence with at least 90% identity to the amino acid sequence of SEQ ID NO: 8 and having IL-15 binding activity.

2. The frozen composition of claim 1, wherein upon thawing of the frozen composition, the conservation agents improve one or more of viability, proliferation, cytotoxic activity, and activation of the lymphocyte compared to a corresponding lymphocyte in the absence of the protein nanogel.

3. The frozen composition of claim 1, wherein the IL-15 molecule comprises an amino acid sequence with at least 90% identity to the amino acid sequence of SEQ ID NO: 1 and has IL-15Rα binding activity.

4. The frozen composition of claim 1, wherein the lymphocyte is a T cell, a B cell, or a Natural Killer (NK) cell.

5. The frozen composition of claim 1, wherein the plurality of conservation agents further comprises a cytokine molecule.

6. The frozen composition of claim 5, wherein the cytokine molecule comprises IL-2, IL-6, IL-7, IL-12, IL-15, IL-17, IL-18, IL-21, IL-23, IL-4, IL-1α, IL-1β, IL-5, IFNγ, TNFα, IFNα, IFNβ, GM-CSF, or GCSF, or a variant thereof.

7. The frozen composition of claim 1, wherein the protein nanogel comprises an antibody molecule that binds CD45, integrin alpha-L (CD11a) integrin beta-2 (CD18), CD11b, CD11c, CD25, CD8, or CD4.

8. The frozen composition of claim 1, wherein the reversible linker is sensitive to redox, pH, or an enzyme.

9. The frozen composition of claim 1, wherein the IL-15 molecule comprises the amino acid sequence of SEQ ID NO: 1.

10. The frozen composition of claim 1, wherein the first domain comprises the amino acid sequence of SEQ ID NO: 8.

11. The frozen composition of claim 1, wherein the receptor polypeptide further comprises a second, heterologous domain comprising an Fc domain.

12. The frozen composition of claim 11, wherein the Fc domain comprises an amino acid sequence with at least 90% identity to the amino acid sequence of SEQ ID NO: 14.

13. The frozen composition of claim 1, wherein the protein nanogel is greater than 80% protein by weight.

14. The frozen composition of claim 1, wherein the protein nanogel further comprises a cationic block co-polymer comprising PEG and a poly-lysine.

15. The frozen composition of claim 1, wherein:
  (a) the IL-15 molecule comprises an amino acid sequence with at least 95% identity to the amino acid sequence of SEQ ID NO: 1 and has IL-15Rα binding activity;
  (b) the receptor polypeptide comprises:
    (i) a first domain comprising an amino acid sequence with at least 95% identity to the amino acid sequence of SEQ ID NO: 8 and having IL-15 binding activity; and (ii) a second, heterologous domain comprising an Fc domain comprising an amino acid sequence with at least 95% identity to the amino acid sequence of SEQ ID NO: 14; and (c) the protein nanogel further comprises a cationic block co-polymer comprising PEG having a molecular weight of about 1-10 kD and a poly-lysine having an average length of 10-50 amino acids.

16. A method for making a frozen composition, the method comprising:

providing an unfrozen composition comprising a lymphocyte and a protein nanogel; and reducing the temperature of the composition sufficiently for the composition to freeze, thereby to obtain the frozen composition, wherein the protein nanogel comprises a plurality of conservation agents crosslinked to each other by a reversible linker, wherein at least one of the conservation agents comprises an IL-15 molecule complexed with a receptor polypeptide, the receptor polypeptide comprising a first domain comprising an amino acid sequence with at least 90% identity to the amino acid sequence of SEQ ID NO: 8, and having IL-15 binding activity, wherein one or more of viability, proliferation, cytotoxic activity, and activation of the lymphocyte is improved, upon thawing, compared to a corresponding lymphocyte in the absence of the protein nanogel.

17. The method of claim 16, wherein the temperature is reduced to less than 0 degrees centigrade or less than negative 10 degrees centigrade.

18. The method of claim 16, wherein the receptor polypeptide further comprises a second, heterologous domain comprising an Fc domain.

19. The method of claim 16, wherein the lymphocyte is a T cell, a B cell, or a NK cell.

20. The method of claim 16, wherein the reversible linker is sensitive to redox, pH, or an enzyme.

* * * * *

SEQUENCE LISTING

```
<160> NUMBER OF SEQ ID NOS: 15

<210> SEQ ID NO 1
<211> LENGTH: 114
<212> TYPE: PRT
<213> ORGANISM: Homo sapiens

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 267
<212> TYPE: PRT
<213> ORGANISM: Homo sapiens

<400> SEQUENCE: 2

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
            115                 120                 125
```

```
Pro Ala Ala Ser Ser Pro Ser Ser Asn Asn Thr Ala Ala Thr Thr Ala
        130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                    165                 170                 175

Gln Thr Thr Ala Lys Asn Trp Glu Leu Thr Ala Ser Ala Ser His Gln
                180                 185                 190

Pro Pro Gly Val Tyr Pro Gln Gly His Ser Asp Thr Val Ala Ile
                195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                    245                 250                 255

Asp Glu Asp Leu Glu Asn Cys Ser His His Leu
                260                 265
```

```
<210> SEQ ID NO 3
<211> LENGTH: 205
<212> TYPE: PRT
<213> ORGANISM: Homo sapiens

<400> SEQUENCE: 3

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
                35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
                100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
        130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                    165                 170                 175

Gln Thr Thr Ala Lys Asn Trp Glu Leu Thr Ala Ser Ala Ser His Gln
                180                 185                 190

Pro Pro Gly Val Tyr Pro Gln Gly His Ser Asp Thr Thr
                195                 200                 205
```

```
<210> SEQ ID NO 4
<211> LENGTH: 172
<212> TYPE: PRT
```

-continued

<213> ORGANISM: Homo sapiens

<400> SEQUENCE: 4

```
Met Ala Pro Arg Arg Ala Arg Gly Cys Arg Thr Leu Gly Leu Pro Ala
1               5                   10                  15
Leu Leu Leu Leu Leu Leu Leu Arg Pro Pro Ala Thr Arg Gly Ile Thr
            20                  25                  30
Cys Pro Pro Pro Met Ser Val Glu His Ala Asp Ile Trp Val Lys Ser
        35                  40                  45
Tyr Ser Leu Tyr Ser Arg Glu Arg Tyr Ile Cys Asn Ser Gly Phe Lys
    50                  55                  60
Arg Lys Ala Gly Thr Ser Ser Leu Thr Glu Cys Val Leu Asn Lys Ala
65                  70                  75                  80
Thr Asn Val Ala His Trp Thr Thr Pro Ser Leu Lys Cys Ile Lys Pro
                85                  90                  95
Ala Ala Ser Ser Pro Ser Ser Asn Asn Thr Ala Ala Thr Thr Ala Ala
            100                 105                 110
Ile Val Pro Gly Ser Gln Leu Met Pro Ser Lys Ser Pro Ser Thr Gly
        115                 120                 125
Thr Thr Glu Ile Ser Ser His Glu Ser Ser His Gly Thr Pro Ser Gln
    130                 135                 140
Thr Thr Ala Lys Asn Trp Glu Leu Thr Ala Ser Ala Ser His Gln Pro
145                 150                 155                 160
Pro Gly Val Tyr Pro Gln Gly His Ser Asp Thr Thr
                165                 170
```

<210> SEQ ID NO 5
<211> LENGTH: 297
<212> TYPE: PRT
<213> ORGANISM: Homo sapiens

<400> SEQUENCE: 5

```
Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Ile Asn
        35                  40                  45
Lys Ala Thr Asn Val Ala His Trp Thr Thr Pro Ser Leu Lys Cys Ile
    50                  55                  60
Arg Glu Pro Lys Ser Cys Asp Lys Thr His Thr Cys Pro Pro Cys Pro
65                  70                  75                  80
Ala Pro Glu Leu Leu Gly Gly Pro Ser Val Phe Leu Phe Pro Pro Lys
                85                  90                  95
Pro Lys Asp Thr Leu Met Ile Ser Arg Thr Pro Glu Val Thr Cys Val
            100                 105                 110
Val Val Asp Val Ser His Glu Asp Pro Glu Val Lys Phe Asn Trp Tyr
        115                 120                 125
Val Asp Gly Val Glu Val His Asn Ala Lys Thr Lys Pro Arg Glu Glu
    130                 135                 140
Gln Tyr Asn Ser Thr Tyr Arg Val Val Ser Val Leu Thr Val Leu His
145                 150                 155                 160
Gln Asp Trp Leu Asn Gly Lys Glu Tyr Lys Cys Lys Val Ser Asn Lys
                165                 170                 175
Ala Leu Pro Ala Pro Ile Glu Lys Thr Ile Ser Lys Ala Lys Gly Gln
```

```
                180               185               190
    Pro Arg Glu Pro Gln Val Tyr Thr Leu Pro Pro Ser Arg Asp Glu Leu
            195                 200                 205

Thr Lys Asn Gln Val Ser Leu Thr Cys Leu Val Lys Gly Phe Tyr Pro
        210                 215                 220

Ser Asp Ile Ala Val Glu Trp Glu Ser Asn Gly Gln Pro Glu Asn Asn
    225                 230                 235                 240

Tyr Lys Thr Thr Pro Pro Val Leu Asp Ser Asp Gly Ser Phe Phe Leu
                    245                 250                 255

Tyr Ser Lys Leu Thr Val Asp Lys Ser Arg Trp Gln Gln Gly Asn Val
                260                 265                 270

Phe Ser Cys Ser Val Met His Glu Ala Leu His Asn His Tyr Thr Gln
                275                 280                 285

Lys Ser Leu Ser Leu Ser Pro Gly Lys
                290                 295
```

<210> SEQ ID NO 6
<211> LENGTH: 114
<212> TYPE: PRT
<213> ORGANISM: Homo sapiens

<400> SEQUENCE: 6

```
    Asn Trp Val Asn Val Ile Ser Asp Leu Lys Lys Ile Glu Asp Leu Ile
    1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
        50                  55                  60

Asn Leu Ile Ile Leu Ala Asn Asp Ser Leu Ser Ser Asn Gly Asn Val
    65                  70                  75                  80

Thr Glu Ser Gly Cys Lys Glu Cys Glu Glu Leu Glu Glu Lys Asn Ile
                    85                  90                  95

Lys Glu Phe Leu Gln Ser Phe Val His Ile Val Gln Met Phe Ile Asn
                100                 105                 110

Thr Ser
```

<210> SEQ ID NO 7
<211> LENGTH: 62
<212> TYPE: PRT
<213> ORGANISM: Homo Sapiens

<400> SEQUENCE: 7

```
    Cys Pro Pro Pro Met Ser Val Glu His Ala Asp Ile Trp Val Lys Ser
    1               5                   10                  15

Tyr Ser Leu Tyr Ser Arg Glu Arg Tyr Ile Cys Asn Ser Gly Phe Lys
                20                  25                  30

Arg Lys Ala Gly Thr Ser Ser Leu Thr Glu Cys Val Leu Asn Lys Ala
                35                  40                  45

Thr Asn Val Ala His Trp Thr Thr Pro Ser Leu Lys Cys Ile
        50                  55                  60
```

<210> SEQ ID NO 8
<211> LENGTH: 65
<212> TYPE: PRT
<213> ORGANISM: Homo sapiens

<400> SEQUENCE: 8

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65
```

<210> SEQ ID NO 9
<211> LENGTH: 62
<212> TYPE: PRT
<213> ORGANISM: Homo sapiens

<400> SEQUENCE: 9

```
Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Ile Asn Lys Ala
        35                  40                  45

Thr Asn Val Ala His Trp Thr Thr Pro Ser Leu Lys Cys Ile
    50                  55                  60
```

<210> SEQ ID NO 10
<211> LENGTH: 65
<212> TYPE: PRT
<213> ORGANISM: Homo sapiens

<400> SEQUENCE: 10

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Ile Asn
        35                  40                  45

Lys Ala Thr Asn Val Ala His Trp Thr Thr Pro Ser Leu Lys Cys Ile
    50                  55                  60

Arg
65
```

<210> SEQ ID NO 11
<211> LENGTH: 228
<212> TYPE: PRT
<213> ORGANISM: Homo sapiens

<400> SEQUENCE: 11

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
```

```
            50                  55                  60
Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 12
<211> LENGTH: 232
<212> TYPE: PRT
<213> ORGANISM: Homo sapiens

<400> SEQUENCE: 12

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

Ser Lys Leu Thr Val Asp Lys Ser Arg Trp Gln Gln Gly Asn Val Phe
          195                  200                  205

Ser Cys Ser Val Met His Glu Ala Leu His Asn His Tyr Thr Gln Lys
    210                  215                  220

Ser Leu Ser Leu Ser Pro Gly Lys
225                  230

<210> SEQ ID NO 13
<211> LENGTH: 326
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                 10               15

Ser Thr Ser Glu Ser Thr Ala Ala Leu Gly Cys Leu Val Lys Asp Tyr
          20                 25                 30

Phe Pro Glu Pro Val Thr Val Ser Trp Asn Ser Gly Ala Leu Thr Ser
        35                 40                 45

Gly Val His Thr Phe Pro Ala Val Leu Gln Ser Ser Gly Leu Tyr Ser
   50                  55                 60

Leu Ser Ser Val Val Thr Val Pro Ser Ser Asn Phe Gly Thr Gln Thr
65                  70                 75                 80

Tyr Thr Cys Asn Val Asp His Lys Pro Ser Asn Thr Lys Val Asp Lys
             85                 90                 95

Thr Val Glu Arg Lys Cys Cys Val Glu Cys Pro Pro Cys Pro Ala Pro
        100                105               110

Pro Val Ala Gly Pro Ser Val Phe Leu Phe Pro Pro Lys Pro Lys Asp
        115                120               125

Thr Leu Met Ile Ser Arg Thr Pro Glu Val Thr Cys Val Val Val Asp
    130                  135                140

Val Ser His Glu Asp Pro Glu Val Gln Phe Asn Trp Tyr Val Asp Gly
145                  150                155                160

Val Glu Val His Asn Ala Lys Thr Lys Pro Arg Glu Glu Gln Phe Asn
            165                170               175

Ser Thr Phe Arg Val Val Ser Val Leu Thr Val Val His Gln Asp Trp
        180                185               190

Leu Asn Gly Lys Glu Tyr Lys Cys Lys Val Ser Asn Lys Gly Leu Pro
    195                  200                205

Ala Pro Ile Glu Lys Thr Ile Ser Lys Thr Lys Gly Gln Pro Arg Glu
    210                  215                220

Pro Gln Val Tyr Thr Leu Pro Pro Ser Arg Glu Glu Met Thr Lys Asn
225                  230                235                240

Gln Val Ser Leu Thr Cys Leu Val Lys Gly Phe Tyr Pro Ser Asp Ile
               245                250               255

Ala Val Glu Trp Glu Ser Asn Gly Gln Pro Glu Asn Asn Tyr Lys Thr
        260                265               270

Thr Pro Pro Met Leu Asp Ser Asp Gly Ser Phe Phe Leu Tyr Ser Lys
        275                280               285

Leu Thr Val Asp Lys Ser Arg Trp Gln Gln Gly Asn Val Phe Ser Cys
    290                  295                300

Ser Val Met His Glu Ala Leu His Asn His Tyr Thr Gln Lys Ser Leu
305                  310                315                320

Ser Leu Ser Pro Gly Lys
        325

<210> SEQ ID NO 14
<211> LENGTH: 228
<212> TYPE: PRT
<213> ORGANISM: Homo sapiens

<400> SEQUENCE: 14

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 15
<211> LENGTH: 293
<212> TYPE: PRT
<213> ORGANISM: Homo sapiens

<400> SEQUENCE: 15

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Arg Lys Cys Cys Val Glu Cys Pro Pro Cys Pro Ala Pro Pro
65                  70                  75                  80

Val Ala Gly Pro Ser Val Phe Leu Phe Pro Pro Lys Pro Lys Asp Thr
                85                  90                  95
```

```
Leu Met Ile Ser Arg Thr Pro Glu Val Thr Cys Val Val Asp Val
            100             105             110
Ser His Glu Asp Pro Glu Val Gln Phe Asn Trp Tyr Val Asp Gly Val
            115             120             125
Glu Val His Asn Ala Lys Thr Lys Pro Arg Glu Glu Gln Phe Asn Ser
    130             135             140
Thr Phe Arg Val Val Ser Val Leu Thr Val Val His Gln Asp Trp Leu
145             150             155             160
Asn Gly Lys Glu Tyr Lys Cys Lys Val Ser Asn Lys Gly Leu Pro Ser
                165             170             175
Ser Ile Glu Lys Thr Ile Ser Lys Thr Lys Gly Gln Pro Arg Glu Pro
            180             185             190
Gln Val Tyr Thr Leu Pro Pro Ser Arg Glu Glu Met Thr Lys Asn Gln
            195             200             205
Val Ser Leu Thr Cys Leu Val Lys Gly Phe Tyr Pro Ser Asp Ile Ala
            210             215             220
Val Glu Trp Glu Ser Asn Gly Gln Pro Glu Asn Asn Tyr Lys Thr Thr
225             230             235             240
Pro Pro Met Leu Asp Ser Asp Gly Ser Phe Phe Leu Tyr Ser Lys Leu
                245             250             255
Thr Val Asp Lys Ser Arg Trp Gln Gln Gly Asn Val Phe Ser Cys Ser
                260             265             270
Val Met His Glu Ala Leu His Asn His Tyr Thr Gln Lys Ser Leu Ser
            275             280             285
Leu Ser Pro Gly Lys
            290
```